United States Patent
Kraftson et al.

[11] Patent Number: 6,151,581
[45] Date of Patent: Nov. 21, 2000

[54] SYSTEM FOR AND METHOD OF COLLECTING AND POPULATING A DATABASE WITH PHYSICIAN/PATIENT DATA FOR PROCESSING TO IMPROVE PRACTICE QUALITY AND HEALTHCARE DELIVERY

[75] Inventors: Raymond H. Kraftson; Marguerite O. Kraftson, both of Villanova; Michael Mudditt, Jamison; John J. Schrogie, Valley Forge; William H. Simon, Villanova, all of Pa.

[73] Assignee: PulseGroup Inc., Villanova, Pa.

[21] Appl. No.: 08/991,506

[22] Filed: Dec. 16, 1997

Related U.S. Application Data

[60] Provisional application No. 60/033,099, Dec. 17, 1996, and provisional application No. 60/044,085, Apr. 21, 1997.

[51] Int. Cl.⁷ .................................................. G06F 17/60
[52] U.S. Cl. ................................ 705/3; 705/2; 705/10; 707/102
[58] Field of Search ........................... 705/1, 2, 3, 10; 600/300; 707/100, 101, 102, 103, 505, 506, 507

[56] References Cited

U.S. PATENT DOCUMENTS

| | | | |
|---|---|---|---|
| 4,345,315 | 8/1982 | Cadotte et al. | 705/10 |
| 4,858,121 | 8/1989 | Barber et al. | 705/2 |
| 4,992,939 | 2/1991 | Tyler | 704/9 |
| 5,307,262 | 4/1994 | Ertel | 705/2 |
| 5,341,291 | 8/1994 | Roizen et al. | 600/300 |
| 5,365,425 | 11/1994 | Torma et al. | 705/2 |
| 5,410,646 | 4/1995 | Tondevold et al. | 707/507 |
| 5,519,607 | 5/1996 | Tawil | 705/2 |
| 5,572,421 | 11/1996 | Altman et al. | 705/3 |
| 5,642,731 | 7/1997 | Kehr | 600/300 |
| 5,673,691 | 10/1997 | Abrams et al. | 600/300 |
| 5,706,441 | 1/1998 | Lockwood | 705/3 |
| 5,724,580 | 3/1998 | Levin et al. | 707/104 |
| 5,748,907 | 5/1998 | Crane | 705/2 |
| 5,772,585 | 6/1998 | Lavin et al. | 600/300 |
| 5,802,493 | 9/1998 | Sheflott et al. | 705/1 |
| 5,822,744 | 10/1998 | Kesel | 706/52 |
| 5,823,948 | 10/1998 | Ross, Jr. et al. | 600/300 |
| 5,842,175 | 11/1998 | Andros et al. | 705/3 |
| 5,845,253 | 12/1998 | Rensimer et al. | 705/2 |
| 5,845,254 | 12/1998 | Lockwood et al. | 705/2 |
| 5,909,669 | 6/1999 | Havens | 705/11 |
| 5,924,073 | 7/1999 | Tyuluman et al. | 705/2 |

OTHER PUBLICATIONS

Dillman, Mail and Telephone Surveys: The Total Design Method, pp. 79–118, 1978.

*Primary Examiner*—James P. Trammell
*Assistant Examiner*—Nicholas David Rosen

[57] ABSTRACT

A system and method relates to the field of building and administrating a patient management and health care management database containing data relevant to the clinical care of patients, to the management of the practices to which the patients belong, and to outcomes of that health care and practice management. The disclosed system encompasses (i) designing and administering paper and pen and hand held computer survey instruments; (ii) administering and collecting completed surveys (iii) building and managing a database of information collected from the surveys; (iv) analyzing data collected from the surveys; (v) and providing clinical practices with summary information. Summary information may be used to improve patient care, health outcomes, and the management of physician practices.

21 Claims, 32 Drawing Sheets

THIS SURVEY IS TOTALLY ANONYMOUS. PLEASE TAKE A MOMENT TO RATE THE FOLLOWING. THANK YOU.

|  | VERY SATISFIED | SATISFIED | NEUTRAL | DISSATISFIED | VERY DISSATISFIED |
|---|---|---|---|---|---|
| 1. AVAILABILITY OF CONVENIENT PARKING/ PUBLIC TRANSPORTATION | ○ | ○ | ○ | ○ | ○ |
| 2. AVAILABILITY OF CONVENIENT APPOINTMENT | ○ | ○ | ○ | ○ | ○ |
| 3. COURTESY OF RECEPTION AT CHECK-IN | ○ | ○ | ○ | ○ | ○ |
| 4. COMFORT OF THE WAITING AREA | ○ | ○ | ○ | ○ | ○ |
| 5. INFORMATION PROVIDED ABOUT MY MEDICAL CONDITION | ○ | ○ | ○ | ○ | ○ |
| 6. ACCESSIBILITY OF OFFICE BY TELEPHONE | ○ | ○ | ○ | ○ | ○ |
| 7. FEELING ABOUT RECOMMENDING THIS OFFICE TO OTHERS | ○ | ○ | ○ | ○ | ○ |
| 8. SATISFACTION WITH PRIMARY INSURANCE | ○ | ○ | ○ | ○ | ○ |
| 9. INFORMATION PROVIDED ABOUT MY INSURANCE BY OFFICE STAFF | ○ | ○ | ○ | ○ | ○ |
| 10. PERSONAL MANNER OF THE DOCTOR | ○ | ○ | ○ | ○ | ○ |

11. ARE YOU VISITING THIS DOCTOR FOR THE FIRST TIME?  YES ○  NO ○
12. DID YOU SEE YOUR DOCTOR AT YOUR SCHEDULED TIME?  YES ○  NO ○

13. HOW LONG DID YOU WAIT TO SEE YOUR DOCTOR?  0-15 min ○  16-30 min ○  31-45 min ○  >45 min ○
14. WAS THE WAIT ACCEPTABLE ?  YES ○  NO ○
15. HOW MUCH TIME DID YOU SPEND WITH THE NURSE/ DOCTOR'S ASSISTANT?  0-10 min ○  11-20 min ○  21-30 min ○  >30 min ○
16. WAS THE TIME SPENT WITH THE NURSE/DOCTOR'S ASSISTANT USEFUL ?  YES ○  NO ○
17. HOW MUCH TIME DID YOU SPEND WITH YOUR DOCTOR?  0-10 min ○  11-20 min ○  21-30 min ○  >30 min ○
18. WAS THE TIME SPENT WITH SPEND WITH YOUR DOCTOR ?  YES ○  NO ○

19. YOUR PRIMARY INSURANCE PLAN   BC/BS ○  MEDICARE ○  MEDICARE HMO ○  HMO ○  OTHER ○
20. YOUR GENDER   MALE ○  FEMALE ○   21. YOUR BIRTHDATE   MONTH [  ]  YEAR [  ]
22. YOUR ZIP CODE [     ]   23. TODAY'S DATE   MONTH [  ]  YEAR [  ]

FOR PHYSICAN & OFFICE STAFF ONLY

WHAT IS THE ORIGIN OF THIS PATIENT'S PRIMARY DISEASE ?

| NOT APPLICABLE ○ | HEMATOLOGIC ○ | DERMATOLOGIC ○ | REPRODUCTIVE ○ |
| GI ○ | CNS ○ | PULMONARY ○ | ENT ○ |
| CARDIOVASCULAR ○ | MUSCULOSKELETAL ○ | ENDOCRINOLOGIC ○ | OTHER ○ |

DOES THIS PATIENT HAVE ANY OF THE FOLLOWING AS HIS/HER PRIMARY PROBLEM ?

| NOT APPLICABLE ○ | ASTHMA ○ | CHF ○ | COPD ○ |
| DIABETES ○ | ONCOLOGICAL ○ | PRACTICE TARGET ○ | |

PHYSICAN ID   16

FIG. 2B

PULSEDATA

THIS SURVEY IS TOTALLY ANONYMOUS, PLEASE ANSWER THE QUESTIONS TO THE BEST OF YOUR ABILITY.

DATE: MONTH___DAY___YEAR___
ZIP CODE_____ MALE   FEMALE

MARKING INSTRUCTIONS
- USE NO.2 PENCIL OR BLACK/BLUE INK PEN ONLY.
- DO NOT USE RED INK OR FELT TIP PENS.
- FILL THE OVAL COMPLETELY WITH A DARK MARK.
- MARK NO STRAY MARKS ON THE FORM.
- FOLD WHERE INDICATED/RETURN IN ENVELOPE PROVIDED.

TO BE COMPLETED BY THE DOCTOR AND PRACTICE STAFF :
DIAGNOSIS _____
WAS MEDICATION PRESCRIBED ?    YES/NO
IF SO, WHAT WAS (WERE) THE GENERIC AND / OR PRESCRIPTION BRAND NAME(S) ?_____

RATING SCALE(S)   INSURANCE PLAN_____

WHEN FILLING IN THIS FORM CERTAIN ABBREVIATIONS ARE USED, THE FOLLOWING ARE THE KEYS TO THESE ABBREVIATIONS.

IF YOU PREVIOUSLY HAVE TAKEN THE MEDICATION(S) NOTED ABOVE.
HAS IT (HAVE THEY) PERFORMED AS DESCRIBED ?   YES___ NO___
COMMENTS _____

KEY:
SA=STRONGLY AGREE      1W = 1 WEEK
A=AGREE                2W = 2 WEEKS
N=NEUTRAL              1M = 1 MONTH
D=DISAGREE             2M = 2 MONTHS
SD=STRONGLY DISAGREE

| # | Question | | | | | |
|---|---|---|---|---|---|---|
| 1. | HOW MANY VISITS HAVE YOU MADE RELATED TO RELATED TO THIS CONDITION ? | 1 | 2 | 3 | 4 | 5 MORE |
| 2. | AN APPOINTMENT WAS MADE WITHIN AN APPROPRIATE TIME CONSIDERING THE SERIOUSNESS OF MY CONDITION | SA | A | N | D | SD |
| 3. | THE RECEPTION AND CHECK-IN WERE COURTEOUS AND CARING | SA | A | N | D | SD |
| 4. | I HAD TO WAIT IN THE WAITING ROOM AFTER MY APPOINTED TIME | Y | N | | | |
| 5. | IF YES, IT WAS A REASONABLE WAIT | Y | N | | | |
| 6. | HOW MUCH TIME DID THE NURSE SPEND WITH YOU (IN MINIUTES) ? | 0-10 | 10-20 | 20-30 | 30-40 | MORE |
| 7. | THE TIME I SPENT WITH THE NURSE WAS WORTHWHILE | SA | A | N | D | SD |
| 8. | HOW MUCH TIME DID THE DOCTOR SPEND WITH YOU (IN MINIUTES) ? | 0-10 | 10-20 | 20-30 | 30-40 | MORE |
| 9. | THE DOCTOR THOUGHTFULLY COMMUNICATED WITH ME (LISTENED AND INFORMED) | SA | A | N | D | SD |
| 10. | THE DOCTOR'S TREATMENT IS IMPROVING MY CONDITION | SA | A | N | D | SD |
| 11. | IF YOUR ANSWER IS EITHER SA OR A, HOW MUCH TIME HAS ELAPSED FROM THE BEGINNING OF TREATMENT ? | 1W | 2W | 1M | 2M | MORE |
| 12. | I WAS PLAESED WITH THE RESULT OF MY VISIT | SA | A | N | D | SD |
| 13. | I CAN REACH THE DOCTOR EASILY AND PROMPTLY BY TELEPHONE | SA | A | N | D | SD |
| 14. | I WOULD RECOMMEND MY DOCTOR TO MY FRIENDS | SA | A | N | D | SD |
| 15. | I AM PLEASED WITH MY INSURANCE PLAN | SA | A | N | D | SD |
| 16. | AGE (IN YEARS) | 0-10 10-20 | 20-30 | 30-50 | 50-65 | 65-100 |

THIS SURVEY IS TOLLY ANONYMOUS, PLEASE ANSWER THE QUESTIONS TO THE BEST OF YOUR ABILITY.
THANK YOU

FIG. 2C

SAMPLE FILE LAYOUT
(CODING SHEET)

<u>GENERAL SPECIFICATIONS:</u> DATA CAPTURED FROM THE OUTCOMES INSTRUMENT WILL BE SUMMARIZED AS ONE ASCII RECORD. EACH FIELD WILL BE REPRESENTED BY ASCII PRINTABLE CODE; FIELDS WILL BE SEPARATED BY TAB CHARACTERS. ALL DATES MUST BE ZERO-FILLED. RECORDS WILL BE TERMUNATED BY CARRIAGE RETURN, LINEFEED CODES.

<u>DETAILED FIELD SPECIFICATIONS:</u>

PATIENT X RESPONSE

| FIELD NUMBER | FIELD DESCRIPTION | ALLOWED VALUES | COMMENTS | |
|---|---|---|---|---|
| Q119 | 10a – HAVE PROB. – HEART DIS | 1 = YES 2 = NO | VALUES ARE EXCLUSIVE | 1 |
| Q120 | 10b – RECEIVE TX – HEART DIS | 1 = YES 2 = NO | VALUES ARE EXCLUSIVE, IGNORED IF Q119 = 2 | 1 |
| Q121 | 10c – LIMIT ACTIV – HEART DIS | 1 = YES 2 = NO | VALUES ARE EXCLUSIVE, IGNORED IF Q119 = 2 | 1 |
| Q122 | 11a – HAVE PROB. – HIGH BLOOD | 1 = YES 2 = NO | VALUES ARE EXCLUSIVE | 2 |
| Q123 | 11b – RECEIVE TX – HIGH BLOOD | 1 = YES 2 = NO | VALUES ARE EXCLUSIVE, IGNORED IF Q122 = 2 | 2 |
| Q124 | 11c – LIMIT ACTIV – HIGH BLOOD | 1 = YES 2 = NO | VALUES ARE EXCLUSIVE, IGNORED IF Q122 = 2 | 2 |
| Q125 | 12a – HAVE PROB. – LUNG DIS | 1 = YES 2 = NO | VALUES ARE EXCLUSIVE | 1 |
| Q126 | 12b – RECEIVE TX – LUNG DIS | 1 = YES 2 = NO | VALUES ARE EXCLUSIVE, IGNORED IF Q125 = 2 | 1 |
| Q127 | 12c – LIMIT ACTIV – LUNG DIS | 1 = YES 2 = NO | VALUES ARE EXCLUSIVE, IGNORED IF Q125 = 2 | 1 |
| Q128 | 13a – HAVE PROB. – DIABETES | 1 = YES 2 = NO | VALUES ARE EXCLUSIVE | 2 |
| Q129 | 13b – RECEIVE TX – DIABETES | 1 = YES 2 = NO | VALUES ARE EXCLUSIVE, IGNORED IF Q128 = 2 | 2 |
| Q130 | 13c – LIMIT ACTIV – DIABETES | 1 = YES 2 = NO | VALUES ARE EXCLUSIVE, IGNORED IF Q128 = 2 | 2 |
| Q131 | 14a –HAVE PROB. – ULCER | 1 = YES 2 = NO | VALUES ARE EXCLUSIVE | 2 |
| Q132 | 14b – RECEIVE TX – ULCER | 1 = YES 2 = NO | VALUES ARE EXCLUSIVE, IGNORED IF Q131 = 2 | 2 |
| Q133 | 14c – LIMIT ACTIV – ULCER | 1 = YES 2 = NO | VALUES ARE EXCLUSIVE, IGNORED IF Q131 = 2 | 2 |
| Q134 | 15a HAVE PROB. – KIDNEY DIS | 1 = YES 2 = NO | VALUES ARE EXCLUSIVE | 2 |

FIG. 3A

| FIELD NUMBER | FIELD DESCRIPTION | ALLOWED VALUES | COMMENTS | |
|---|---|---|---|---|
| Q135 | 15b - RECEIVE TX - KIDNEY DIS | 1 = YES 2 = NO | VALUES ARE EXCLUSIVE, IGNORED IF Q134 = 2 | 2 |
| Q136 | 15c - LIMIT ACTIV - KIDNEY DIS | 1 = YES 2 = NO | VALUES ARE EXCLUSIVE, IGNORED IF Q134 = 2 | 2 |
| Q137 | 16a - HAVE PROB. - LIVER DIS | 1 = YES 2 = NO | VALUES ARE EXCLUSIVE | 2 |
| Q138 | 16b -RECEIVE TX - LIVER DIS | 1 = YES 2 = NO | VALUES ARE EXCLUSIVE, IGNORED IF Q 137 = 2 | 2 |
| Q139 | 16c - LIMIT ACTIV - LIVER DIS | 1 = YES 2 = NO | VALUES ARE EXCLUSIVE, IGNORED IF Q 137 = 2 | 2 |
| Q140 | 17a HAVE PROB. - ANEMIA | 1 = YES 2 = NO | VALUES ARE EXCLUSIVE | 2 |
| Q141 | 17b - RECEIVE TX - ANEMIA | 1 = YES 2 = NO | VALUES ARE EXCLUSIVE, IGNORED IF Q140 = 2 | 2 |
| Q142 | 17c -LIMIT ACTIV - ANEMIA | 1 = YES 2 = NO | VALUES ARE EXCLUSIVE, IGNORED IF Q140 = 2 | 2 |
| Q143 | 18a - HAVE PROB. - CANCER | 1 = YES 2 = NO | VALUES ARE EXCLUSIVE | 2 |
| Q144 | 18b - RECEIVE TX - CANCER | 1 = YES 2 = NO | VALUES ARE EXCLUSIVE, IGNORED IF Q143 = 2 | 2 |
| Q145 | 18c - LIMIT ACTIV - CANCER | 1 = YES 2 = NO | VALUES ARE EXCLUSIVE, IGNORED IF Q143 = 2 | 2 |
| Q146 | 19a - HAVE PROB. - DEPRESSION | 1 = YES 2 = NO | VALUES ARE EXCLUSIVE | 2 |
| Q147 | 19b - RECEIVE TX - DEPRESSION | 1 = YES 2 = NO | VALUES ARE EXCLUSIVE, IGNORED IF Q146 = 2 | 2 |
| Q148 | 19c - LIMIT ACTIV - DEPRESSION | 1 = YES 2 = NO | VALUES ARE EXCLUSIVE, IGNORED IF Q146 = 2 | 2 |
| Q149 | 20a - HAVE PROB. - OSTEOARTH | 1 = YES 2 = NO | VALUES ARE EXCLUSIVE | 1 |
| Q150 | 20b - RECEIVE TX - OSTEOARTH | 1 = YES 2 = NO | VALUES ARE EXCLUSIVE, IGNORED IF Q149 = 2 | 1 |
| Q151 | 20c - LIMIT ACTIV - OSTEOARTH | 1 = YES 2 = NO | VALUES ARE EXCLUSIVE, IGNORED IF Q149 = 2 | 1 |
| Q152 | 21a - HAVE PROB. - BACK PAIN | 1 = YES 2 = NO | VALUES ARE EXCLUSIVE | 1 |
| Q153 | 21b - RECEIVE TX - BACK PAIN | 1 = YES 2 = NO | VALUES ARE EXCLUSIVE, IGNORED IF Q152 = 2 | 1 |
| Q154 | 21c - LIMIT ACTIV - BACK PAIN | 1 = YES 2 = NO | VALUES ARE EXCLUSIVE, IGNORED IF Q152 = 2 | 2 |
| Q155 | 22a - HAVE PROB. | 1 = YES | VALUES ARE EXCLUSIVE | |

FIG. 3B

| FIELD NUMBER | FIELD DESCRIPTION | ALLOWED VALUES | COMMENTS | |
|---|---|---|---|---|
| | – RHEUM ARTH | 2 = NO | | |
| Q156 | 22b – RECEIVE TX – RHEUM ARTH | 1 = YES 2 = NO | VALUES ARE EXCLUSIVE, IGNORED IF Q155 = 2 | 2 |
| Q157 | 22c – LIMIT ACTIV – RHEUM ARTH | 1 = YES 2 = NO | VALUES ARE EXCLUSIVE, IGNORED IF Q155 = 2 | 2 |
| Q158 | 23a – HAVE PROB. – OTHER MED PROB | 1 = YES 2 = NO | VALUES ARE EXCLUSIVE | 1 |
| Q159 | 23b – RECEIVE TX – OTHER MED PROB | 1 = YES 2 = NO | VALUES ARE EXCLUSIVE, IGNORED IF Q158 = 2 | 2 |
| Q160 | 23c – LIMIT ACTIV – OTHER MED PROB | 1 = YES 2 = NO | VALUES ARE EXCLUSIVE, IGNORED IF Q158 = 2 | 2 |
| Q160 | 23 – OTH MED | TEXT | IGNORED IF Q158 = 2 | |

FIG. 3C

☐ POSITIVE RESPONSE
▨ NEUTRAL/DISSATISFIED RESPONSE

——— POSITIVE AGGREGATED PRIME HEALTH ACTIVITY
----- NEGATIVE AGGREGATED PRIME HEALTH ACTIVITY

☐ POSITIVE RESPONSE
▨ NEUTRAL/DISSATISFIED RESPONSE

—— POSITIVE AGGREGATED PRIME HEALTH ACTIVITY
---- NEGATIVE AGGREGATED PRIME HEALTH ACTIVITY

Patient User Interface

THESE SCREENS SHOW THE WAY THAT THE USER WILL KNOW THEY HAVE PRESSED A KEY, IF POSSIBLE A SOUND WILL ALSO BE USED FOR COMPLETE TACTILE RESPONSE

WHEN A KEY IS TOUCHED, THE KEY CHANGES COLOR FROM GREY TO BLACK

PHYSICANS DATA ENTRY SCREEN

PULSEPILOT PHYSICIAN DATA ENTRY SCREEN

PHYSICIAN

DATE

APPOINTMENT TIME

DIAGNOSIS 1

DIAGNOSIS 2

PLEASE LIST MEDICATIONS PRESCRIBED TO THIS PATIENT

MEDICATION 1

MEDICATION 2

FIG. 12

SYSTEM FOR AND METHOD OF COLLECTING AND POPULATING A DATABASE WITH PHYSICIAN/PATIENT DATA FOR PROCESSING TO IMPROVE PRACTICE QUALITY AND HEALTHCARE DELIVERY

This application claims the benefit of U.S. Provisional Application 60/033,099 filed Dec. 17, 1996 and of U.S. Provisional Application 60/044,085 filed Apr. 21, 1997.

FIELD OF THE INVENTION

This invention relates to the field of database population and processing, and more specifically to receiving and processing physician clinical and patient care survey information, populating and managing a database of such information, and providing health outcomes and clinical practice information for physician patient care and practice quality improvement.

BACKGROUND OF THE INVENTION

Today, the health care industry focuses on designing programs and products to manage patient problems in a useful, efficient, cost-effective and consumer-oriented manner. Hospital staff members, numerous health care providers and representatives of pharmaceutical research and development industry play an important decision-making role in determining the treatment for disease. However, that role is still ancillary to the patient's primary care physician who diagnoses the patient's problem and provides an individualized treatment regimen. Current treatment for many kinds of patients' problems reflects the health care industry's change of perspective from an episodic, systematic treatment of disease to the reduction of risk factors the prevention of disease, and the reduction of health care costs. A rapid dissemination of large amounts of information regarding the effectiveness of treatment regimens, the cost-effectiveness of these regimens, and of patient reactions to their health care complements this change of focus.

As a result of the focal change, many participants within the healthcare industry require rapid access to a large database of patient information about diagnosis, treatment, health outcomes, costs, and patient perspectives on their diagnosis, treatment within the context of the practice to which they belong. This information can be used to respond to research/practice generated questions regarding some or all of the following: (i) the most effective treatment for a disease or patient problem, (ii) regimens or methods of reducing risk and increasing adherence (iii), the costs to the practice associated with therapeutic regimens, (iv) degree of patient satisfaction, and patient satisfaction with and adherence to regimens, (v) differences of (i–iv) within different practice types, specialties, or geographic regions. The information falls into three areas: clinical information, physician/patient information, practice management/cost information, and health outcomes information.

Available survey methods and databases that collect and analyze these surveys have not been designed in a user-friendly, easily accessible manner that physicians can use to monitor patients and their practices. The primary sources for patient information have been hospital records/data; pharmaceutical industry studies, prescription information, and medical or healthcare provider claims databases. These databases often lack information about one or more of the following: diagnosis, treatment, the patient's perceptions of the diagnosis and treatment, and costs to the practice of the patient's care and perceptions of care. The research activities requiring this information may take many forms: determining which treatment for a disease is most effective, determining the costs associated with particular kinds of treatment, or identifying at-risk patient and patients' reactions to the diagnosis, treatment, and services provided.

Further, systems which attempt to provide automated health care management do not necessarily have direct input from the patient about the care given during a patient's visit. Such systems usually rely on claims and physician's files, as well as insurance information; such a system is disclosed in U.S. Pat. No. 5,301,105 entitled ALL CARE HEALTH MANAGEMENT SYSTEM, to Desmond D. Cummings, Jr. Other systems are designed to review and control data quality of patient data collected as clinical data for reporting of hospital claims, such as disclosed in U.S. Pat. No. 5,307,262 entitled PATIENT DATA QUALITY REVIEW METHOD AND SYSTEM, to Paul Y. Ertel. These systems, however, are not designed to collect patient data associated with a physician's interaction and treatment of the patient, and with the patient's visit to a practice. Finally, some devices are designed to collect patient satisfaction data associated with a physician's drug treatment plan, while also collecting clinical trial information. Such a system is described in U.S. Pat. No. 5,642,731 entitled METHOD AND APPARATUS FOR MONITORING THE MANAGEMENT OF DISEASE, to Bruce A. Kehr. These systems are, however, tailored to specific drug treatment plans.

Past efforts to assemble such a database and system have failed because of a difficulty of acquiring such information without interfering with the physician's practice. Industry attempts to install computers within a practice, or assemble the information through surveys suffer from the following problems. First, physicians have been trained to prepare an immediate and long range patient plan based upon their own knowledge rather than to gather survey information from patients. Second, physicians know the importance of keeping patient information confidentially and, therefore, will not readily divulge information from their patient records. Third, physicians have no easy way to relate one portion of the care they provide (e.g., how the patient is greeted) to another aspect of care (e.g., patient adherence to a regimen.) Fourth, if the physician directly asks a patient about the office services and clinical care, the patient may not give accurate and unbiased responses. Therefore, there is a need for a method of acquiring Physician/Patient/Practice information which a) is simple to implement (requires only a few minutes of the physician's and the patients' time); and b) maintains the confidentiality of each patient.

SUMMARY OF THE INVENTION

The present invention relates to a system and method for acquisition, management and processing of patient clinical information and patient satisfaction information received from a group of physician practices to provide practice performance information. The system and method include a data input process receiving data including a physician component having the patient clinical information and a patient component having the patient satisfaction information to provide practice-patient data; database processing which translates the practice-patient data to a predetermined format and stores the practice-patient data having the predetermined format in a database; and a data analysis process. The data analysis process includes a) selectively receiving practice-patient data from the database, b) analyzing the received practice patient data, and c) summarizing the patient satisfaction data to provide performance results. The system and method further include a data correlating process which correlates selected portions of the performance results associated with at least one of the group of physician practices with portions of the stored practice-patient data to provide a practice measure; and a report generation process to provide a report from the performance results and the practice measure.

BRIEF DESCRIPTION OF THE DRAWINGS

These and other features and advantages of the present invention will become apparent from the following detailed description, taken in conjunction with the accompanying drawings, wherein:

FIG. 2B illustrates a first machine-readable form used in an exemplary embodiment;

FIG. 2C illustrates a second machine-readable form used in an alternative exemplary embodiment;

FIG. 3A illustrates a first portion of an exemplary embodiment of a database file layout used in one embodiment of the present invention;

FIG. 3B illustrates a second portion of an exemplary embodiment of a database file layout used in one embodiment of the present invention;

FIG. 3C illustrates a final portion of an exemplary embodiment of a database file layout used in one embodiment of the present invention;

FIG. 11A illustrates a patient user interface of the electronic patient data collection system shown in FIG. 10 having numeric keypad entry in which a user is prompted to answer a survey question.

FIG. 11B illustrates a patient user interface of the electronic patient data collection system shown in FIG. 10 having numeric keypad entry in which a response is entered and a user is prompted to go to the next question.

FIG. 12 illustrates an exemplary physician data entry screen of the host device of one embodiment of the present invention.

DETAILED DESCRIPTION

Figure 1:
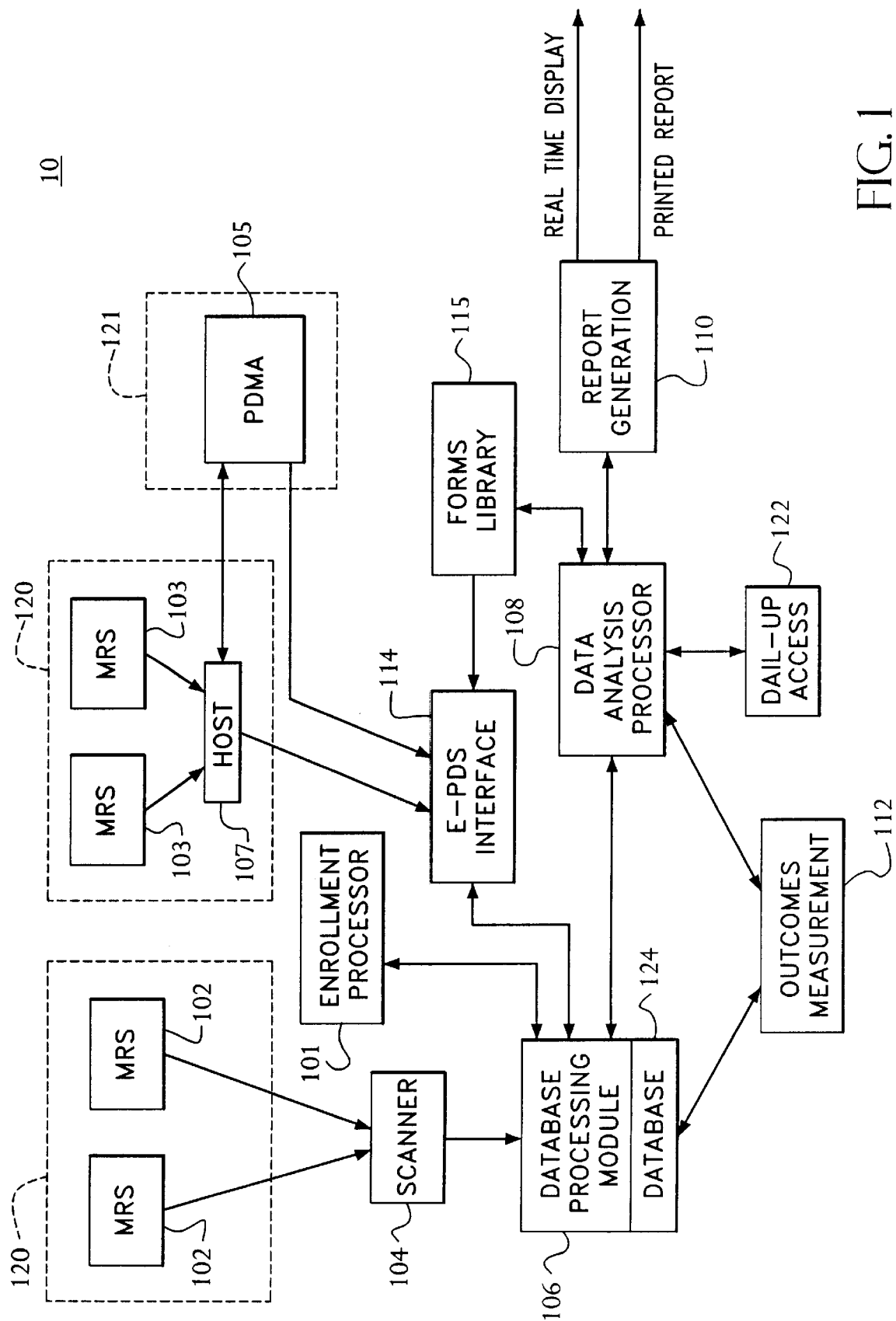
FIG. 1 illustrates the high-level block diagram of the Physician/Patient/Practice information management system of an embodiment of the present invention.

The present invention, designed for use in a large network of physician practices, provides a system for acquiring, managing, analyzing, and summarizing patient clinical care information, practice management/cost information, patient satisfaction, and health care outcomes information gathered from a large network of physician practices. The system includes: (1) machine-readable surveys that include separate sections of predetermined length that are administered to physicians and patients; or (1a) a handheld computer that administers the same survey to physicians and patients; (2) a scanner for collecting and reading the machine-readable survey; (3) a database for receiving scanned raw data from the machine readable survey and patient clinical information, patient, practice and cost information as well as for receiving raw survey data from the hand held computer.

The system also includes a database processor for translating the three different categories of data: patient clinical care data, practice management/costs data, and patient satisfaction/health care outcomes data to a predetermined format and for storing the translated data into a database. The results of the analysis can be accessed by member physicians who dial up the report generation module with their questions or who receive periodic practice reports as part of a regular routine. Report information may be able to be immediately displayed or received as printed reports. The system of the present invention may provide, for example, a) more objective assessment of the patient's progress and effectiveness of management; b) the determination of the effectiveness of management; c) validation of the process criteria for clinical audit; and d) assessment of cost effectiveness.

Knowing the a practice's health care statistics and having accessible and readable summary reports with statistical information about the practice may provide physicians with a mechanism for improving their practice, for example, reducing healthcare costs, increasing patient satisfaction and negotiating with managed care companies. For example, physicians in the system will know the precise costs of therapeutic regimens to the system and will be able to explain their practice's results in terms of a larger number of practices that have the same type of patients and use the same pharmaceutical regimens. Regional and national information may also be made available. During negotiations practices in the system can use this knowledge to achieve decreased costs to the practice for certain therapies as well as to improved compensation from the patients' insurance carrier.

The Data Collection and Reporting System

The present invention relates to a system that (1) gathers clinical information (information about the physician's clinical decision-making, including the assessment, therapeutic plan, and health outcomes of that plan); (2) gathers physician/patient information (information about the relationship of the patient to the physician, to the physician's practice and to prescribed therapeutic regimens; (3) gathers practice management/cost information (administrative information); (4) creates a database of this information; (5) analyzes data within the database; and (6) provides selected results of analysis of the information as a report. The data can be analyzed to provide physicians information regarding (A) clinical decisions that have been made and the effectiveness of the treatment regimens prescribed in their practice in comparison with other physicians participating in the System; (B) the perception of quality of the physician's practice and care from the patients' perspective, including the effects of actions taken by the physician to increase the quality of the practice and reactions to the physician's prescribed therapeutic regimens; and (C) the costs and management processes for use in defining the relationship between the physician and the managed care company; and insurance companies.

FIG. 1 illustrates the high level block diagram of the Physician/Patient information management system of an embodiment of the present invention. The system includes an Enrollment Processor 101 including enrollment forms (ERFs) for individual physicians or practices, a first data collection section having machine-readable survey form (MRSF) 102 which is completed by a patient and physician during a treatment session at a physician's practice 120 and a Scanner 104 for reading the survey information responses from the form and translating these into a Physician/Patient/Management data, and a Database Processing Module 106 including Database 124 for receiving the Physician/Patient data and for populating a Physician/Patient information database by storing the Physician/Patient information in a predetermined format. The System further includes a Data Analysis Processor 108 for analyzing the Physician/Patient/Management information according to selected data analysis packages such as Statistical Package for the Social Sciences (SPSS) or SAS, a Report Generation Module 110 for generating formatted reports containing results determined by the Data Analysis Processor 108, and an Outcomes Measurement Module 112 for recording and tracking performance of the System.

FIG. 1 further shows a second data collection section based on a hand-held computer data collection process. The system includes a remote Electronic Patient Data-collection System (E-PDS) 103 based on a hand-held computer which provides electronic forms that are to be completed by a patient and/or physician during a treatment session at a physician's practice 120, a host device 107, which may be implemented on a personal computer, for reading the survey information responses from the E-PDS 103 and translating these into a Physician/Patient data, an E-PDS Interface 114 for information downloading from/uploading to the E-PDS 103 through host device 107, and a Forms Library 115 for storing electronic forms to be loaded into E-PDSs 103.

The general operation of the process of the exemplary embodiment shown in FIG. 1 is now described. Each practice 120 completes an enrollment form which includes general information about the practice, and the enrollment process is described in detail subsequently. Prior to the clinical encounter, the patient form MRS 102 is prepared by writing relevant practice identification and management codes at the bottom of the form. For example, the practice's identification number is 000013 and the patient has a 15 minute appointment. Enough clipboards with the MRS Form 102, pens, and return envelopes are readied for each patient. During a clinical encounter at the physician practice location 102, physicians and patients fill out the MRS Form 102 with specific information relating to the treatment session ("Clinical Information"). The MRS Form 102 includes a small section in which the physician indicates the patient's problem or diagnosis. In a further embodiment, any medications or other treatment or risk reduction regimens prescribed in the small section of MRS form 102. For this alternative embodiment, for example, the physician may prescribe oxygen and support group therapy to patient X.

In a further embodiment, a section of the MRS 102 is devoted to patient identity, including a unique identity code given to the patient and the identity code given to the healthcare provider. Theses codes may be used by the physician to obtain statistical summaries about practice 102. The MRS Form 102 also includes a section for the patient to indicate satisfaction with the services that the practice provides and reactions to the therapeutic regimens prescribed by the physician. To respond to these items, the patient X first reads each item e.g., "1. Availability of convenient parking/public transportation. The patient then reads the five alternative responses, "Very Satisfied," "Satisfied," "Neutral," "Dissatisfied," or "Very Dissatisfied." She decides that she is very satisfied by the parking and blackens in the bubble "Very Satisfied." She then moves on to the next item and, one by one, responds until one bubble is blackened for each item in the section.

Once the MRS Form 102 is completed, the form is scanned by the Scanner 104 which reads the Physician/Patient/Practice Management (PPPM) information and provides the scanned data to the Database Processing Module 106. Database Processing Module 106 converts the received Physician/Patient Information into data records having a predetermined format and populates the database with these records. Alternatively, the PPPM information may be entered manually if no scanner is available.

In another embodiment the survey is administered through electronic screens by the E-PDS 103. The patient in Practice 120 receives the E-PDS 103 including stylus. The patient then places the stylus on the screen at the point that reads, for example, "Start" to begin the survey. The phrase Availability of convenient parking/public transportation appears on the screen with five rectangles that provide the five possible responses: "Very Satisfied," "Satisfied," "Neutral," "Dissatisfied" or "Very Dissatisfied." The patient places the stylus on the "Very Satisfied" rectangle and that item response is automatically saved. The patient moves from item to item by placing the stylus on the word "Next" that appears on the screen. The last screen states "You are now finished."

The data from the E-PDS 103 corresponding to responses to screens 103 are downloaded directly into Module 106 that converts these data records into the same predetermined format as those received from MRS 102 through scanner 104. Both of methods them responded that they were Very Satisfied with parking/availability of public transportation. Both patients' responses were formatted as a "1" (indicated very satisfied) as compared to "0" did not mark very satisfied. The data in the database are available for statistical manipulation and for inferential statistics. Preferably, the data derived from the stored PPPM information is considered statistically valid because it is derived from survey instruments, i.e. the survey questions, that are statistically-validated. and have been field tested on a human test group having a large number of patients. The patients are chosen to be a representative sample of a much larger practice population with wide variability of characteristics.

The PPPM information, in raw and digitized, form, from practices 120 are stored within the Database 124 in manner governed by database processing module 106. Database processing module 106 examines raw PPPM information to determine validity and then stores the PPPM information in a format which allows optimal use by Data Analysis processor 108. For example, all prescription information may be kept as records in one sub-database, the record including a unique patient identifier, and prescription information from a particular PPPM information set and patient identifier may be unknown, and is so identified as unknown in the record. Data Analysis processor 108 includes algorithms for processing the data. Storing PPPM information from the network of practices with the data processor enables statistically valid regional, national, and specialty comparisons to be made between different treatment practices, different levels of patient satisfaction and adherence, as well as different practice management costs.

Database section 124, for example, may contain PPPM information from multi-specialty, primary care physicians. The algorithms for processing PPPM information may contain coding to provide processed PPPM information according to age, severity of the problem, use of community resources, patient responses to their therapies, and other pertinent information Consequently, if Patient X and patient Y have Chronic Obstructive Pulmonary Disorder (COPD), the COPD information, reactions to their care, the patient's satisfaction and the practice's costs of care are provided so that the care by the respective physicians of Patient X and Patient Y, who may practice in the suburbs of Philadelphia, may be compared with one another, as well as compared with other multi-specialty, primary care physicians practicing in the city.

Next, the Data Analysis Processor 108 continually and periodically implements the specific algorithms using the PPPM information stored within the Database 124. Based on criteria defined in each algorithm, specific information contained in each record in the Database 124 of the Database Processing Module 106 is accessed by the Data Analysis Processor 108, the specific accessed data is processed, and results generated for use by each individual physician practice or other consumers of the results. The Data Analysis Processor 108 includes a data processing package that selects variables from each category of the database and analyzes the data with statistical packages (e.g., SPSS, SAS, etc) that are appropriate for the research/practice questions that have been posed.

For example, the respective physicians who treat Patient X and Patient Y may want to know the regional cost of pharmaceutical and community based therapies to their COPD patients, adherence of these patient to the prescribed regimens, and a comparison of costs to their respective practices to other practices in which pulmonologists treat COPD. Based upon criteria defined in the algorithm, specific information, such as the number and type of subspecialists in a practice is extracted from each record in the Database 124 by the Data Analysis processor 108. For example, the algorithm counts the number of times that the patient has seen the pulmonologist and the number of times that the patient has seen the generalist for COPD. The means and standard deviations of costs, adherence, and satisfaction of seeing both types of physicians are compared in multivariate studies.

The Report Generation Module 110 produces a report for use by the individual physician or the physician group. The report is the result of a process of receiving the results of data analysis from the Data Analysis Processor 108 activated when a specific algorithm is called up and implemented during the analysis process. The Report Generation Module 110 of the exemplary embodiment generates two primary types of reports, First, a periodic report which summarizes general information about a quality level of the practice during the period including, but not limited to, the number of patient responses received, a breakdown of the responses based upon the types of treatment conditions, an indication of patient satisfaction, a comparison of the satisfaction level in comparison to other similar Physician practices, and summaries regarding the progress of the classes of patients.

Second, the Report Generation Module 110 generates real time reports in response to physician queries. For example, a Physician may need information comparing the historical data concerning satisfaction of patient treatment in order for the physician to determine whether a recently implemented change in treatment regimen improves or decreases patient satisfaction. These real time reports may be queried from and received locally by the physician through a dial-up modem connection from a personal computer (PC) 122 to the Data Analysis Processor 108.

Finally, the performance of the System is monitored and tracked by the Outcomes Measurement Module 112. In the exemplary embodiment of the present invention, the Outcomes Measurement Module 112 tracks the progress of perceived quality of a physician's practice. The module compares the individual practice's and network's clinical, physician patient and cost and management outcomes with similar practices from the same region and across the nation. The outcomes module is the part of the system that can directly lead to improvements to medical practice, patient satisfaction and practice management. After receiving its first outcome report, the physician or practice can begin to compare present results of the same practice with past results. The reports can show the effect over time of decisions made to improve quality of diagnosis, treatment, practice management, and patients perceptions of and responses to practice efforts. When changes do not occur and areas of the practice remain resistant to improvement, it may be necessary to make changes to the information that is gathered by the MRS 102 or the E-PDS 103.

A further aspect of the exemplary embodiment of the Outcomes Measurement Module is tracking of responses from patients, physicians, and the practice and correlating patient diagnosis and treatment outcomes and practice costs by the data analysis processor 108 with the patient responses to particular questions included in the surveys of MRS 102 and E-PDS 103. Strong correlation between patient responses and particular treatment outcomes (e.g. a 0.80 correlation between dissatisfaction with the manner of the doctor and non-adherence to a prescription for a Beta Blocker) are used to identify 1) patients who are "at risk" of an adverse outcome, either in the overall patient's perception of care or in health outcomes and 2) aspects of a practice which require improvement.

The Survey Design and Verification Process

The System 10 preferably includes (i) a large number of enrolled physicians and practices, which may be accomplished by simplifying the enrollment process; (ii) a statistically valid survey for gathering information which is readable and easy to complete; and (iii) PPPM information which is easily collected from physicians as part of their routine in the practice. These aspects of the system 10 help to improve compliance and participation, and so the exemplary embodiment of the system 10 employs either a simple, machine readable form, the MRS Form 102, which the physician and the patient fill out as part of the consultation process, or an E-PDS 103, which a practice employee loads with some patient, disease and/or treatment data and is given by the physician to the patient during the encounter to complete. By making the form part of each patient's clinical encounter, the data are gathered on an ongoing basis that immediately records the impressions of both the physician and patient. This eliminates the possible inaccuracies and lack of validity of responses from patients who might inaccurately recall encounter data at a later time.

Another aspect of the present invention is that the survey form is designed to be completed in a very short period of time, e.g. 5 minutes. Consequently, the data gathering process adds negligible interference to the patients' treatment session, and so has no impact on the patients' satisfaction with the physicians' practice. Additionally, all survey forms that are administered are developed using rigorous reliability and validity testing techniques, as is known in the art. The step-by-step procedures for achieving reliability and validity of an assessment instrument have been identified by Nunnally, Psychometric Theory, New York, McGraw-Hill (1976) and Kline, A Handbook for Test Construction: Introduction to Psychometric Design, London, Metheun (1986) which are incorporated herein by reference.

Briefly, design of the survey format and questions proceeds according to the exemplary following steps. First, a pool of questions (items) for assessing patient satisfaction are written by individuals familiar with aspects of care, and these items fit a certain criteria, such as being valid, easily readable and easily administered, on their face for the patient population to whom they are to be administered. Second, items that are determined not to fit the criteria following testing on a small sample group (for example, less than 20 individuals) are revised or deleted and replaced with new items. Third, the group of items are then field tested on a large sample population (for example, 1000 individuals) and both physicians and patients give individual feedback for collective analysis. Appendix A lists an exemplary group of responses for this step.

Fourth, Test reliability is determined. For this step, items and related scaling factors are analyzed using correlation studies, such as factor analysis and reliability statistics through a tool such as SPSS or SAS. A total scale score is calculated, for example, a total patient satisfaction score, and corresponding total score reliabilities are calculated As is known in the art, a Cronbach's reliability score and variance score may be employed to learn if the survey's internal consistency is satisfactory and that the survey discriminates adequately. Typically, a Cronbach score of greater than 0.7 is desirable.

Fifth, norming of the survey is performed. Norming information includes means, standard deviations and similar measures regarding, for example, local, regional, national, practice specialties, and costs for the variables. The physician is supplied the norming information for their particular practice for comparison with the other portions of the practice population.

Finally, each measure, such as patient satisfaction, is correlated with other measures of the system, such as disease diagnosis and cost. For example, patient satisfaction may have a strong correlation with positive therapy results or better breathing for a COPD patient, and a strong negative correlation with long distance to their support group.

The Physician/Patient/Practice Management Information Collection Procedures

Initially, a practice 120 enrolls in the system, which includes providing information about the practice, which may be accomplished through an enrollment form. Such practice information may include practice location, number of physicians, physician's names and specialty, number of exam rooms, number of patients and other general information. Further, the enrollment may collect data which is related to patient population characteristics and costs of care delivery, such as the frequent zip-codes or geographic areas of the practice's patients, frequent billing codes (e.g. ICD-9 billing codes) and health care insurance information. Also collected may be specific cost information of the practice's business, such as the loaded costs associated with each physician, nurse and support staff; costs for the floor space of the practice, or costs of malpractice or other insurance.

Once the enrollment is complete, the practice information is stored through the enrollment processor 101 of FIG. 1 in the database 124 for use by the data analysis processor 108. Enrollment processor 101 may include a method by which occasional update forms are transmitted to practices 120 to update the enrollment information. Such process may be manual, or may be automatic through, for example, data entry via a dial-up Internet Web site. Once enrolled, the practice begins collecting PPPM information through MRS forms 102 and/or E-PDSs 103.

After enrollment, the physician's practice is instructed in the collection and PPPM information transmittal process. Shown in FIG. 1B is a flow chart of patient survey data collection instruction employed by the exemplary embodiment for a physician from a practice whose patient has been diagnosed with Chronic Obstructive Pulmonary Disorder.

First, the physician must arrange so that at least one survey is completed per week for the particular measure to be monitored. For example, if the survey addresses the practice 120, any patient's survey fulfills this requirement; if, however, the measure is for COPD, then only patients treated for COPD fulfill this requirement. Next, the physician arranges the office procedures for handling patients so that the patient is handed either MRS 102 or E-PDS 103, and necessary postage/reply envelopes if the survey is filled out by the patient at home. Arrangement of office procedures may be: 1) place MRS 102 or E-PDS 103 in patient's chart, with appropriate physician/practice information entered at this time; 2) offer survey to patient at close of patient's clinical contact, with appropriate explanation of purposes, confidentiality and instructions; 3) If patient declines to provide survey, physician's office still provides unanswered survey with physician's input and indication that patient declined for data validity purposes; and 4) the group of surveys for a specified period is then delivered to the central database of the System 10.

Figure 2A:
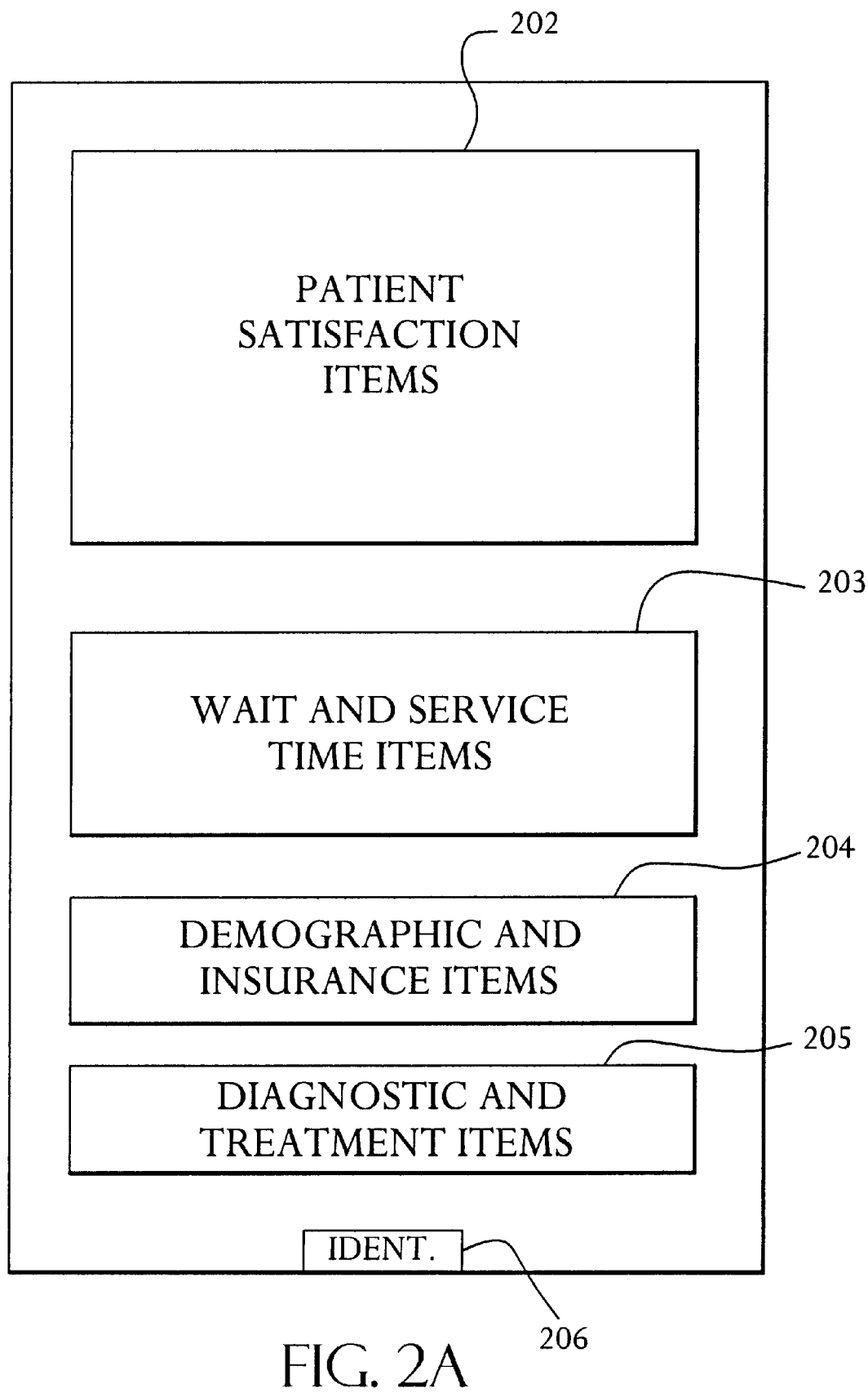
FIG. 2A illustrates the format of the machine readable survey form employed by the exemplary embodiment.

FIG. 2A illustrates the format of the MRS Form 102 according to the one embodiment of the present invention. As shown, the MRS Form 102 includes Patient Satisfaction items 202, Wait and Service Time items 203, Demographic and Insurance items 204. Diagnostic and Treatment Items 205, and Optional Identification Section 206. Optional Identity Section 206 can be used for by the physician for internal use of the practice to identify the patient and the patient's managed care provider or insurance provider. FIG. 2B illustrates the MRS form 102 used in one exemplary embodiment, and FIG. 2C illustrates an alternative form used in another exemplary embodiment.

The MRS 102 is an example of a form that can be applied to the System. Other standardized and validated instruments also would be appropriate. A listing of Psychosocial Instruments Useful in Primary Care that could alternative or additional embodiments are listed by Frank in *Tools for Primary Care Research* London: Sage Publications, 1992, pp. 229–270, which is incorporated herein by reference.

On a pre-selected day of the week in the practice 120, The MRS Form 102 is prepared with Optional Patient identifiers in section 206 and given to the physician, who can complete the Optional Identity section 206 and the Diagnostic and Treatment Items 205. For example, when Patient X completes her clinical encounter at Practice 120 (FIG. 1) her physician gives her the MRS Form 102 that has patient identifiers 206 and Diagnostic and Treatment Items 205 completed. The physician asks her to complete blocks 202 through blocks 204. A clipboard with an attached pen are provided to Patient X who returns to the reception room and fills out the appropriate blocks of MRS Form 102. She places the completed MRS in a collection box. Had she not opted to complete the MRS Form 102, she could have opted to take an addressed envelope home and mail it to the practice.

Alternatively, the E-PDS 103 (FIG. 1) is available in each practice room for patients of Practice 120 seen that day. At the end of the encounter, the physician, can respond on the E-PDS 103 to the Optional Identity section 206 using the identity code that is affixed to the bottom of the E-PDS. The physician may also provide the Diagnostic and Treatment Items 205 by touching pre-specified bubbles or rectangles with the stylus. For example, when Patient Y completes his clinical encounter at Practice 130 (FIG. 1,) the physician gives him the E-PDS 103 and asks him to participate in this office's attempt to improve patient care. The patient agrees to participate and the physician touches the word "accept" on the screen of E-PDS 103 with the stylus. Had Patient Y not agreed, the physician would have touched the word decline and the device would have reset to the physician's identification number. Patient Y reads the screen of the E-PDS that now says "Welcome to the System" and "Start". Patient Y touches the word "Start" with the stylus and responds to all screens by touching the corresponding answer to each item and then touching "Next." At the completion of the survey, E-PDS 103 indicates that the survey is complete to patient Y and that the E-PDS 103 should be returned to the nurse or receptionist.

The survey items included on the MRS 102 and the E-PDS 103 have been carefully chosen to return the maximum amount of data, with a minimal requirement of effort by the patient filling out the form. The items relate to certain clinical information and overall satisfaction of the patient with respect to the physicians' diagnosis and the prescribed regimens as well as to selected practice variables and to the treatment session in general. Such questions of patient satisfaction include, but are not limited to, the areas listed in Table 1A, and questions related to time of the visit are listed in Table 1B.

TABLE 1A

| Number | Question |
| --- | --- |
| 1. | Availability of convenient parking/public transportation |
| 2. | Availability of convenient appointment |
| 3. | Courtesy of reception at check in. |
| 4. | Comfort of the waiting area. |
| 5. | Information provided about my medical condition. |
| 6. | Accessibility of office by telephone |
| 7. | Feeling about recommending this office to others |
| 8. | Satisfaction with primary insurance |
| 9. | Information provided about my insurance by office staff |
| 10. | Personal manner of the physician. |
| 11 | Are you visiting the physician for the first time? |
| 12 | How long was your total visit time. |
| 13 | Did you see your doctor at the scheduled time? |

TABLE 1B

| Number | Question |
| --- | --- |
| 1. | How long did you wait to see the physician? |
| 2. | How much time did you spend with physician's nurse or assistant? |
| 3. | How much time did you spend with your physician? |
| 4. | Was the wait acceptable? |
| 5. | Was the time spent with the nurse or assistant useful? |
| 6. | Was the time spent with the physician useful? |

As shown in FIGS. 2A through FIG. 2C, the MRS form 102 with patient satisfaction survey items does not necessarily include the patient's identity, so there is no danger of a patient's confidential information being inadvertently released. For programs or clinical trials the MRS form 102 may include an assigned random number or similar identifier corresponding to a patient which may be known to the physician only to maintain the patient's confidentiality. Also, an automatic time and date stamp may be affixed to the MRS 102.

In order to be easily answered, machine readable, and allow variability of response, the MRS survey 102 and the E-PDS 103 version of the survey are designed with a multiple choice format. The information contained on the form is scanned and electronically input to the Database 124, which can be, for example, a Microsoft SQL relational database, using a commercially available program, such as Microsoft Access, for later analysis. Each E-PDS 103 is downloaded directly into the Database 124 as subsequently described.

The Patient Management Assistant Data Collection

As previously described, the system 10 may include a personal disease management process, described subsequently, which also collects patient survey information related to a treatment regimen prescribed by the physician. The PDMA 105 receives a treatment profile from the host 107. The treatment profile may be a pre-defined treatment regimen for a particular disease or health management program which is tailored by the physician to a particular patient's treatment regimen. Such tailoring may be accomplished by bringing the treatment profile up on the screen of the host 107 and the physician, nurse or other attendant enters, for example, prescription information and dosage, particular times to take medication or other aspects of treatment. The treatment profile may also contain a help file associated with a disease management program. The host then downloads the treatment profile to the PDMA 105. In an alternative embodiment, the treatment profiles are contained in a remote database (not shown) and downloaded to the host from the remote location for periodic updates.

Using a scheduling and reminder function of a hand-held computer unit, which may be a modified version of the E-PDS 103, the PDMA 105 periodically activates and reminds the patient that an event associated with a treatment regimen must take place. At this time, the PDMA prompts the user for survey information relating to the treatment, satisfaction with the treatment, or whether other medications, prescribed or over the counter, may be being taken. The patient may be able to get information related to the treatment program from the help file, such as, for example, whether a dosage can be reduced, increased, or taken with certain over-the-counter medications. The patient then may periodically download the data collected by the PDMA through a dial-up link, or send the PDMA 107 to the physician's or system provider's office.

In an alternative embodiment, the database 124 of FIG. 1 may maintain records of each PDMA 107 for each patient, and the host may be linked to the database 106 in real-time as a PDMA is programmed. Consequently, when a physician programs a treatment profile of a PDMA 107 for a specific disease treatment regimen, a search processor (not shown) may search the database 106 for other treatment regimens for the same patient. If a match occurs, the searching processor may determine if a potential problem or contraindication exists, and the physician is notified to modify the planned treatment regimen of the treatment profile.

The patient data collected by the PDMA 107 may be used as part of a clinical trial, in addition to collecting patient/physician data. The PDMA 107 may also contain disease specific educational games, clinical trial access and information on advocacy or other support groups.

The Physician/Patient Database Population and Management

As mentioned previously, the raw data representing PPPM information from the machine readable MRS Form 102 and E-PDS is stored in a database format; however, the information is subject to exception handling and other filtering to discard "bad" data, and is then processed. Exception handling can be accomplished, for example, by human intervention if the MRS Form 102 has been incorrectly filled out, by eliminating responses that show response set (i.e., that the respondent answers all items in the say way no matter how they are presented) or that are vastly different from the remaining responses, or that have large mounts of missing data. Once the raw data has been "smoothed" based upon a predetermined criteria, the information is stored in a database.

FIGS. 3A–3C illustrates an exemplary database file layout used in coding data for one embodiment of the present invention. The final column codes the data from the MRS 102 completed by patient X having COPD. The database program format of the exemplary embodiment is SQL. As shown, each patient response from a MRS Form 102 is summarized as one ASCII record. Each field is represented by ASCII printable codes, and each field is separated by tab characters. Records are terminated by carriage return and linefeed codes.

The Physician/Patient Information Data Analysis

The Data Analysis Processor 108 can perform various forms of analysis on the records stored within the Database 124. The simplest form of analysis is the production of descriptive statistics for the data. To calculate a mean total score for satisfaction, for example, all of the individual responses are summed and then divided by the total number of satisfaction items. Similarly, the standard deviations, skew, etc. of the items can be calculated for each MRS Form 102 and E-PDS 103. These descriptive statistics are described in standard texts such as Mehrens and Lehman, "Basic principles of measurement in *Measurement and evaluation in education and psychology*. New York: Holt Rinehart and Winston, 1973, which is incorporated herein by reference. However, more complex analysis can be performed on the information contained in Database 124.

Figure 4:
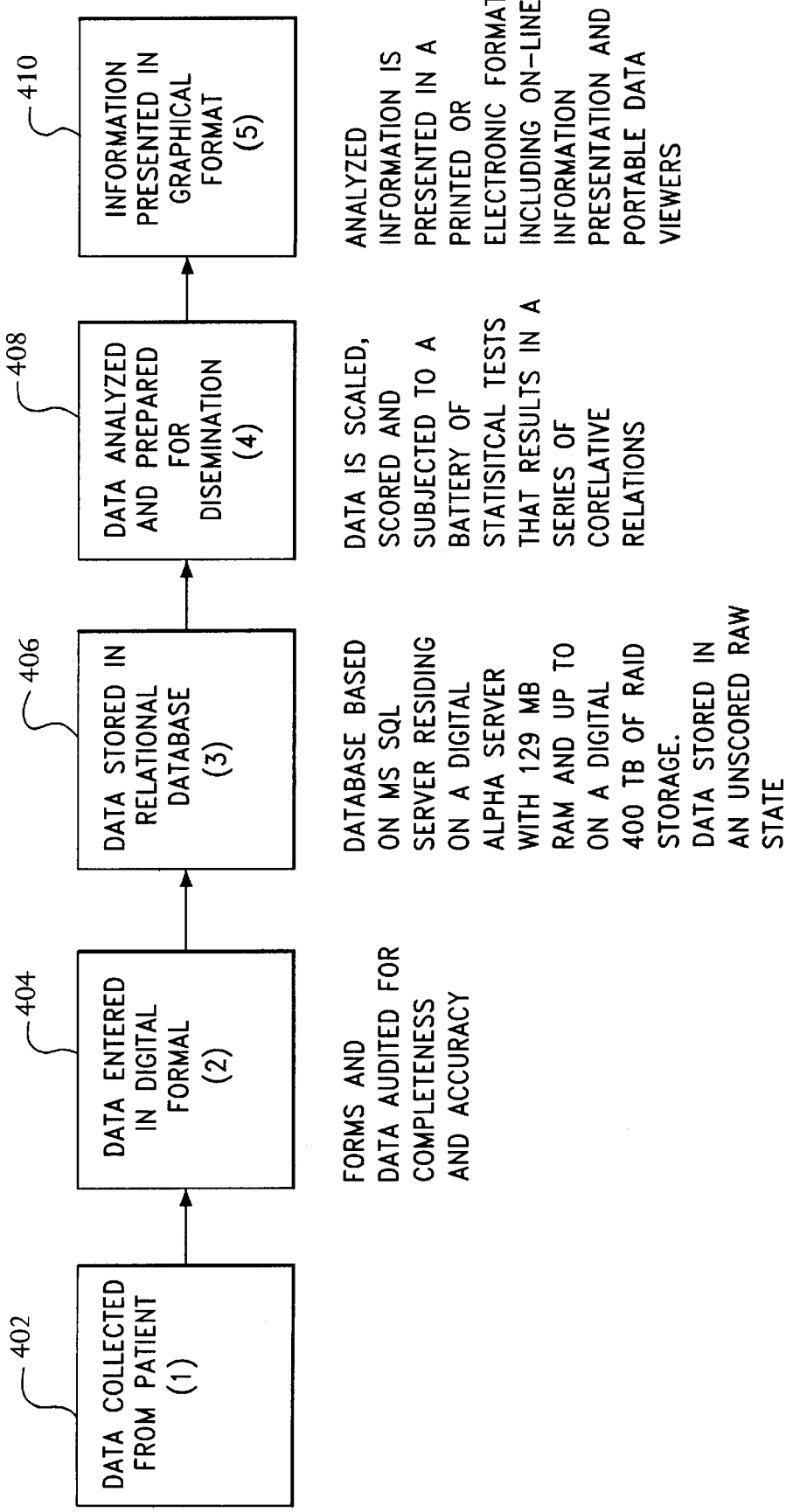
FIG. 4 illustrates the high-level system description for the method of one exemplary embodiment of the present invention including database data analysis and presentation as part of a report to the practice.

FIG. 4 illustrates the high level system description for the method of the exemplary embodiment of the System, including database data analysis and presentation. As shown in FIG. 4, the System collects physician and patient data from the MRS Form 102 or E-PDS 103 of FIG. 1 at step 402.

At step 404, the system receives the physician and patient data and audits the data for completeness and accuracy. This is a "simple" audit to see if all questions are answered, multiple responses were made to one question, patient really read and answered questions properly rather than randomly entered the values, or the entry values correspond properly with one another (e.g. female patient, but diagnosis or other questions indicate a male patient). If entries are found to be defective, the entry is tagged as defective, or set to "no response." However, all survey responses are maintained for statistically validating the aggregate PPPM information of all responses. As discussed previously, such audit may be manual, or may be automated based on a particular criteria. At step 406, the formatted physician and patient data is stored in the relational Database 124 of FIG. 1.

The Data Analysis Processor 108 of FIG. 1 analyzes the physician and patient data and creates results in a predetermined format at step 408. At step 408, the physician and patient data is scaled, scored and subjected to selected statistical tests that result in a series of correlative relations. Finally, at step 410, the results of the selected statistical tests are displayed in a graphical format.

For the following discussion, an example visit according to the process of FIG. 4 is described with a white female patient previously diagnosed with COPD. The patient, Patient RB, visits the practice as a result of a bronchial asthma attack. Upon scheduling the visit, practice office staff have added a MRS 102 or E-PDS to the patients chart or other form of file, and the patient's codified data regarding previous diagnosis, prescription medication Activities of Daily Living and therapeutic regimen have been entered into the MRS 102 or E-PDS 103.

When the physician meets Patient RB, he ascertains changes in health status, particular symptoms such as ½ cup yellow-green sputum from a wheezy cough, ADL information and adherence to the therapeutic regimen that includes theophylline, vanceril spray, breathing exercises and support group participation. The physician prescribes ampicillin for the cough. The physician is interested in a comparison between his COPD patients and other like patients on a regional and national basis. Therefore, as described by step 402 of FIG. 4, the physician completes the diagnostic (exacerbation of COPD) and therapeutic items (ampicillin) of the survey, and is interested in COPD as part of the family of diseases with high morbidity and mortality statistics. According to step 404, Patient RB completes the survey of MRS 102 or E-PDS 103, and enters "very satisfied" to all questions, giving a raw score of 50. Patient SM, a male patient of another practice, chooses "dissatisfied" five times and "satisfied" five times to give a raw score of 30.

According to step 406 of FIG. 4, the survey information items are transmitted to the database processing module 106 of FIG. 1, checked for accuracy and completeness, and stored into a relational database, database 124, in an unscored state by code values (e.g. "COPD" is assigned code value "300"). If the physician has a poor response rate to the survey process, an indication is sent to the physician.

Next, at step 408, the survey information may be analyzed and prepared for dissemination. Items are either single variables, such as patient sex or COPD, or belong to a particular scale, with each scale having a maximum total score of the number of items multiplied by the highest score per item. Consequently, the items may then be compared based on numeric representation. For the example, a mean average of patient satisfaction for 100 patients like Patient RB with COPD for the particular physician may be 4.5, with a standard deviation of 0.2, with a regional average of 3.5 and regional standard deviation of 0.5. These values show that, on average, the patients with COPD are between satisfied and very satisfied, and the particular physician's practice is statistically "better" than average. Analysis of variance may be conducted to determine a relationship between sex and satisfaction, with a F statistic and probability of less than 0.05 would indicate that these items are related.

Also at step 408, correlation statistics may be calculated to show relatedness among the variables of the database 124. For example, Patient RB may have a severity score of 3 (moderately serious) an a 1–5 scale. Patient SM has a severity score of 5. A correlation of 0.85 (p less than 0.005) between severity and cost shows that the severity score is highly related to cost, meaning that patient SM may require greater cost to deliver care. Comparisons between practices for the given data may also be shown such as the number of physicians decreases the correlation between severity and cost to 0.70.

Finally, at step 410, the summarized data is presented in a format which may be easily read.

Figure 5:
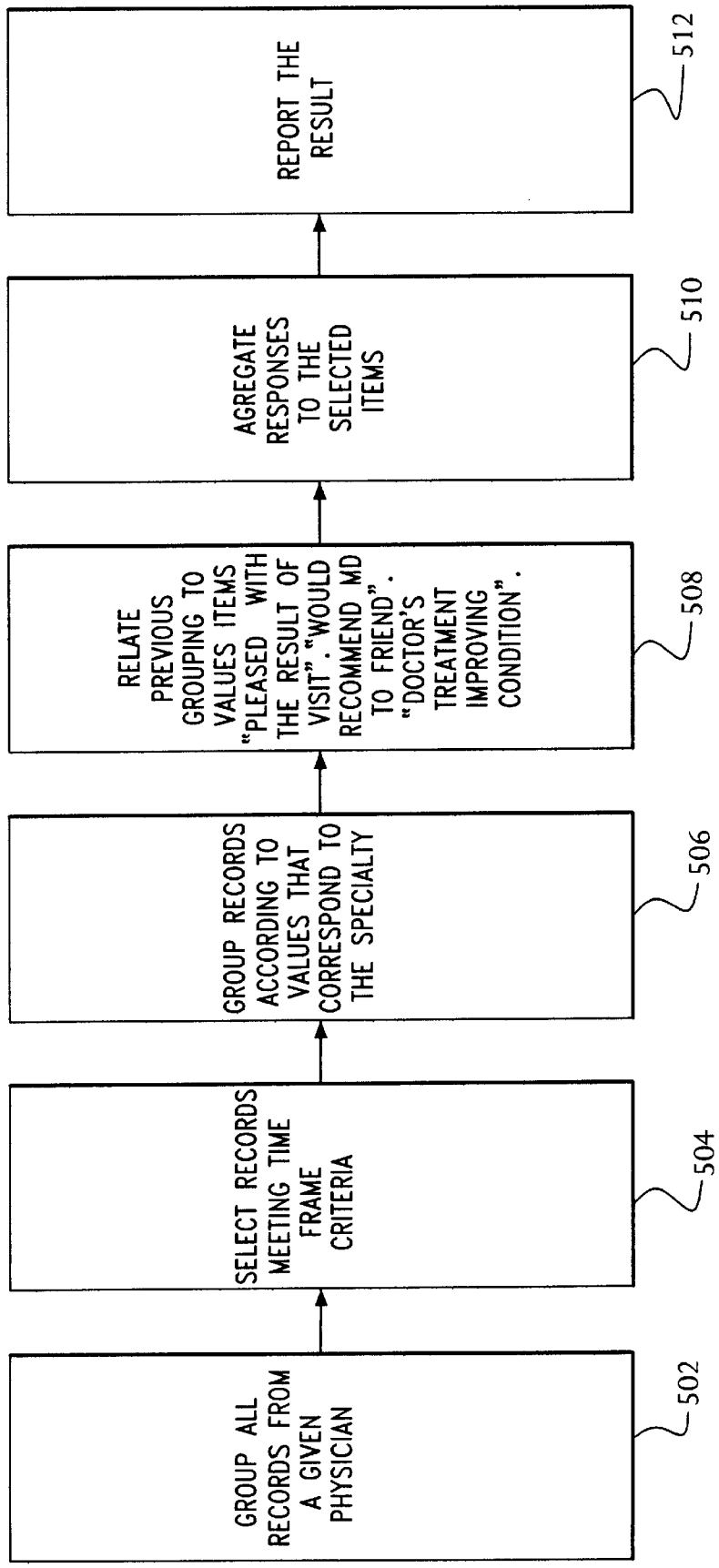
FIG. 5 is a flow chart showing an exemplary algorithm used to process and display a relationship between availability of a convenient appointment and feeling about recommending this physician for one exemplary embodiment of the present invention.

The portion of step 408 of FIG. 4 which subjects the data to selected statistical tests is shown by way of an example. FIG. 5 is a flow chart showing the algorithm used to process and display a relationship between physician manner and recorded satisfaction as used, for example, in one exemplary embodiment of the present invention.

Referring to FIG. 5, the extraction from the System 10 of specific information with the periodic reports or dial up inquiry is performed by report generation process 110 of FIG. 1. The algorithms of the Data Analysis Processor 108 selects a group of all records from a given physician and extract these records from the Database 124 at step 502. Next, at step 504, only those records meeting a predetermined time period are retained for further analysis. For example, RB's physician in Practice 120 decides to determine the level of adherence (1.00–3.00) to their medications of patients with a severity pulmonary disorder rating of >4. on a scale of 1.00 to 5.00 for COPD At step 506, the records are grouped according to the specialty type and patient problem type (i.e., in this case, pulmonary patients in general practice.)

At step 508, the grouped records are then related to values corresponding to the degree of therapy adherence.

At step 510 the responses in each category are counted and tabulated. Mean values, scaled mean values and statistical confidence levels are generated as described previously.

Finally, at step 512, the results are reported.

Figure 6:
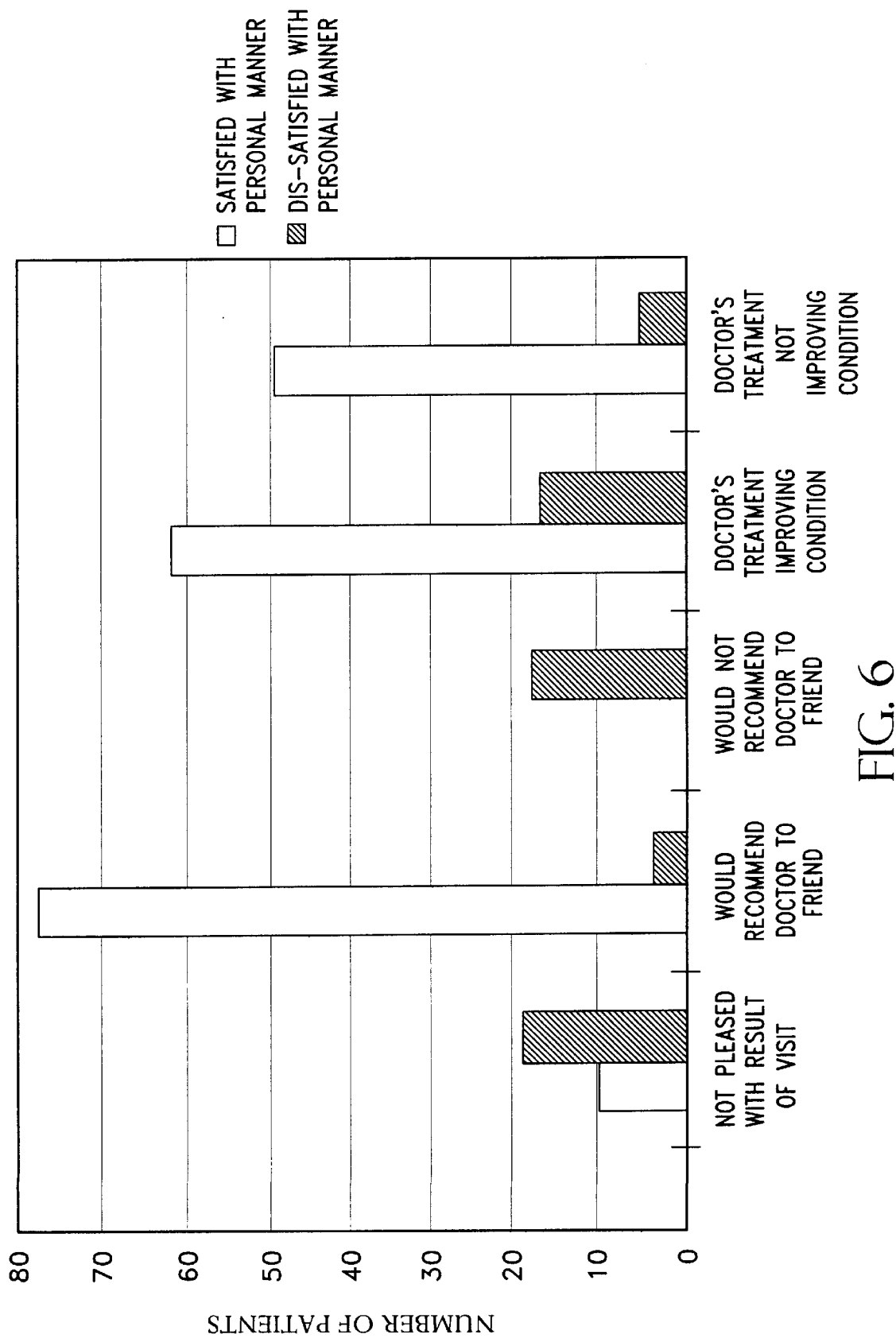
FIG. 6 illustrates the exemplary output display format for the exemplary algorithm of FIG. 5.

FIG. 6 illustrates the exemplary output display format of step 410 of FIG. 4 for the exemplary algorithm of FIG. 5. As shown in FIG. 6, the impact of a physician's manner can be related to various values of patient satisfaction. The vertical axis represents total number of patients responding, and the horizontal axis gives the patient satisfaction variables related to a physician's manner. Since recommendations effect total practice income, the relative effect of physician's manner to cost to the practice, for example, can be determined. First, survey items are correlated to a particular measure under study, such as physician's manner.

FIG. 6 gives a pictorial example of how values for groups of conceptually related physician variables may then be displayed together. From this pictorial comparison, hypotheses may be put forth concerning relationships between, for example, physician/patient data, outcomes data and cost data. For example, if the group of patient satisfaction variables for physician manner collectively show that a poor physician manner relates to poor adherence to therapeutic regimen, then the physician may attempt to improve patient responses to one or more of the variables related to physician's manner. The process of identifying trends and changes in response for hypothesis testing are known in the art, and may be found in, for example, in Norton et al., Primary Care Research: Traditional and Innovative Approaches, Research Methods for Primary Care, Vol. 1, Sage Publications, London, (1991), which is incorporated herein by reference.

The primary parameters measured, validated and reported in the exemplary embodiment of the present invention are given in Table 2.

TABLE 2

| Number | Parameter |
|---|---|
| 1. | Satisfaction of patients regarding manner of treatment and its outcome. |
| 2. | Relationship of cost of treatment to effectiveness of treatment. |
| 3. | Effectiveness of physician's treatments compared with those of his peers. |
| 4. | Relationship of treatment to customary treatment practice. |
| 5. | The amount of time taken for a particular treatment. |

The identification of this information and the order of importance of the information given on Table 2 have been determined empirically through past experiences of the inventors.

Figure 7:
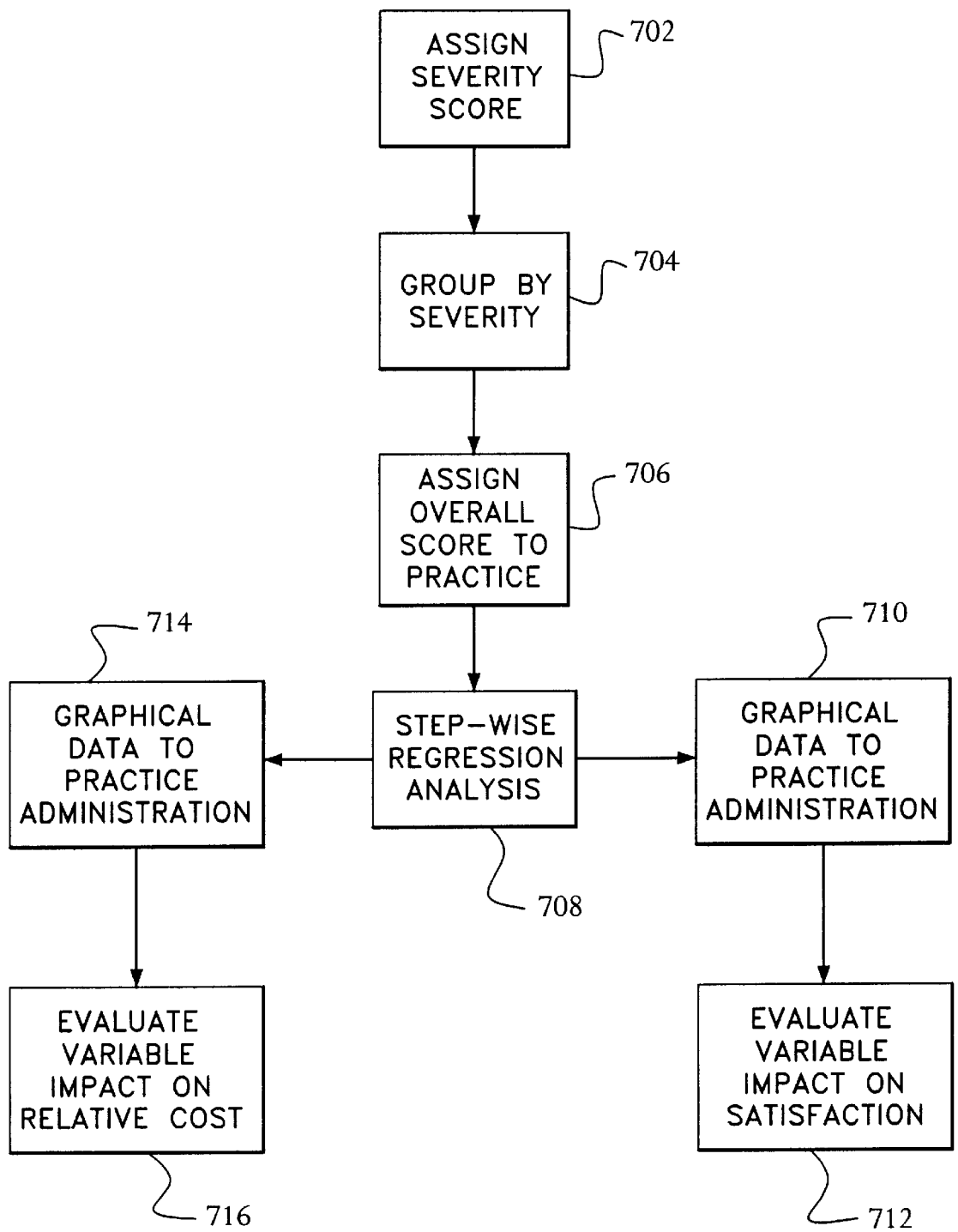
FIG. 7 is a flow chart of an exemplary data analysis sequence of the Data Analysis Processor of FIG. 5.

FIG. 7 is a flow chart of one exemplary general data analysis technique of the Data Analysis Processor 108 of FIG. 1 as used, for example, in the step 408 of FIG. 4. Beginning at step 702, individual respondents are assigned a severity score based on a summative co-morbidity scale. Respondents are grouped by severity in step 704, and an overall score is assigned to the practice at step 706. At step 708, a multiple regression statistical analysis is conducted to describe the relationship between numeric measurements of patients with pulmonary problems and their measured outcomes, including adherence. At step 710, a graphical report is generated of the results of step 708 which summarizes information used by physicians and practitioners to evaluate effect of a variable on patient behavior (e.g., adherence.). The graphical report allows physicians or other practitioners to evaluate the impact of their objectively measured performance (e.g. adherence) on the self reported satisfaction of stratified sub-populations of their patients at step 712. Such report is shown in FIG. 6

At step 714, a graphical report is generated of the results of step 708 which summarizes Practice Management and Cost information used by practice administrators and professional staff to evaluate effect of a variable on cost at step 716. The graphical report demonstrates the relationship of satisfaction on objective measures of cost and administrative functioning (e.g. the relationship of satisfaction results to future referrals or return visits) and demonstrates the ranking of the practice or individual within the community of contributor practices of system 10 in terms of mean patient disease severity, mean satisfaction and standardized cost.

In a further embodiment of the present invention, the enrollment process of a practice includes receiving costs associated with the practice, such as a loaded cost of a physician's time, a loaded cost of a nurses's time, etc. Since patients provide information as to length of time spent with different individuals within the practice, the cost of delivering care may be tabulated. Further, insurance information, which may be provided from a separate source, may be compared with means and variances of the practice's costs to provide care or treat certain types of diseases for certain patients. Further, median income information of patients and median practice information of other practices having the same specialties in the local or regional area may be used by practices giving elective care (plastic surgery, for example) to determine prices for certain healthcare options.

The Physician Report Generation Module

Once the data is available, the data is processed to provide periodic reporting by the Report Generation Module 110 of various types of information to each physician which the physician may use, for example, to improve the quality of the practice by identifying problem areas; identify new practice areas; or use during discussions defining the relationship between the managed care provider and the physician. Previously, with respect to the exemplary report of FIG. 6, a pictorial example of how values for groups of conceptually related physician variables may then be displayed together. These groups of conceptually related physician variables may be termed "domains" and given in periodic reports to track improvement.

The reporting process of the exemplary embodiment of the present invention includes two aspects: a periodic printed report, and a real time availability of data to the physician, giving performance based upon specific physician queries. As noted earlier, Appendix B further illustrates reporting options for the periodic printed report of the reporting process of the exemplary embodiment of the present invention.

Figure 9A:
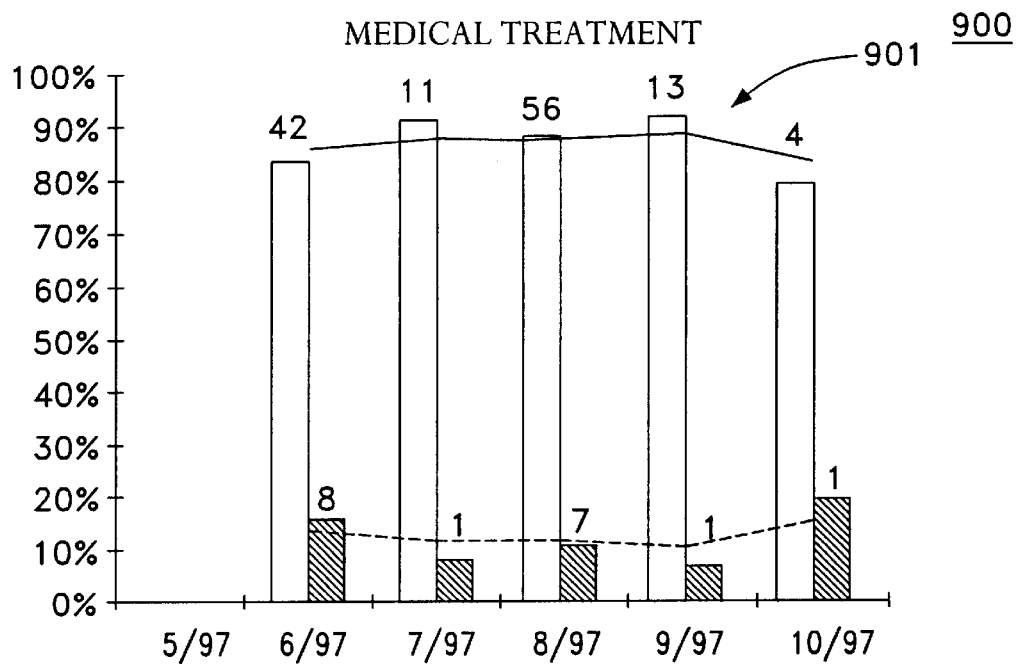
FIG. 9A is an exemplary periodic printed report of the first aspect of the reporting process by medical treatment domain of one embodiment of the present invention.
Figure 9B:
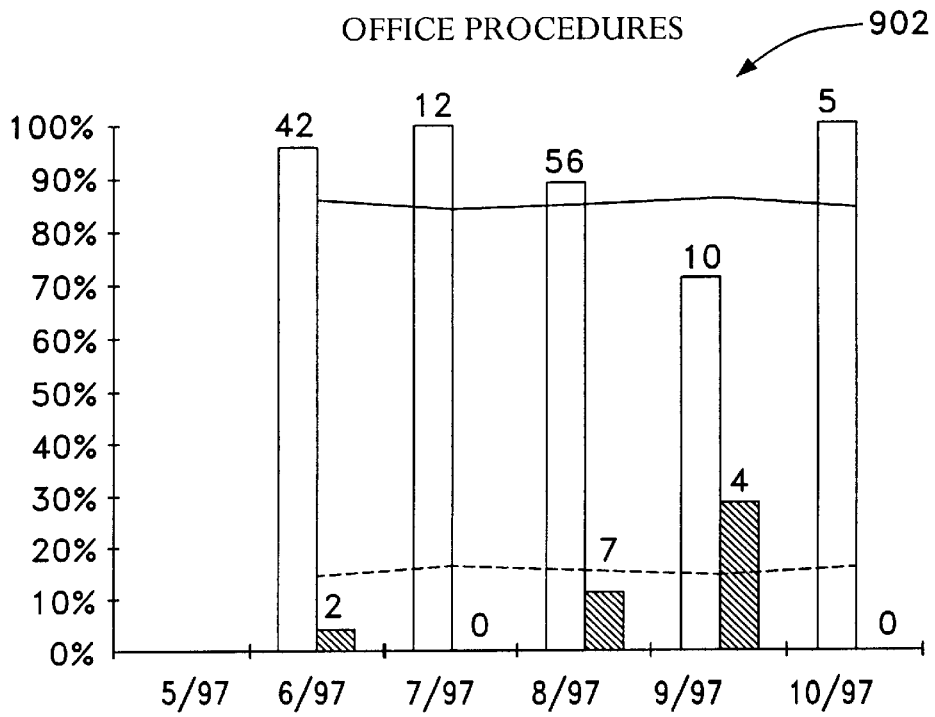
FIG. 9B is an exemplary periodic printed report of the first aspect of the reporting process by office procedures domain of one embodiment of the present invention.
Figure 9C:
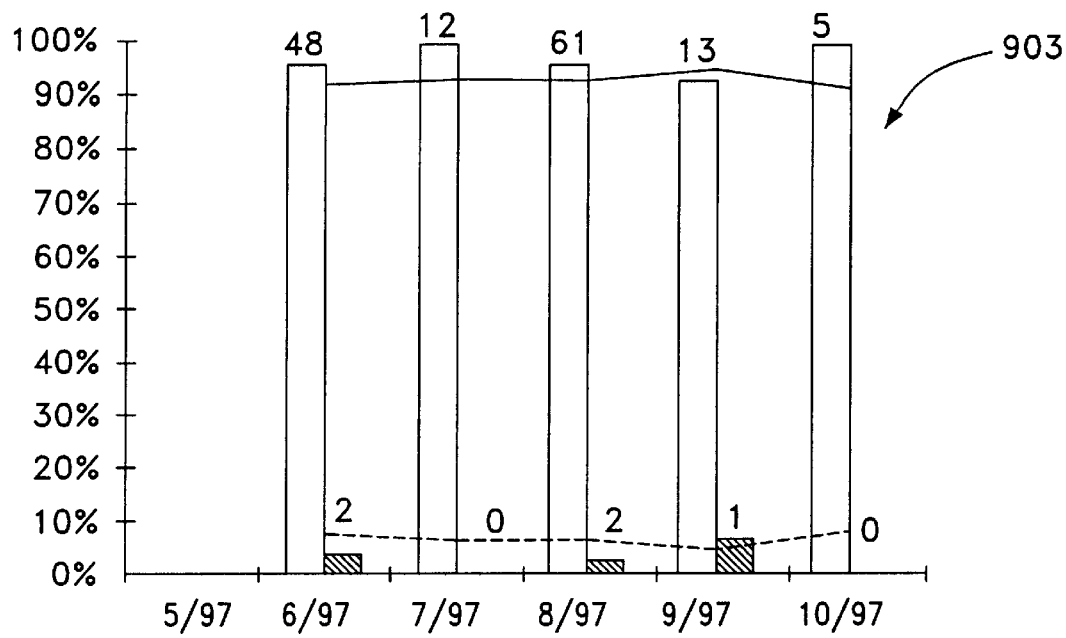
FIG. 9C is an exemplary periodic printed report of the first aspect of the reporting process by office recommendation domain of one embodiment of the present invention.
Figure 9D:
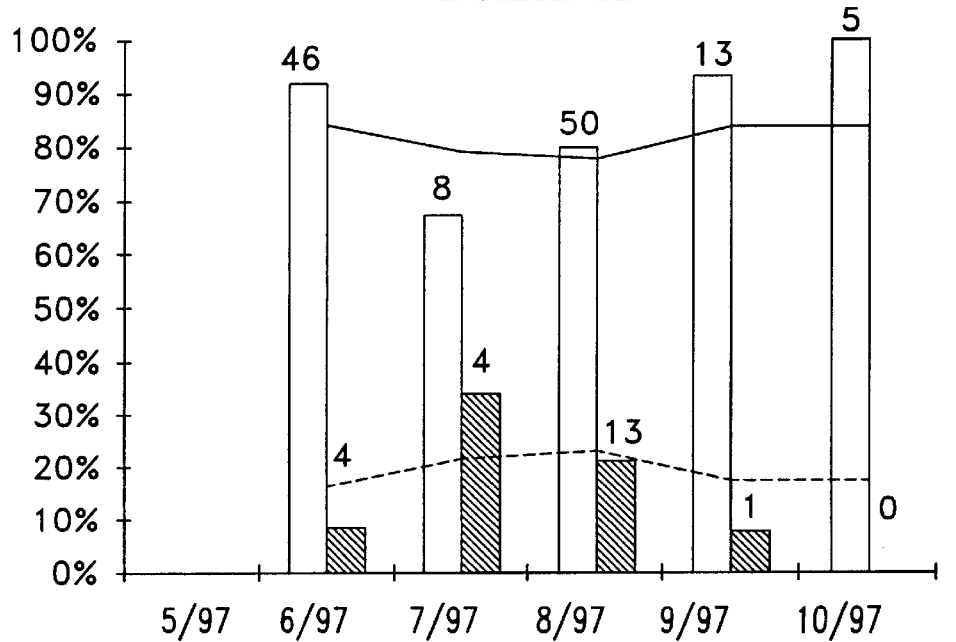
FIG. 9D is an exemplary periodic printed report of the first aspect of the reporting process by insurance domain of one embodiment of the present invention.

FIGS. 9A–9D show domains of an exemplary periodic printed report 900 of the first aspect of the reporting process by domain of one embodiment of the present invention. FIG. 9A is an exemplary periodic printed report of the first aspect of the reporting process by medical treatment domain of one embodiment of the present invention. FIG. 9B is an exemplary periodic printed report of the first aspect of the reporting process by office procedures domain of one embodiment of the present invention. FIG. 9C is an exemplary periodic printed report of the first aspect of the reporting process by office recommendation domain of one embodiment of the present invention. FIG. 9D is an exemplary periodic printed report of the first aspect of the reporting process by insurance domain of one embodiment of the present invention.

The exemplary report includes domain information regarding the illustrated areas of patient satisfaction for the major aspects of a particular practice: 1) perceived quality of medical treatment domain 901, 2) perceived quality of practice office procedures domain 902, 3) would the patients tend to recommend the practice 903, and 4) perceived quality of insurance coverage for healthcare given by the office.

In another embodiment of the present invention the illustrated areas of patient satisfaction are given for the practice as compared to others participating in the program. In addition, the exemplary report gives a summary of the frequency of prescribed medications and summary reports of patient satisfaction with prescribed medications. The exemplary report also includes a reminder for the physician to continue to submit MRS Forms 102 on a regular basis. As capable by one skilled in the art, the form and content of such a report can be varied and still remain within the spirit of the invention.

The second aspect of the reporting process is a dial-up or real time provider of analyzed database information. For an exemplary implementation, a PC having a "forms" format in, for example, a Windows environment can receive information in fields corresponding to the illustrated fields shown in the periodic printed report for immediate presentation. In addition, for the dial-up connection, the physician can query for particular information relating to physician defined variables: for example, the physician can define particular time periods, medications, or satisfaction levels for particular treatment regimens in particular geographic areas.

The E-PDS System

As previously described, an alternative embodiment of the present invention employs an electronic handheld computer to electronically prompt for and receive survey data, the E-PDS 103. This alternative embodiment may also employ a host device to collect more comprehensive physician diagnosis information. During a treatment session at the physician practice location 120, physicians and patients enter survey data into the E-PDS 103 with specific information relating to the treatment session ("Physician/Patient Information"). Prior to use by a patient, the electronic forms to be filled out by each patient are identified and retrieved from the Forms Library 112, and corresponding patient identification information (PID) is determined and registered in the Data Analysis Processor 108. The forms and PIDs are downloaded to the E-PDS 102 through E-PDS Interface 114.

Figure 10:
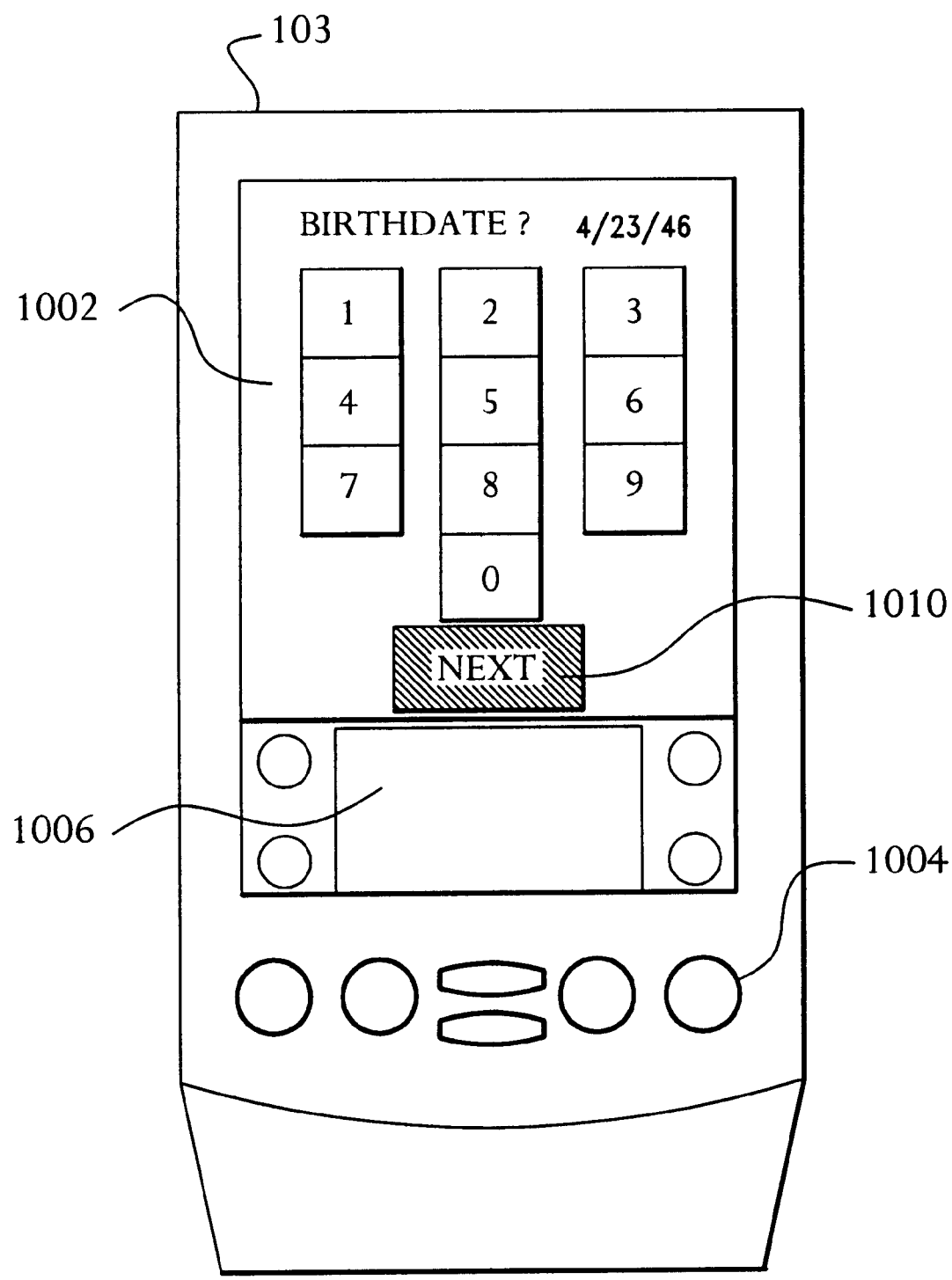
FIG. 10 illustrates the electronic patient data collection system with an electronic survey form as used in the exemplary embodiment.

The screen interface of E-PDS 103 is shown in more detail in FIG. 10, and includes a touch screen 1002 for the user to enter data, a system menu control 1004 for selecting the particular E-PDS function, and a display section 1006 for displaying the particular electronic form survey questions. The E-PDS 103 also receives responses by the patient indicating satisfaction with various aspects of the treatment session when the patient touches the corresponding part of the screen as shown in the response 1010. The user sequentially enters responses to each question section until the electronic form is filled out, and then the patient returns the E-PDS 103 to the desk. An example of a patient user interface of the E-PDS 103 is shown in FIGS. 11A and 11B. FIG. 11A illustrates a patient user interface of the electronic patient data collection system shown in FIG. 10 having numeric keypad entry in which a user is prompted to answer a survey question. FIG. 11B illustrates a patient user interface of the electronic patient data collection system shown in FIG. 10 having numeric keypad entry in which a response is entered and a user is prompted to go to the next question. A physician's interface on host device 107 of FIG. 1 is illustrated in FIG. 12, and the form section items are as described previously with respect to the MRS form 102.

Once the form displayed in the E-PDS 102 is completed, the information corresponding to the form is downloaded into the host 104 through E-PDS interface 114, and provides the Physician/Patient information to the Database Processing Module 106. The following describes an exemplary embodiment of the E-PDS 103.

Figure 8:
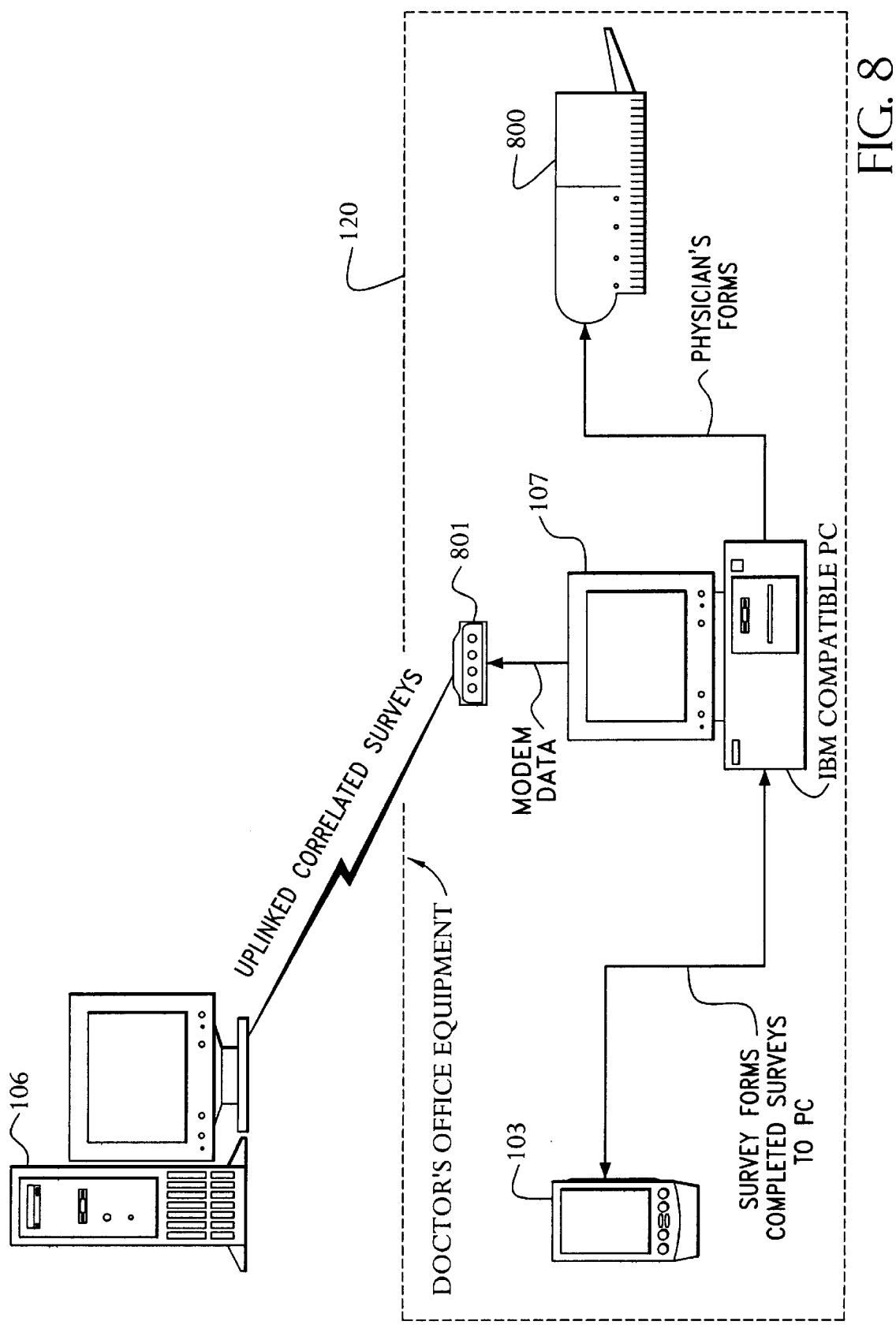
FIG. 8 illustrates a typical configuration of electronic survey data collection in a physician's practice for an exemplary embodiment of the present invention.

Referring to FIG. 8, host device 107 may be implemented in a personal computer (PC), such as an IBM™ compatible with a Pentium™ processor, and E-PDS 103 may be implemented on a personal hand-held computer organizer, which may be a PalmPilot™ available from 3COM, Incorporated. An exemplary E-PDS 103 includes a survey, called a patient satisfaction form which may have 25 patient questions and 12 questions of the host device 107, a correlation number entry up to, for example, four digits, and a date and time stamp which is recorded by the pilot. FIG. 8 illustrates a typical configuration of electronic survey data collection in a physician's practice 120 for an exemplary embodiment of the present invention. The host device 107 downloads forms and receives completed survey information from E-PDS 103, is connected to a database processor 106 to provide uplinked, correlated survey, or PPPM, information, and is connected to optional printer 800 to print reports from the report generation module 110 of FIG. 1. As illustrated by FIG. 8, uplink information is provided from host 107 to database processor 106 through a dial-up access employing modem 801.

Host device 107 may include three possible interface screens: an administration menu, a physician data screen, and a correlation menu. The administration menu contains commands that allow a user to install a survey form onto an E-PDS, print physician forms and enter physician data, correlate and update survey data, and send the data to a remote database processor. The physician data screen allows the physician or nurse to enter physician data which may be a patient number (Patient ID), gender, initial visit or follow-up visit, data and time, three diagnoses, three medications, an insurance plan, an office or practice identification (Office ID) and Physician ID. The correlation screen shows unmatched patient data from a completed survey form, allows modification of patient ID of physician data, allows creation of new physician data, and deletion of unmatched physician data.

The host device 107 numbers (batch number) and tracks each set of survey data uploaded from E-PDSs and transmitted to a remote database processor 106 at the end of a collection period. Each survey is given a sequential patient ID number (Patient Number) up to four digits which is reset to 1 after each upload to the database processor 106. Physician diagnosis forms may be printed by the host device 107 and may contain both the Batch Number and Patient Number. Prior to giving the patient the E-PDS, each printed form is then attached to the patient's file for the physician to complete during the patient's visit. Office staff enter the physician's information into the host, and download the survey form into the E-PDS 103 with the Patient Number correlated to physician's diagnosis. Using a hot-sync capability, the E-PDS's forms are downloaded to E-PDS and survey data collected from the E-PDS by the host device 107 by placing the E-PDS on a communication interface to the host 107, called a "cradle."

When the correlate functions are run, survey data is checked to ensure that no duplicate Patient Number entries are received from different E-PDSs. If a duplicate or missing patient number is found, these are provided through a screen on the host to an operator (nurse, receptionist, etc.) The operator may then correct or provide the correct patient number, possibly by going through the daily appointment schedule and correlating data present (e.g. male/female, purpose of visit, time of visit, and time/date-stamp) to known information. If duplicate entries are found, one method would be to accept either the older or the newer data and delete the other survey data. Next, the survey data and physician (diagnosis) records are correlated using Patient Number. Two errors are possible: physician data and no survey data, or survey data and no physician data. In the first case, the data may be deleted or transmitted to the database process; in the second case the operator may try to match the survey record with a patient, allowing the physician to re-enter the physician diagnosis data.

Finally, the host device assigns a batch number to the correlated survey and physician data, and uploads the information to the database processor 106 as a Batch file with corresponding Batch number. The batch number is then incremented for the next group of PPPM information.

Figure 13:
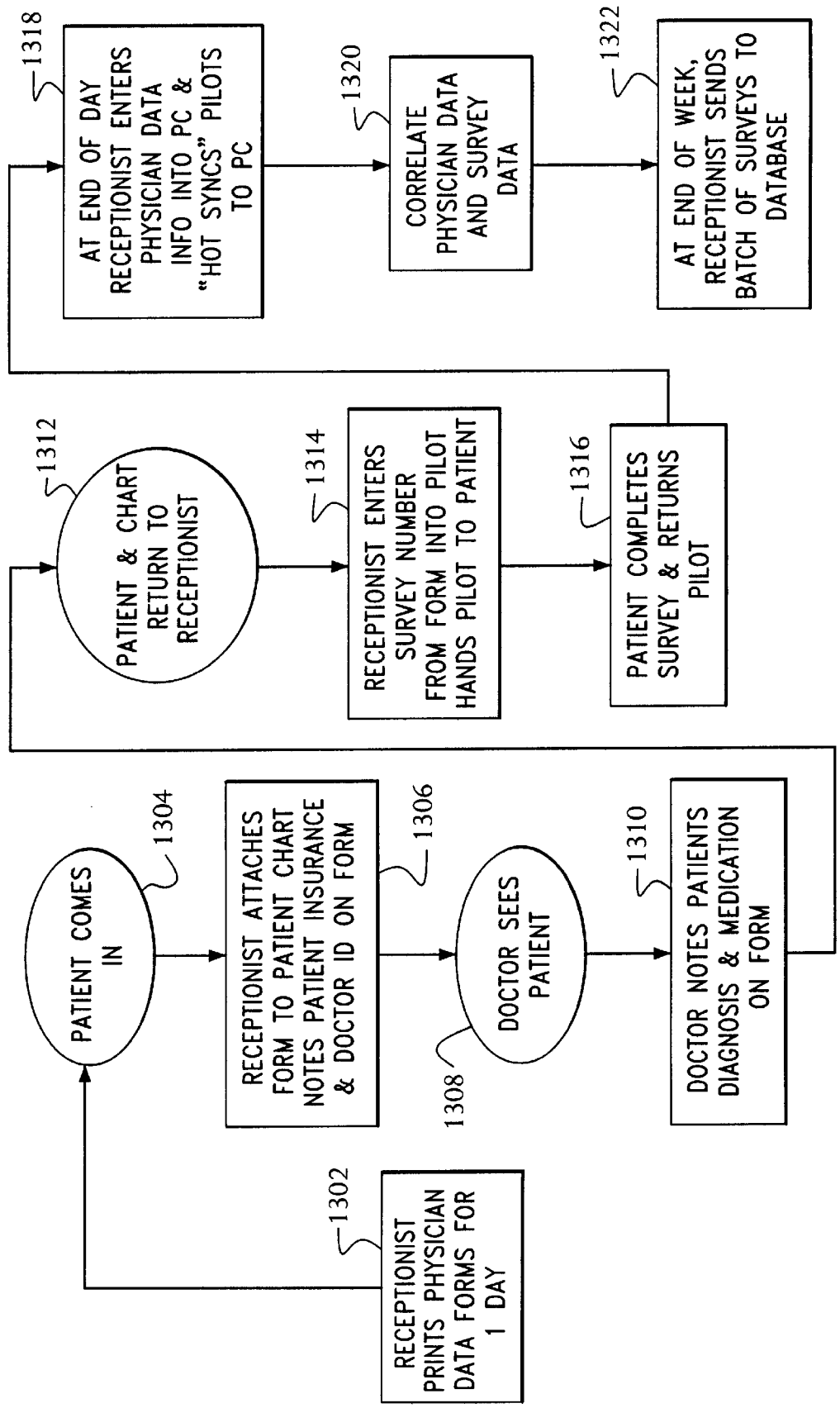
FIG. 13 illustrates an exemplary process flow followed by a practice to collect survey data with the exemplary embodiment of FIG. 8.

FIG. 13 illustrates an exemplary process flow followed by a practice 120 to collect survey data with the exemplary embodiment of FIG. 8. First, at step 1302, the receptionist prints physician diagnosis data (PDD) forms for the day. Next, at step 1304, the patient for whom a form is printed enters the office. At step 1306, the receptionist attaches the PDD form to the patients chart, noting patient insurance and physician ID information on the form.

Then, at step 1308, the patient has a clinical encounter with the physician, and the physician enters patient's diagnosis and medication on the PDD form at step 1310. The patient and the chart are returned to the receptionist at step 1312, at which point the receptionist enters the survey number, downloads the patient survey form into the E-PDS and gives the E-PDS to the patient at step 1314. The patient completes the survey at step 1316, returning the E-PDS to the receptionist.

During the day, the E-PDS may collect up to a predetermined number of sets of patient survey data. At step 1318, the receptionist enters the information on the PDD forms into the host device, and downloads the sets of patient survey data from the E-PDS into the host at the end of the day. Next, at step 1320, the receptionist runs a correlate function on the PDD and patient survey information. Finally, at step 1322, at the end of the week, the receptionist sends the batch data to the database processor for population of the database.

Figure 14A:
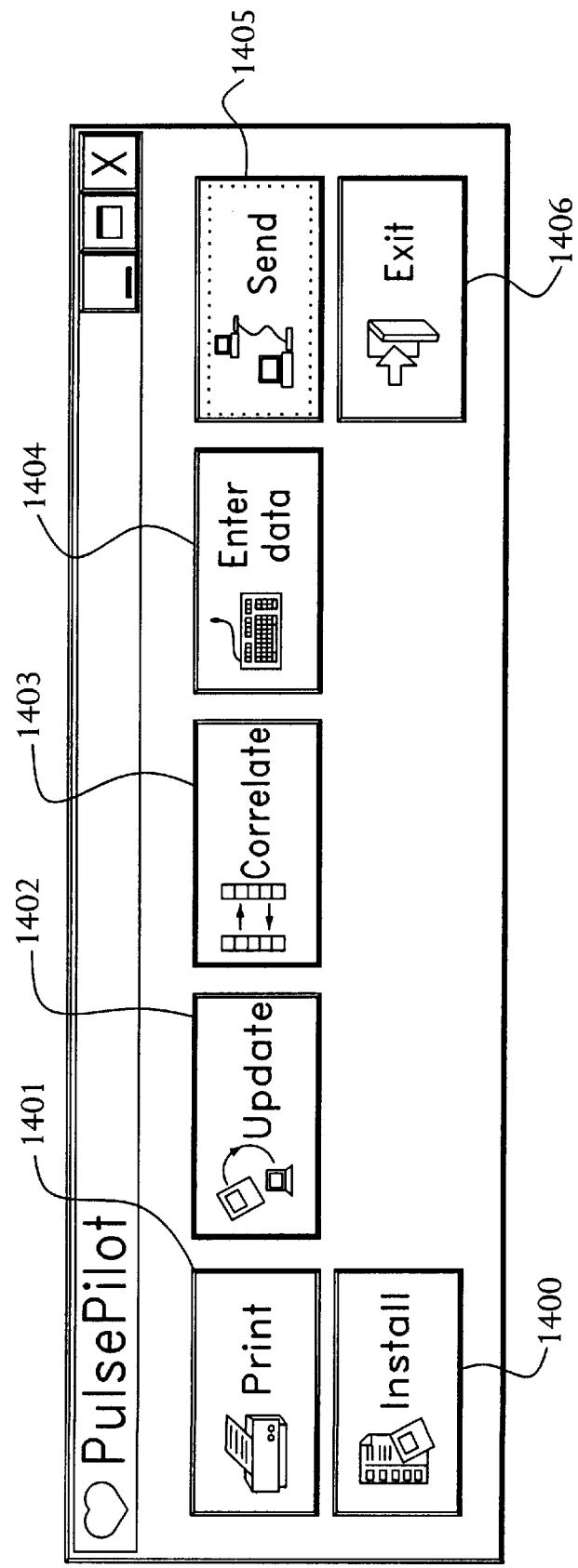
FIG. 14A illustrates a main menu of options of an exemplary embodiment of the host device of the present invention.

FIGS. 14A through 14E illustrate exemplary window screens of the host device 107. FIG. 14A illustrates the main menu of options of the exemplary embodiment activated by clicking the appropriate icon "button": an install program 1400, a print forms 1401, an update 1402 to update the patient/physician data, a correlate 1403 to correlate the physician diagnosis and patient survey data, an enter data 1404 to enter physician diagnosis and patient data, a send

Figure 14B:
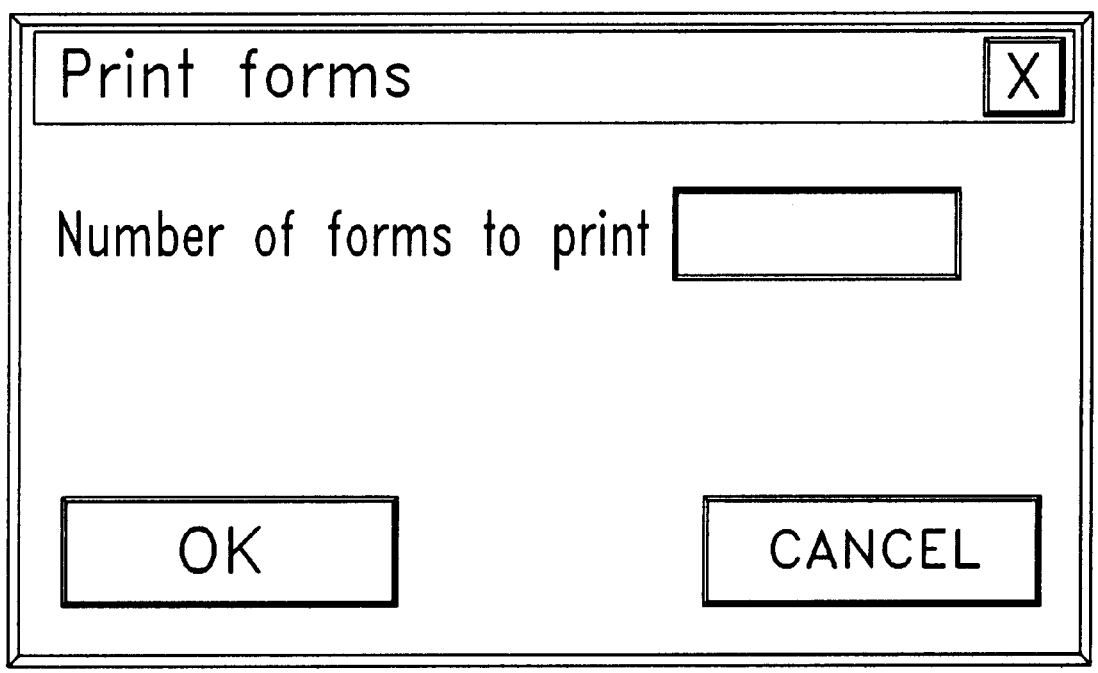
FIG. 14B illustrates a print forms screen of an exemplary embodiment of the host device of present invention.
Figure 14C:
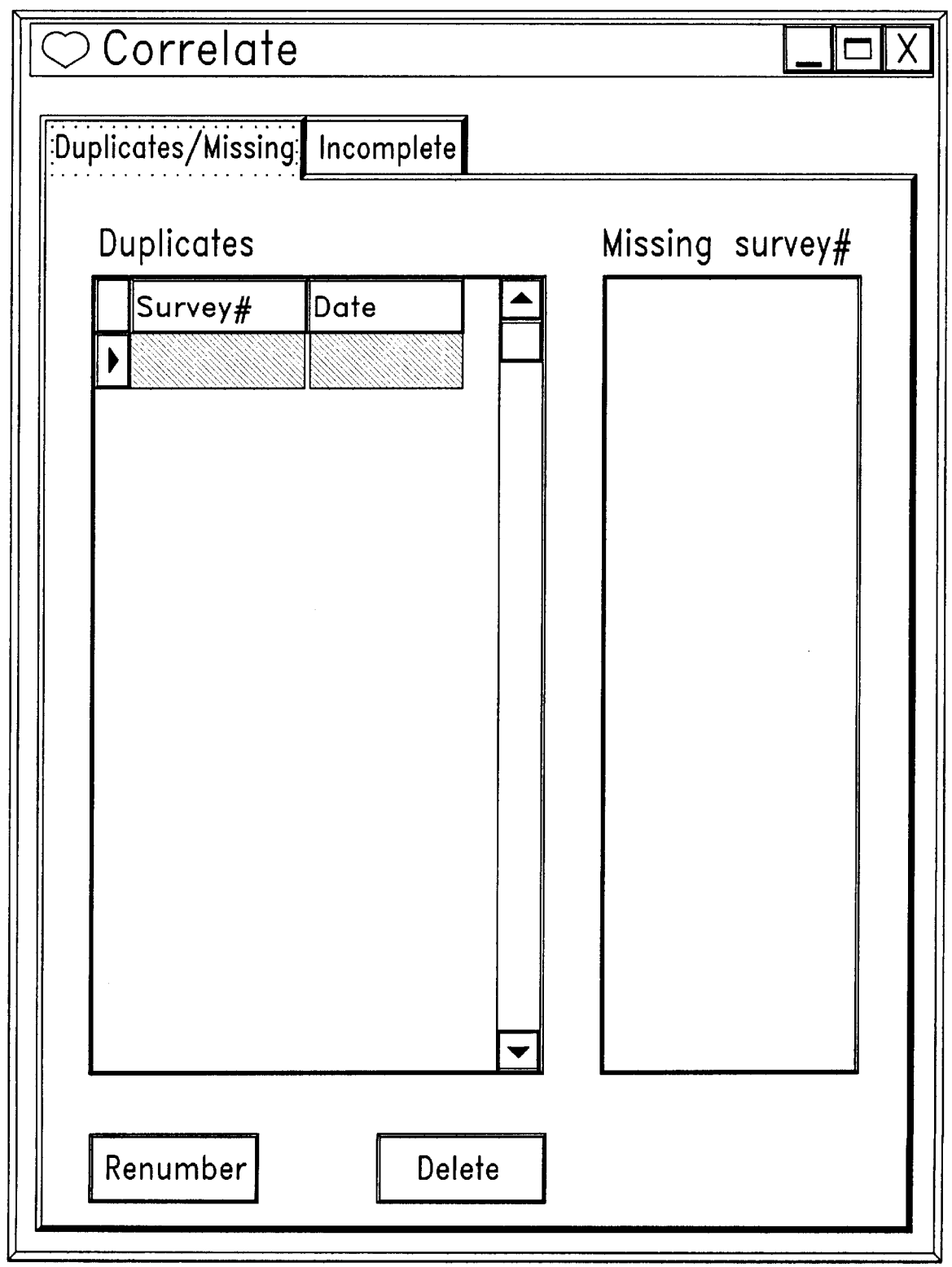
FIG. 14C illustrates a correlate screen of the an exemplary embodiment of the host device of the present invention allowing modification of duplicate or missing information.
Figure 14D:
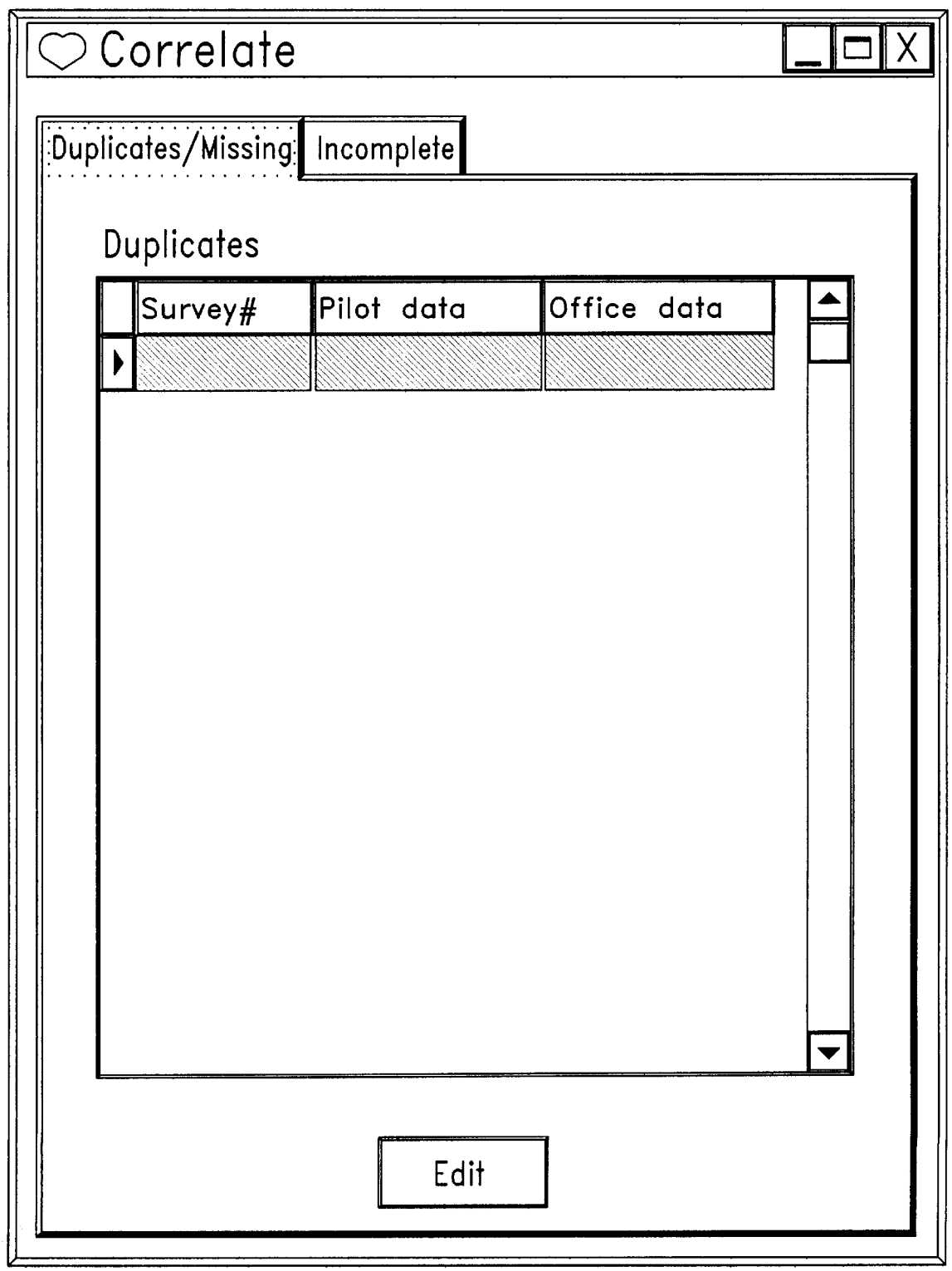
FIG. 14D illustrates a correlate screen of an exemplary embodiment of the host device of the present invention allowing modification of incomplete information.
Figure 14E:
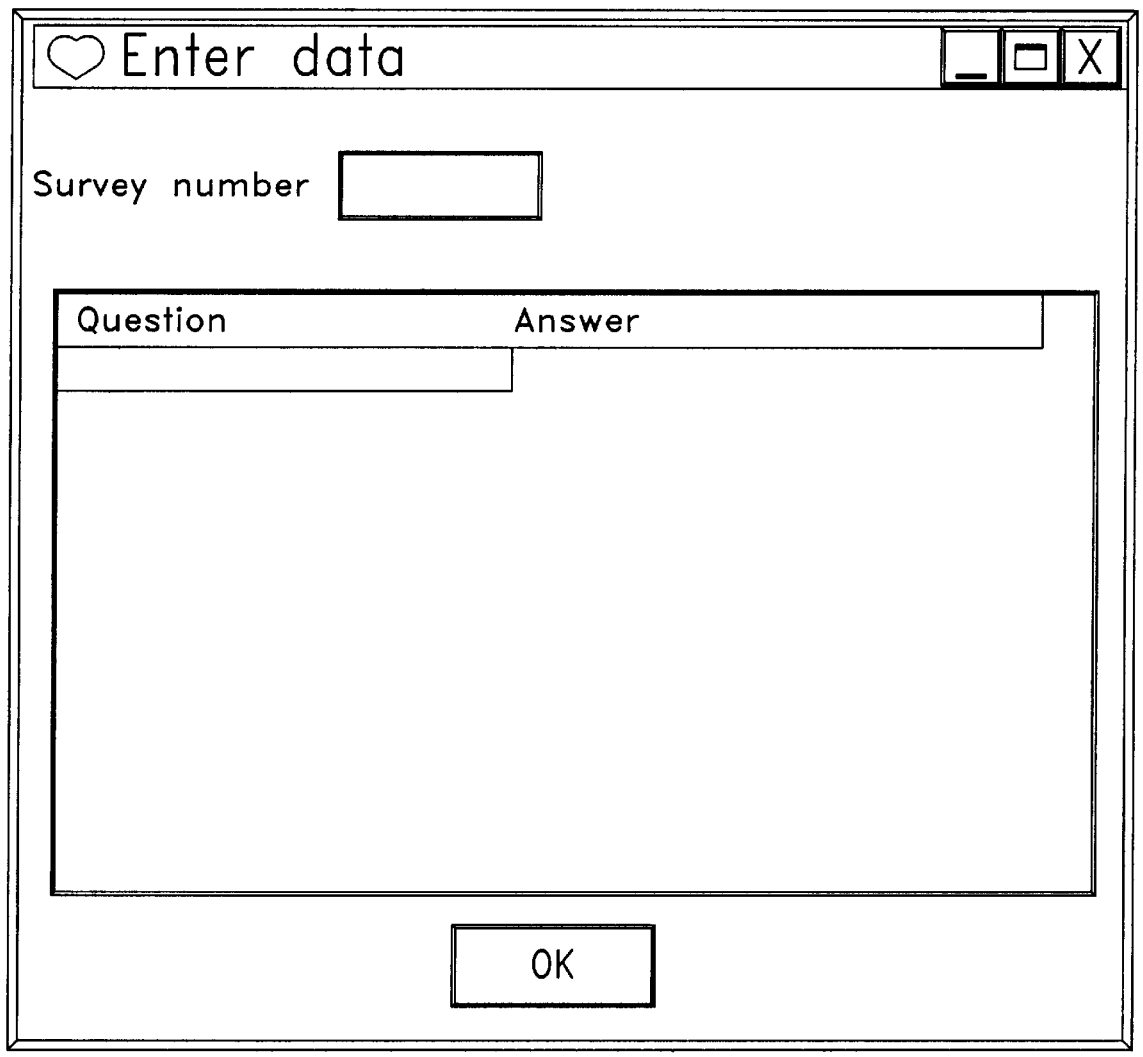
FIG. 14E illustrates an enter data screen of an exemplary embodiment of the host device of the present invention.

1405 to initiate an upload of data from host 107 to database processor 106, and an exit 1406 to end the program. FIG. 14B illustrates a print forms screen. FIG. 14C illustrates a correlate screen of the an exemplary embodiment of the host device of the present invention allowing modification of duplicate or missing survey information based on patient number. FIG. 14D illustrates a correlate screen of the an exemplary embodiment of the host device of the present invention allowing modification of incomplete information such as missing patient or physician data. FIG. 14E illustrates an enter data screen of the an exemplary embodiment of the host device of the present invention.

FIGS. 15–23 illustrate flow charts of a program to implement patient survey data entry employing electronic forms for an E-PDS 103.

Figure 15:
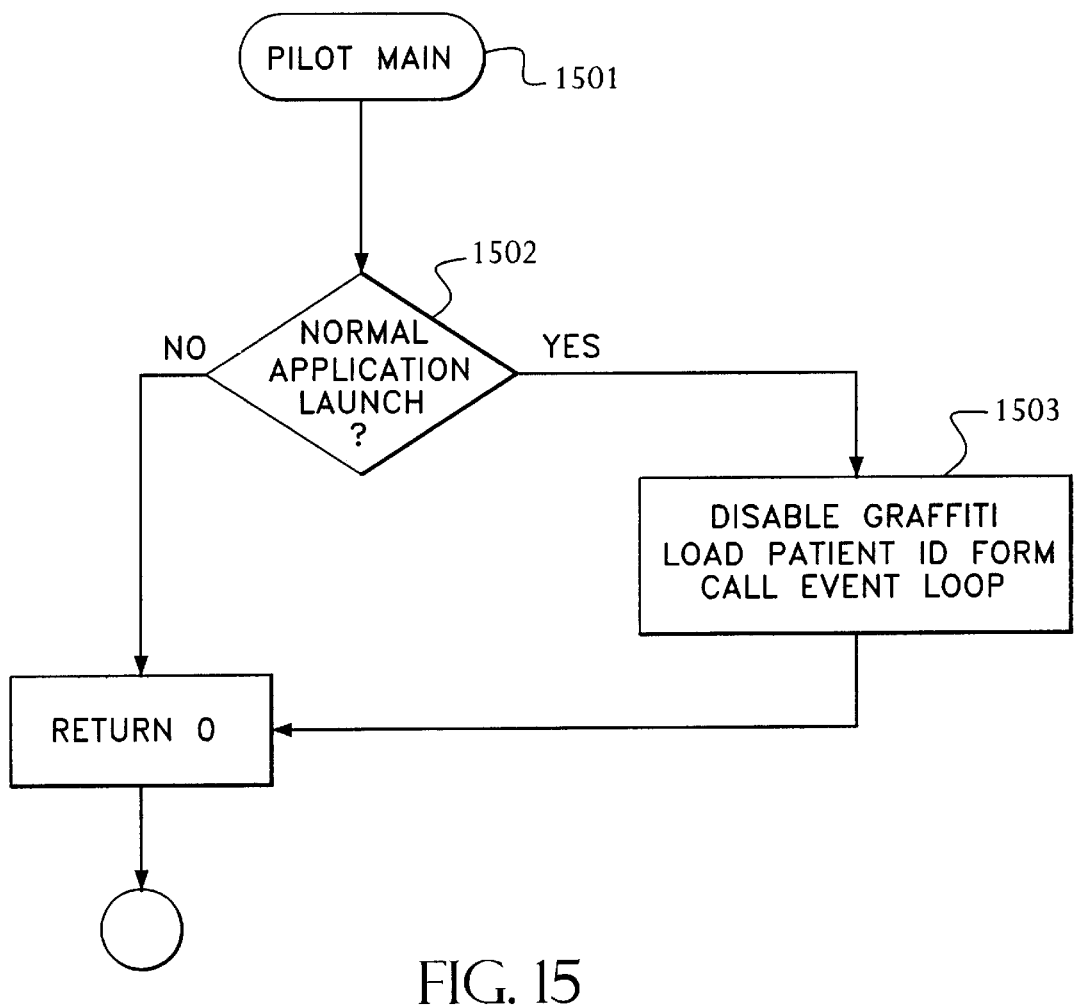
FIG. 15 is an exemplary flow chart of a program to start the survey process and wait for an event when the E-PDS is started.

FIG. 15 is an exemplary flow chart of a program to start the survey process and wait for an event when the E-PDS is started. First, at step 1501, the program initializes, and at step 1502 determines if a normal software application of the hand-held computer is enabled. If so, the survey program exits (returns 0); otherwise, at step 1503, the survey program disables standard handheld functions, or graffiti, loads the first screen to receive the patient identifier (ID) and starts the event loop process (each event is the keying if data from a screen of the handheld computer).

Figure 16:
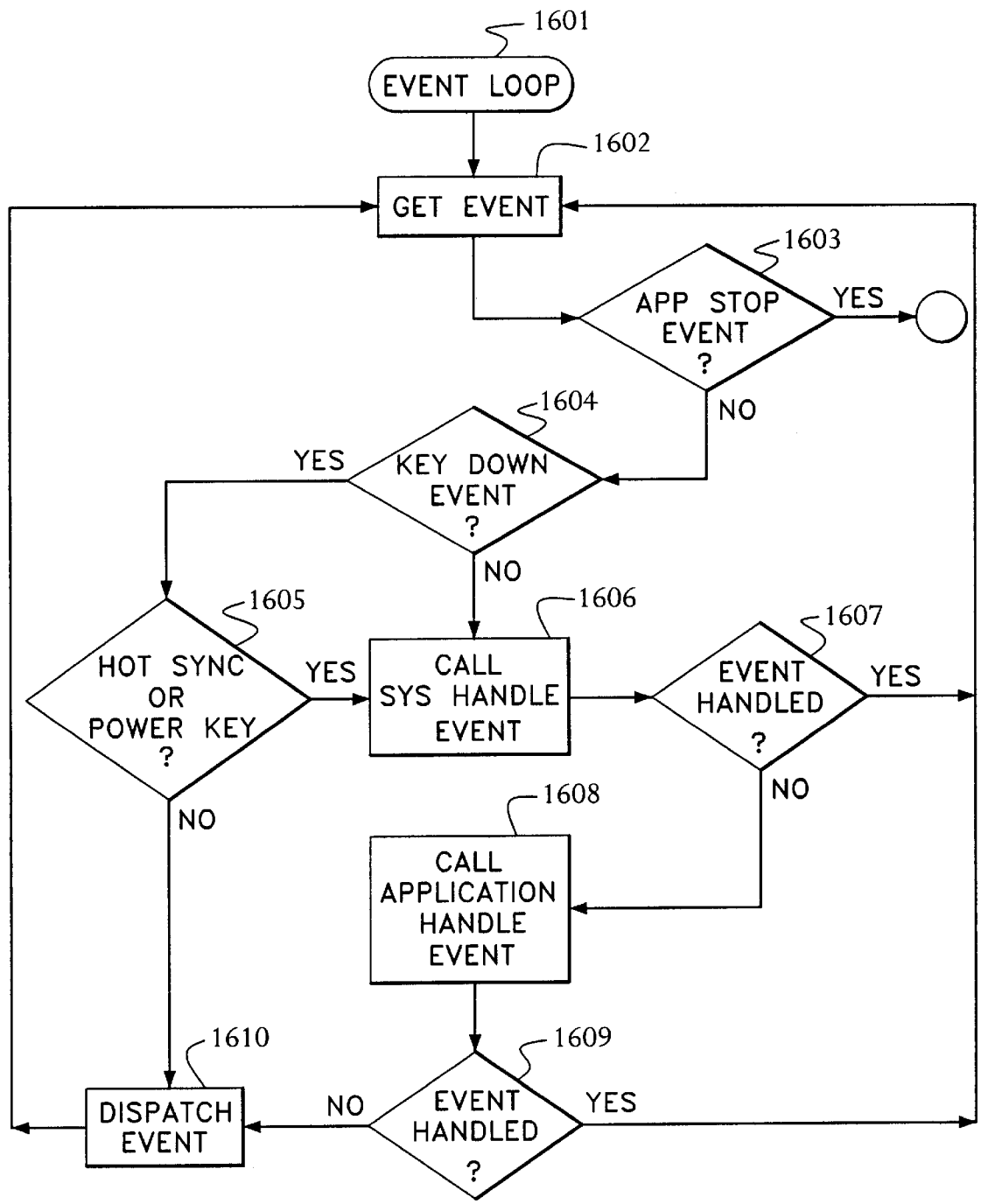
FIG. 16 is an exemplary flow chart of a sub-routine program that obtains a user input event and determines the type of event to be processed for the program of FIG. 15.

FIG. 16 is an exemplary flow chart of a sub-routine program that obtains a user input event and determines the type of event to be processed for the program of FIG. 15. First, at step 1601, the event loop is called, and at step 1602 the program waits for an event. When an event is detected at step 1603, a test is made to see if the event is a command to stop. If so, the program exits; otherwise, at step 1604 a test is made to see if the event is pressing of function keys (keydown) rather than data entry keys. If function keys are pressed, a test is made at step 1605 to determine if the event initiates a hotsync with a host device or is a power off key. If neither of these cases define the event, the event is dispatched at step 1610 and the program returns to step 1602. If the these cases are true, or if no keydown is found at step 1604, the program calls a sys handle event routine at step 1606 to handle a hotsync, or power off commands. At step 1607, the event is tested to see if the syshandleevent routine of step 1606 handled the event. If so, the program returns to step 1602 to get a new event. If not, at step 1608 the routine applicationhandleevent is called to handle a survey forms application. If the event is handled at step 1609, the program returns to step 1602, if the event is not handled at step 1609, the program returns to step 1610 to dispatch the event, and then the program returns to step 1602

Figure 17:
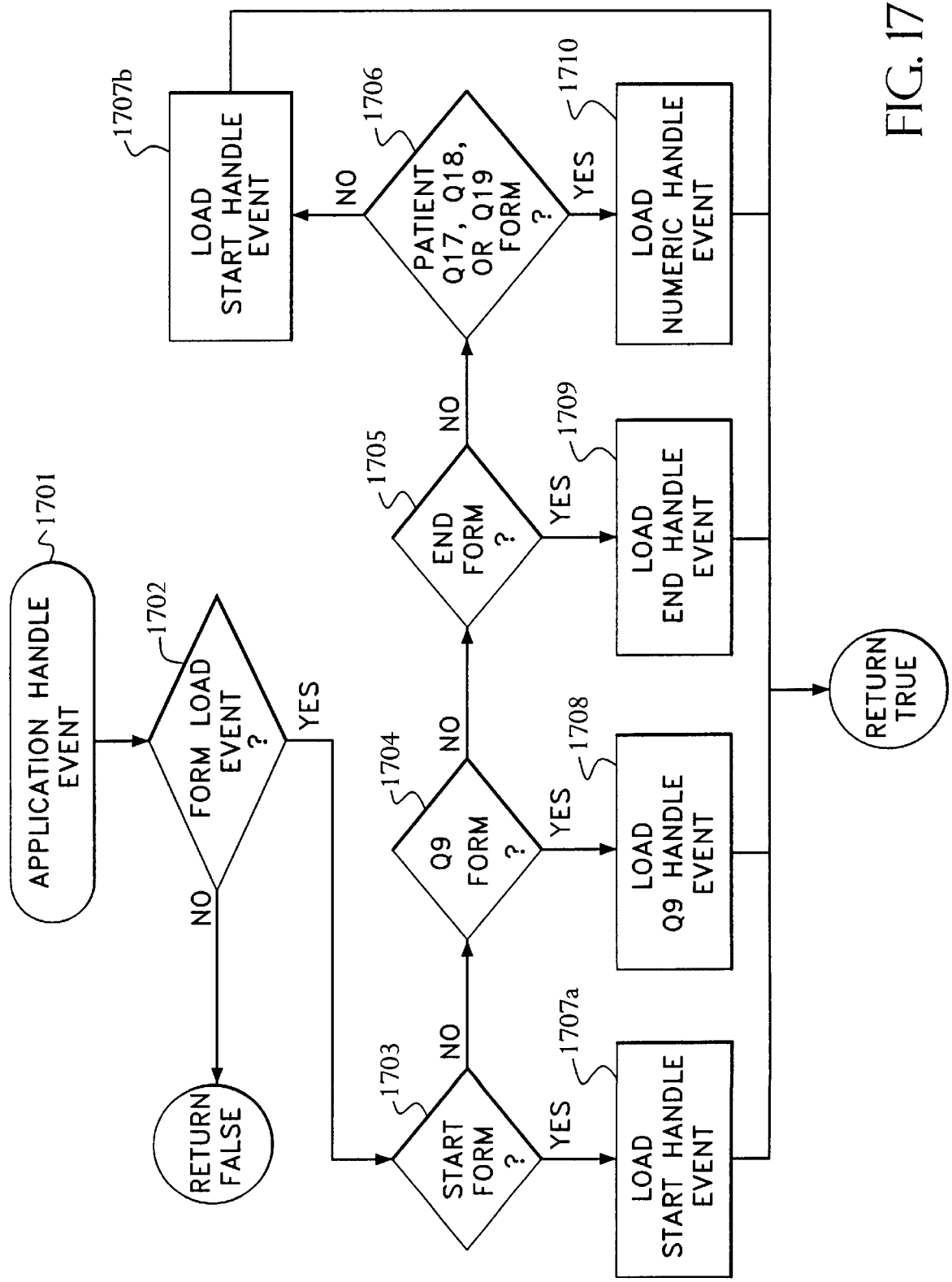
FIG. 17 is an exemplary flow chart of a sub-routine program which processes an application handle event of the program of FIG. 16.

FIG. 17 is an exemplary flow chart of a sub-routine program which processes an application handle event of the program of FIG. 16. When the Application handle event is enabled at step 1701, a test is made at step 1702 to determine whether the event is a request to load a survey form. If not, the program exits, but if so, steps 1703, 1704, 1705, and 1706 respectively determine if the request is to load an initial form, a first type of format form, a termination form or a second type of format form. If at step 1703 the event is a request to load an initial form, at step 1707a the routine load start handle event is called. If at step 1704 the event is a request to load a first type of format form, at step 1708 the routine loads the Q9 handle event routine. If at step 1705 the event is a request to load an survey end form, at step 1709 the routine load end handle event is called. Finally, at step 1706 he test is made if the second format form is to be loaded. If so, at step 1710 the routine load numeric handle event is called, otherwise, at step 1707b the start handle event routine is called.

Figure 18:
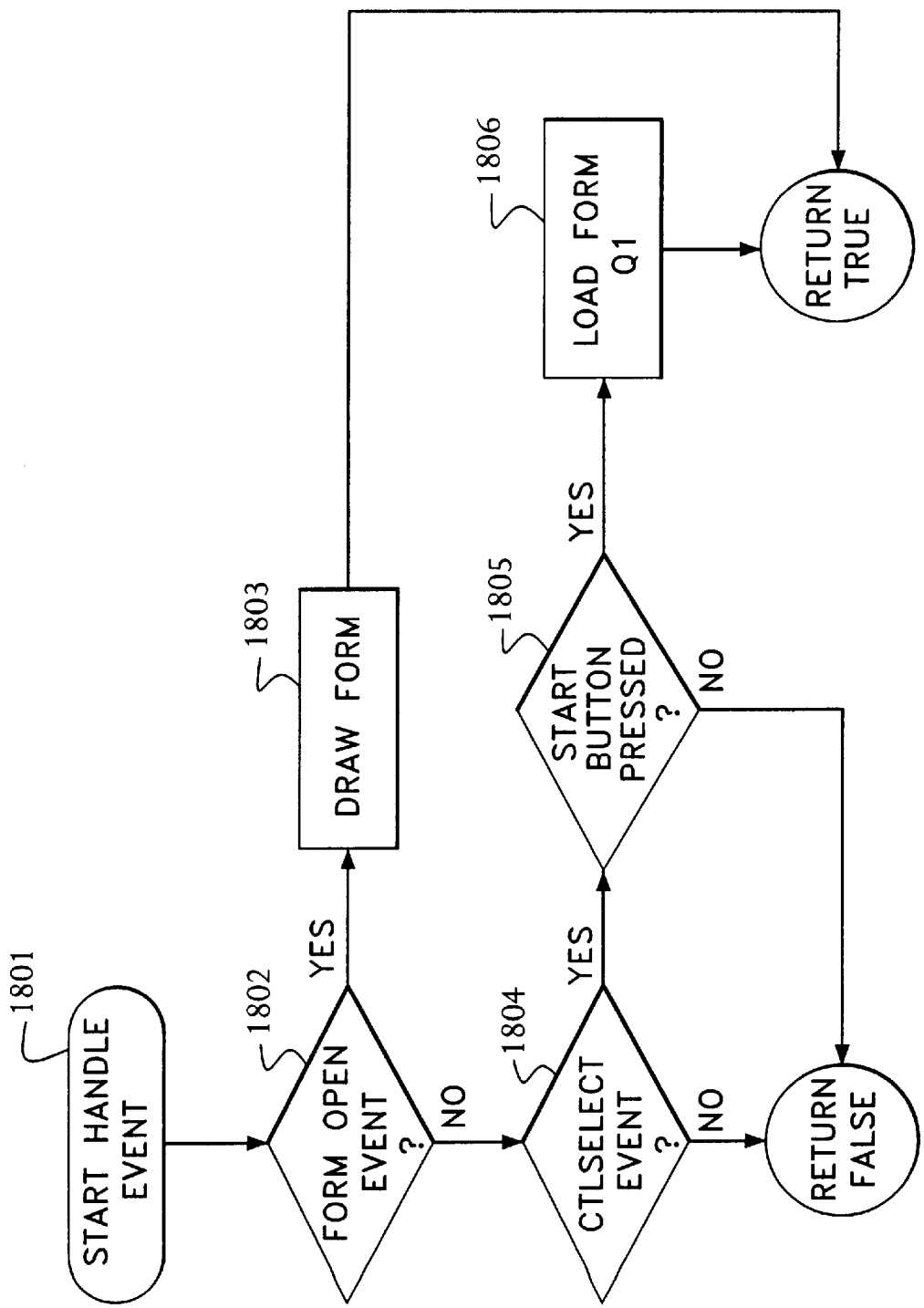
FIG. 18 is an exemplary flow chart of a start handle event sub-routine program of FIG. 17 which provides the survey form to the E-PDS screen to begin a survey.

FIG. 18 is an exemplary flow chart of a start handle event sub-routine program of FIG. 17 which provides the survey form to the E-PDS screen to begin a survey. When the start handle event routine is enabled at step 1801, at step 1802 a test is made to determine if the form has not been loaded (the form open event). If the screen is not loaded, at step 1803 the initial screen of the survey form is drawn on the screen; otherwise, at step 1804 at test is made to determine if the event is pressing of a keypad key. If so, a test is made at step 1805 to determine if the key pressed matched the start button, indicating a start of the survey. If so, the next form, Q1, is loaded to the screen at step 1806.

Figure 19:
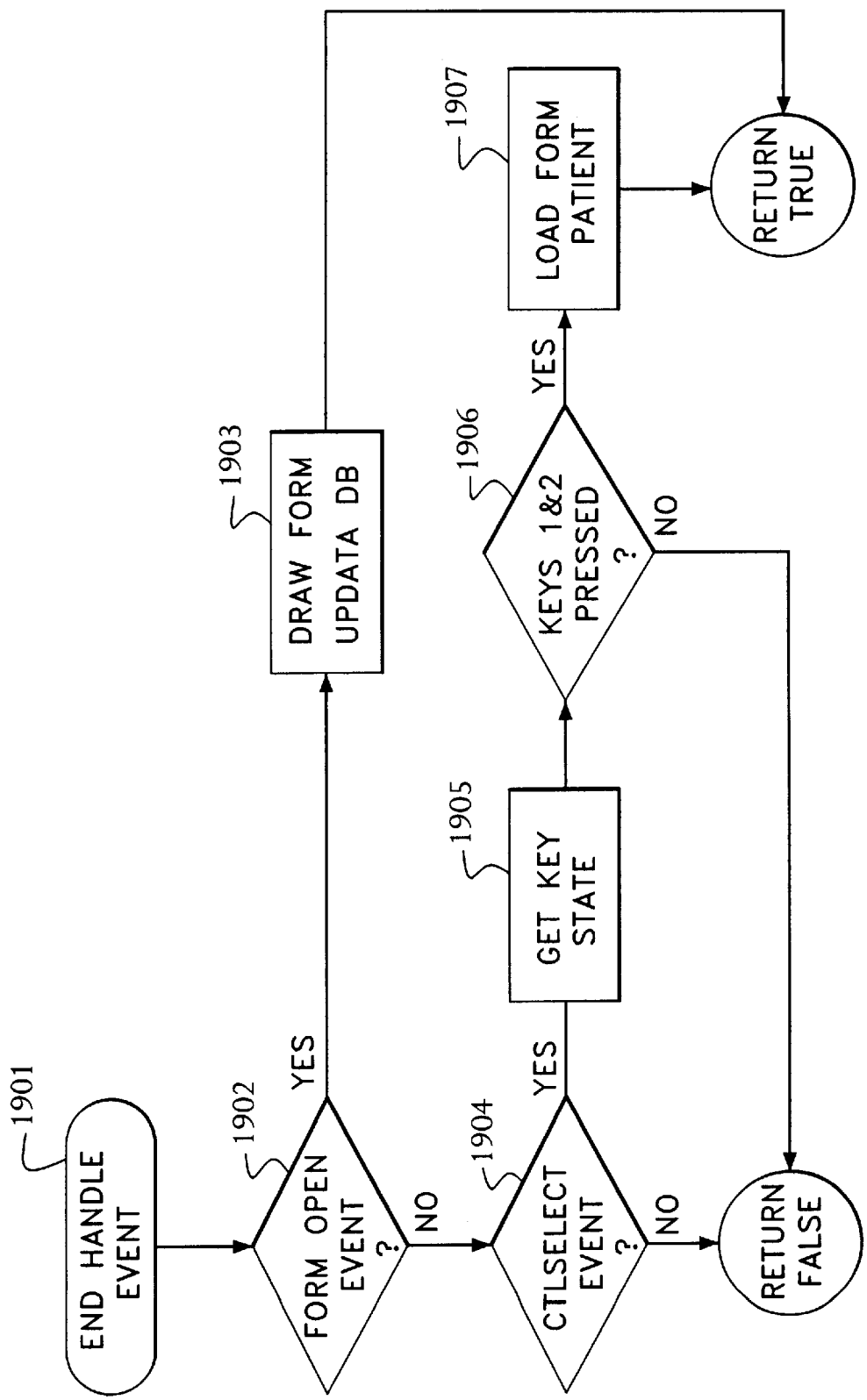
FIG. 19 is an exemplary flow chart of a end handle event sub-routine program of FIG. 17 which ends the survey by ending event processing as indicated to the E-PDS screen.

FIG. 19 is an exemplary flow chart of a end handle event sub-routine program of FIG. 17 which ends the survey by ending event processing as indicated to the E-PDS screen. When the end handle event routine is enabled at step 1901, at step 1902 a test is made to determine if the form has not been loaded (the form open event). If the screen is not loaded, at step 1903 the final screen of the survey form is drawn on the screen and the database is updated by calling the update database routine; otherwise, at step 1904 at test is made to determine if the event is pressing of a keypad key. If a keypad key is pressed, the key state, or value, is retrieved at step 1905. A test is made at step 1906 to determine if both keys 1 and 2 were pressed, and if so the initial patient form is loaded at 1907, ready to receive the patient ID to begin a new survey.

Figure 20:
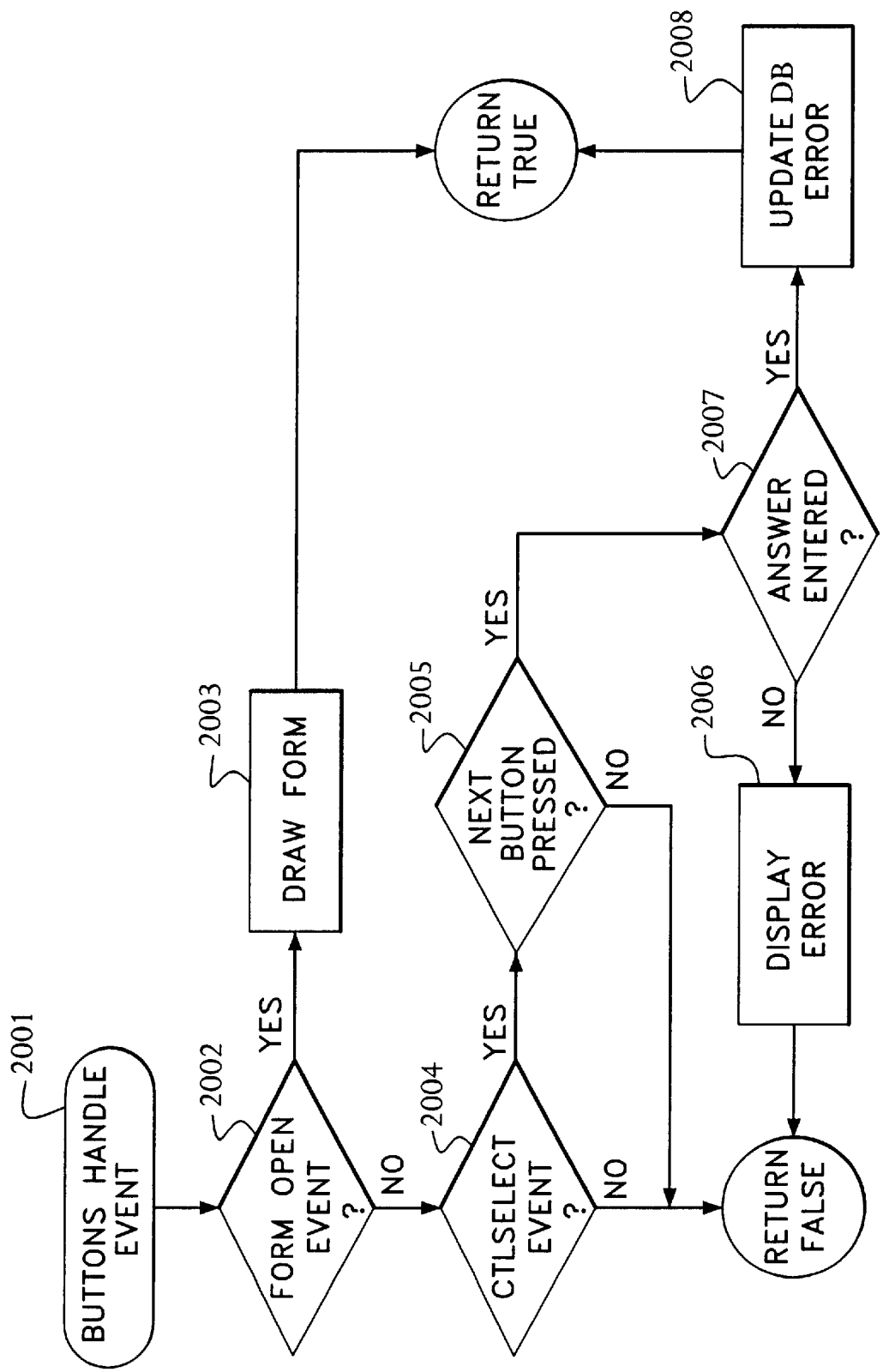
FIG. 20 is an exemplary flow chart of a subroutine program which processes a buttons handle event to move check if a survey question is answered and move to the next question.

FIG. 20 is an exemplary flow chart of a subroutine program which processes a buttons handle event to check if a survey question is answered and move to the next question. When the buttons handle event is enabled at step 2001, a test is made at step 2002 to determine whether the survey form is to be drawn on the screen. If so, the form is drawn at step 2003; if not, a test is made at step 2004 if a data entry event has been made. If so, a test is made to determine if the "next" data value was pressed at step 2005. If the next button was pressed, then at step 2007 a test is made to determine if the data for the question of the form has been answered. If not, at step 2006 an error message is displayed. If the data has been entered, then the database update routine is called and the next survey form is loaded at step 2008.

Figure 21:
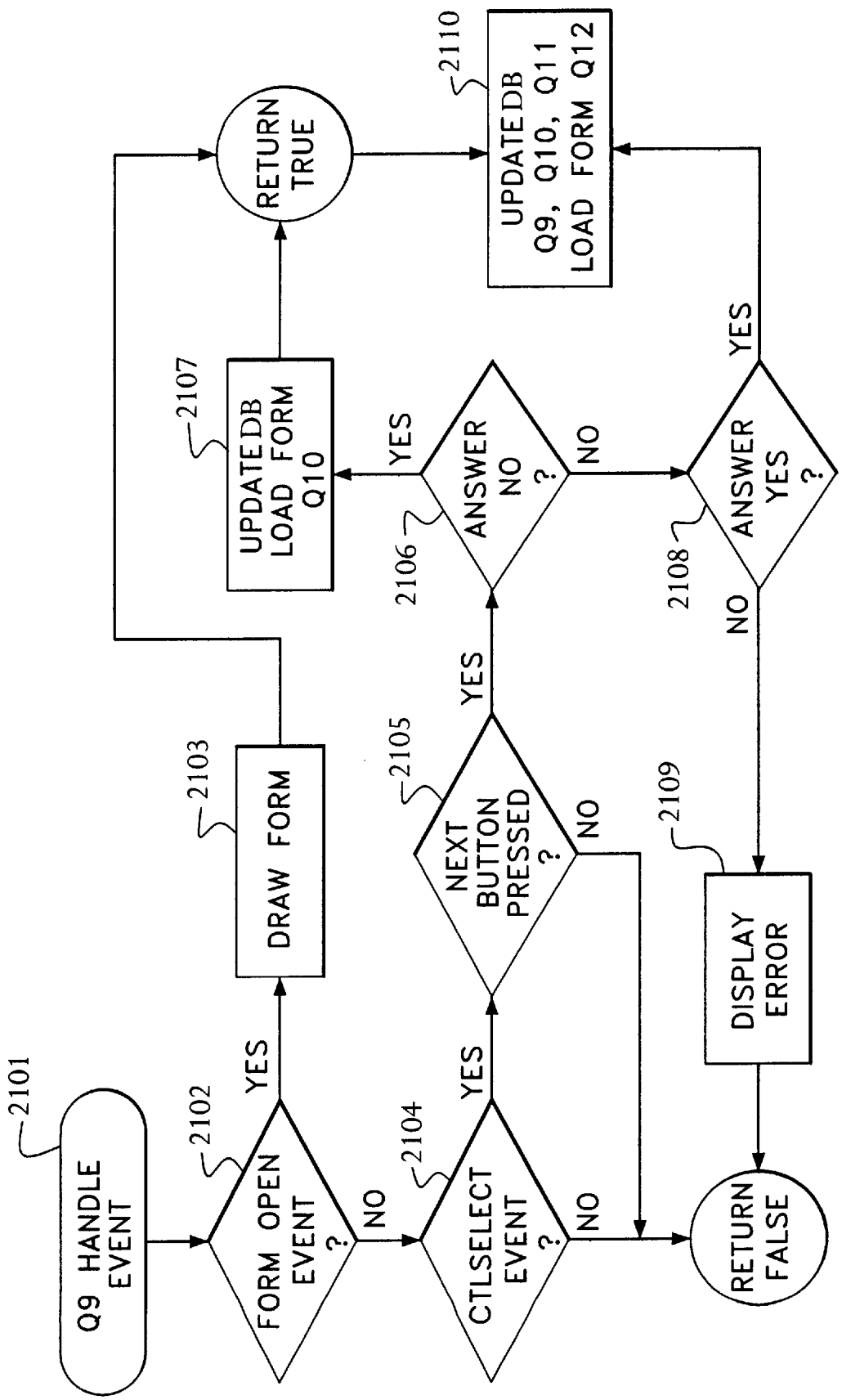
FIG. 21 is an exemplary flow chart of a sub-routine program which enables data entry for a predetermined set of survey questions.

FIG. 21 is an exemplary flow chart of a sub-routine program which enables data entry for a predetermined set of survey questions which have yes/no answers. When the Q9 handle event is enabled at step 2101, a test is whether the survey form is to be drawn on the screen at step 2102. If so, the form is drawn at step 2103; if not, a test is made at step 2104 if a data entry event has been made. If so, a test is made to determine if the "next" data value was pressed at step 2105; If so, then at step 2106 the data entry is tested for a "no" value. If the data value is not "no", then the value is tested for a "yes" value at step 2108. If the answer is not "yes" at step 2108, then an error value is displayed at step 2109; If the answer is "yes", then at step 2110 the update database routine is called for selected questions, and the last form of the group is loaded. If the answer at step 2106 was a "no", then at step 2107 the update database routine is called and the next form is loaded.

Figure 22:
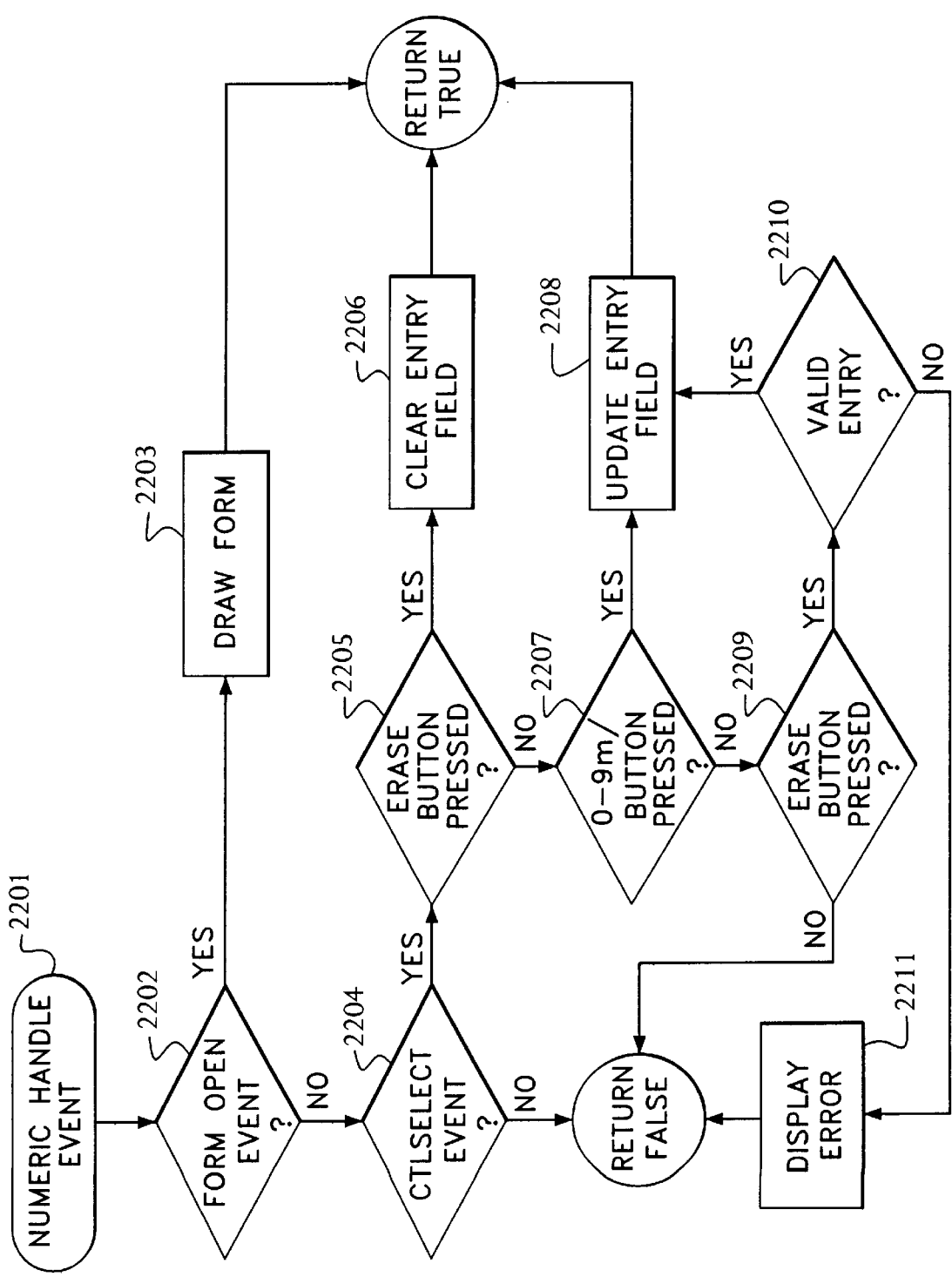
FIG. 22 is an exemplary flow chart of a sub-routine program which allows screen input data to be entered in numeric form as a screen keypad

FIG. 22 is an exemplary flow chart of a sub-routine program which allows screen input data to be entered in numeric form as a screen keypad. First, at step 2201, the numeric handle event routine is enabled, and at step 2202 a test is made to see if the form for the next question is not written (form open event) if so, the form is drawn on the screen at step 2203; otherwise at step 2204 the routine waits for a data entry event. If a data entry event is detected at step 2204, a test at step 2205 is made to see if the event was an erase button activation, and if so at step 2206 the entry field is cleared. If at step 2205 the erase button is not activated, at step 2207 a test is made to see if a numeric entry was made. If so, at step 2208 an entry field is updated; otherwise at step 2209 a test is made to see if the entry indicates that the user requests the next form. If the next request is made at step 2209, a test is made at step 2210 to verify that the next request is a valid entry. If not valid entry, at step 2211 an error message is displayed.

Figure 23:
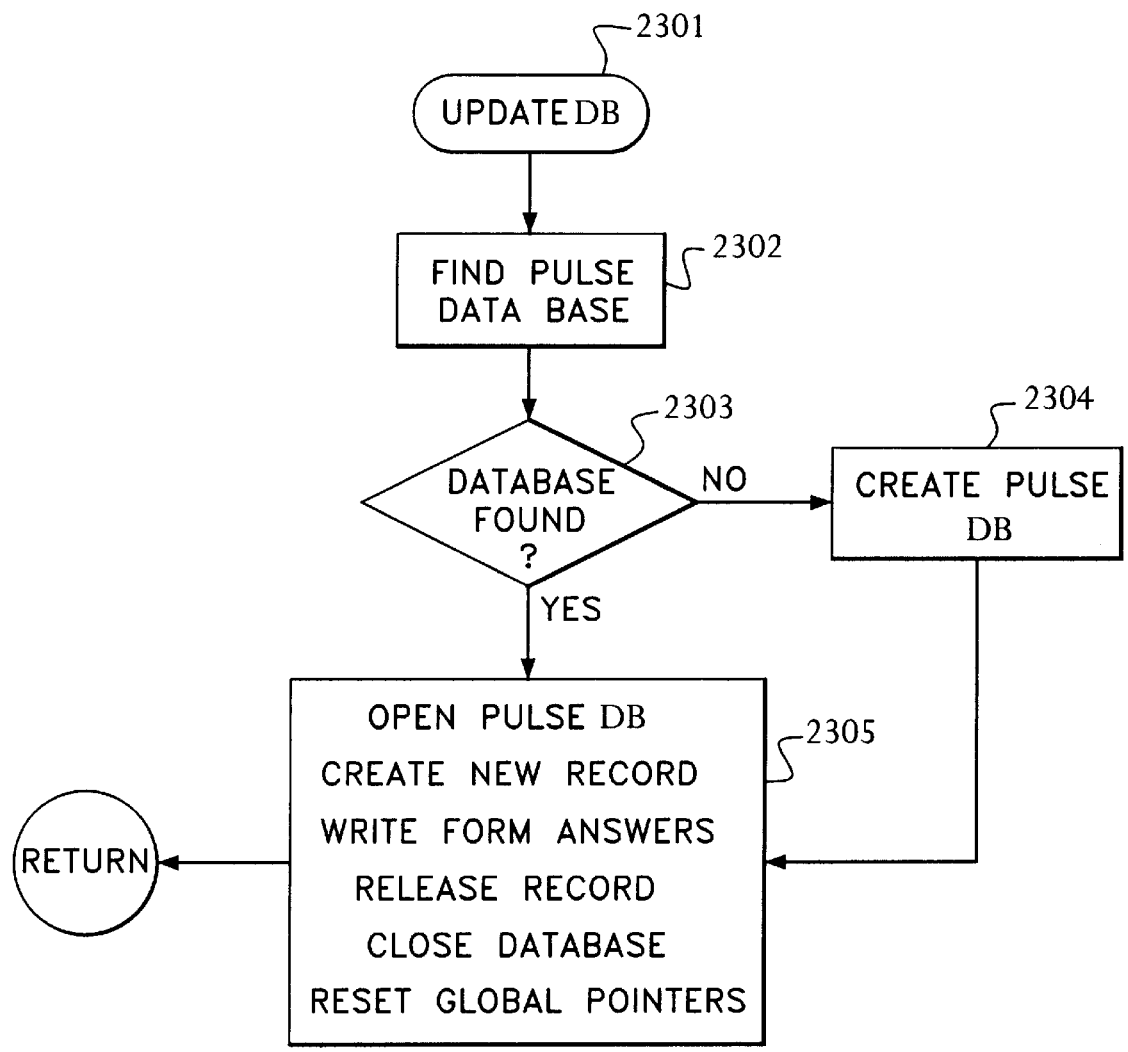
FIG. 23 is an exemplary flow chart of the program to from a record and update a database with the information gathered from a survey form.

FIG. 23 is an exemplary flow chart of the program to from a record and update a database with the information gathered from a survey form. As shown in FIG. 23, at step 2301 the update database routine is enabled, and at step 2302 a processor attempts to find an existing database. If the database is found at step 2303, at step 2305 the database is opened, a new record of the survey data is created, the answers are written for the record, the database is closed, and the program resets to begin a new survey application If the database is not found at step 2303, at step 2304 a new database is created, and the program then proceeds to step 2305.

Appendix C provides an exemplary database format for a particular embodiment of the present invention; similarly, Appendix D provides an exemplary software hierarchy for software programs according to the flow charts as illustrates in FIGS. 15–23

A further embodiment may include an automated electronic form generator (not shown), which may take particular survey forms and generate the electronic forms for use with the E-PDS 103.

In the exemplary embodiment described, the electronic forms shown are related to a particular treatment. However, the forms, and the content of the forms, can be tailored to, for example, the particular diagnosis or treatment, particular patient, or particular practice or specialty.

The Outcomes Measurements Reporting and Tracking System

The Outcomes Measurement Module 112 of FIG. 1 implements a "feedback loop" for tracking the results of the analyzed data. The Outcomes Measurement Module receives defined parameters, such as, for example, a particular practice or a particular treatment regimen, and periodically schedules selected algorithms for analysis by the Data Analysis Processor 108. The results of these periodic scheduled events are recorded and analyzed for trends in the data.

According to one aspect of the present invention, the System for data collection improves processing of database information through system performance measurement. The outcomes measurement process tracks the progress of perceived quality of a physician's practice, as well as based on a regional or national comparison. In another embodiment, the performance of a physician's efforts to improve quality of diagnosis, treatment and are also compared against the processed information both historically and regionally. In another embodiment, those areas of practice performance identified by processed information which are resistant to improvement efforts by physicians despite being identified are analyzed to improve the information gathering aspects of the machine readable forms.

A further aspect of the invention regarding the "self learning" of the outcomes measurement tracking is the ability of the system to correlate patient diagnosis, treatment outcomes, and the patient responses to particular questions of the machine readable form. A strong correlation between patient responses and particular treatment outcomes are used to identify patients who are "at risk" of an adverse outcome, either in the patient's perception of care or in the patient's actual health outcome. For example, for a particular diagnosis or treatment for adverse mental health outcomes, such as depression, the data may show a particular correlation to low satisfaction scores in several questions. Therefore, a physician who receives a survey from a patient during a treatment session which has low satisfaction scores in those questions is alerted to the possibility that the patient may possibly have the adverse mental health outcome.

While preferred embodiments of the invention have been shown and described herein, it will be understood that such embodiments are provided by way of example only. Numerous variations, changes, and substitutions will occur to those skilled in the art without departing from the spirit of the invention. Accordingly, it is intended that the appended claims cover all such variations as fall within the spirit and scope of the invention.

APPENDIX A

| Patient Age and Gender | Time to Complete Survey | Ease of Use? | Comments |
| --- | --- | --- | --- |
| Field Test Summary Results | | | |
| 69 Female | 4 minutes | No problems | "Very clever, faster than paper" |
| 76 Female | 6 minutes | No problems. This patient could not complete the written survey due to severe arthritic condition. however she could do the Pilot! | "Very nice, I should tell my son, 'the doctor' about this." "this is easy" |
| 87 Female | 4:30 minutes | Adult child completed for her mother due to her v.poor vision. She completes the paper for her daughter as well. | "Excellent tool, faster than paper" "contrast would be better in black and white" |
| 66 Female | 4 minutes | No problems | "Interesting gadget!" |
| 87 Male | 4 minutes | Needed Assistance, and requires assistance with paper as well | None |
| 75 Female | 4:30 minutes | No problem - used back light on screen | "Very useful, quick and easy" |

APPENDIX A-continued

| Patient Age and Gender | Time to Complete Survey | Ease of Use? | Comments |
|---|---|---|---|
| 42 Female | 4:40 minutes | No problems | "Great" "Easy to use". "much better than the voluminous paper surveys I get" |
| 12 Female | 3:45 minutes | No problems | "Neat!" |
| 51 Female | 5 minutes | No problems | "Fun!" "Easier than paper forms" |
| General Practice ||||
| 75 F | NA | NA | No time - had driver waiting w/sm. Child |
| 35 M | 5:00 | None | "THat was fast" |
| 42 F - patients mother. Pt. Age - 6 | 5:00 | None | "Faster than paper. I am more inclined to want to complete this. . ." |
| 60 M | 5:30 | None | "Good, very quick, better than paper" |
| 13 M | 4:00 | None | "Cool" |
| 15 F | 4:30 | None | "Fun" |
| 62 F | NA | NA | "I'm too shaken up by EKG to complete" |
| 45 M | 4:30 | None | "Neat". "It's good to know my opinion counts" |
| 30 F | NA | NA | "Late for therapy" |
| 42 M | NA | NA | Did not read English. |
| Internal Medicine ||||
| 45 | Pilot froze, couldn't complete survey | | "I'm having fun. This is the best part of my day. This is really neat. |
| 36 | | Easier to use than paper | "It's neat" |
| 70 | | Nurse? Not good question since there is no nurse | "I like it better than paper. It's not hard." |
| 10 | Finished easily and quickly. | it." | "Can I try it? Can I try |
| 70 | | "I can't see it. I don't have my glasses on." Then she finished the survey. | "Yeah, I'ii do it. You should pay me". "That wasn't so bad! |
| 83 | | "That wasn't so bad. That other lady took such a long time, I thought it would be hard, but if that's all it is, it's no problem." | |
| 83 | | Was very reluctant to try, but when her friend did it, she was able to too and had no problems | "That's nice." |
| 35 | Declined firmly. Not interested. | | |
| 35 | | | "It was O.K. Seems efficient." |
| 36 | | | This is easy to use. Quite fun. |
| 65 | | I prefer this to paper because my handwriting is poor. | |

Notes:

Office Flow

The survey was completed after the visit by each patient as they checked out and set their next appointment. The patients stand at the reception counter to complete the survey or take a seat in the waiting area. Average completion time is 4.6 minutes. One field test was conducted without timing and no patient was aware they were being timed during survey completion.

Patient Instruction

The required time to instruct the patient to use the survey averaged 30 seconds per patient. Instruction on the use of the Palmtop computer was very well received in every case. Children seem to need no instructions! During the survey, a few patients questioned the meaning of certain questions, but none required further instruction on use of the device.

Impact on Staff

Expected time to instruct patients on the system start up is less than one minute per patient and after one time using the system, a patient should not require any additional instructions.

Appendix B

PulseGroup Inc

Report for Harold Good, M.D.

*A Member of the Good Doctor Network*

*Monthly Summary for September, 1997*

SATISFACTION

- Your patients submitted 83 surveys this month on which these figures are based. The domain charts in Section 2 are based on all surveys received year-to-date.

- 93% of your patients expressed their satisfaction with the medical care they received.

- 87% of your patients expressed satisfaction with the office administration (i.e. telephone courtesy, reception, waiting time).

- 96% of your patients said they would recommend or highly recommend your office to their friends.

- 82% of your patients expressed satisfaction with their insurance plans

AVERAGES FOR YOUR PRACTICE

- The average age of your patients as reported in surveying was 43.

- Your patients spent an average of 9 minutes waiting to see you.

- Your patients spent an average of 5 minutes with your nurse/assistant.

- You spent an average of 14 minutes with each patient.

COPYRIGHT PULSEGROUP INC 1997

DOMAINS

DOMAIN 1: SATISFACTION WITH MEDICAL CARE

| | | |
|---|---|---|
| Q3 | Satisfaction with results of treatment provided | Scale 1 to 5, Worst to Best |
| Q4 | Information provided about my medical condition | Scale 1 to 5, Worst to Best |
| Q8 | Satisfaction with drug treatment | Scale 1 to 5, Worst to Best |
| Q12 | Was time spent with nurse useful? | Yes or No |
| Q14 | Was time spent with doctor useful? | Yes or No |
| Q15 | Is the treatment improving your condition? | Yes or No |

DOMAIN 2: SATISFACTION WITH OFFICE PROCEDURES

| | | |
|---|---|---|
| Q1 | Availability of convenient appointment | Scale 1 to 5, Worst to Best |
| Q2 | Courtesy of reception and check-in | Scale 1 to 5, Worst to Best |
| Q5 | Accessibility of doctor by telephone | Scale 1 to 5, Worst to Best |
| Q10 | Was time spent waiting to see the doctor acceptable? | Yes or No |

DOMAIN 3: OVERALL FEELING

| | | |
|---|---|---|
| Q6 | Feeling about recommending this office to others | Scale 1 to 5, Worst to Best |

DOMAIN 4: SATISFACTION WITH INSURANCE

| | | |
|---|---|---|
| Q7 | Satisfaction with insurance plan | Scale 1 to 5, Worst to Best |

SECTION 1

PATIENT SATISFACTION by DOMAIN*
*Harold Good, M.D.* (Sept '97; 83 patients)
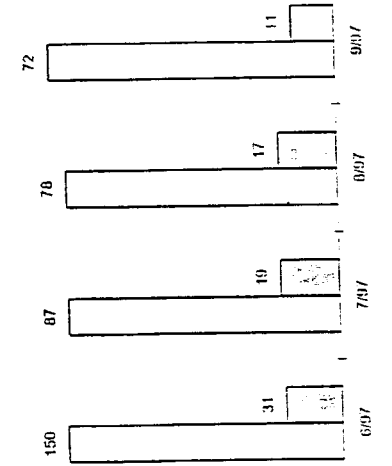
MEDICAL TREATMENT
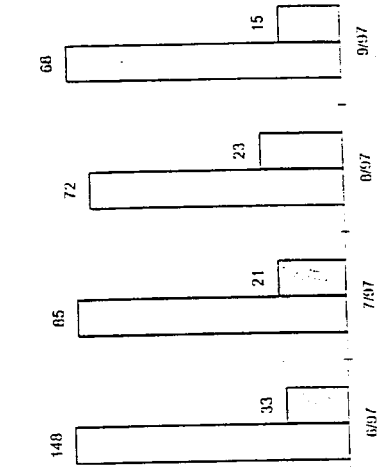
OFFICE PROCEDURES
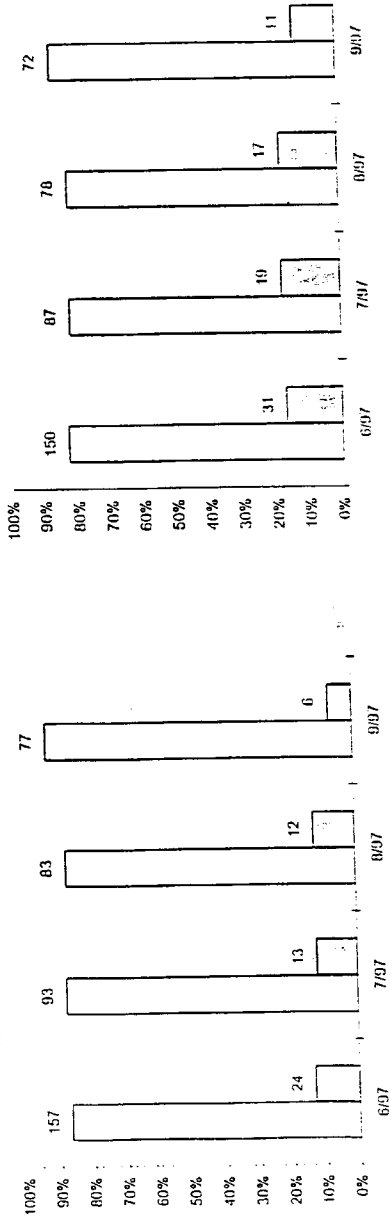
WOULD YOU RECOMMEND THIS OFFICE?
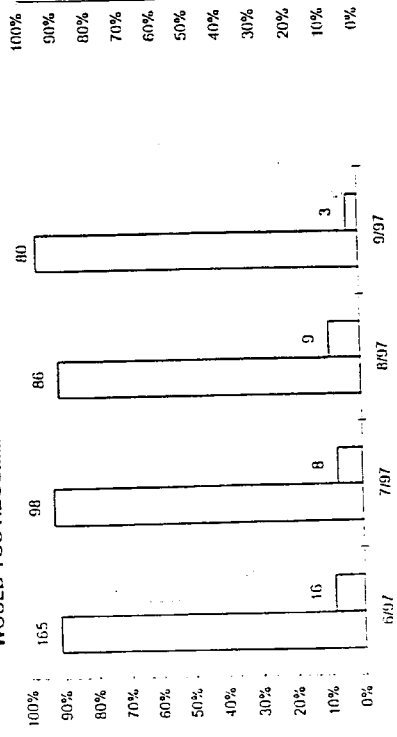
INSURANCE
*Positive responses are white. Neutral or dissatisfied responses are gray.
SECTION 2

INDIVIDUAL RESPONSES

SECTION 3

| AGE | GENDER | MEDICAL CARE | | | | | | OFFICE PROCEDURES | | | OVERALL FEELING | INSURANCE |
|---|---|---|---|---|---|---|---|---|---|---|---|---|
| | | Q3 | Q4 | Q8 | Q12 | Q14 | Q15 | Q1 | Q2 | Q5 | Q10 | Q6 | Q7 |
| 29 | M | | 1 | 1 | Y | Y | N | 1 | 1 | | Y | 1 | 1 |
| 53 | M | | 1 | 1 | Y | Y | Y | 1 | 1 | 1 | Y | 1 | 1 |
| 54 | M | 4 | 5 | 5 | Y | Y | Y | 5 | 4 | 5 | Y | 4 | 5 |
| 22 | F | 5 | 5 | 5 | Y | Y | Y | 4 | 3 | 5 | Y | 4 | 5 |
| 24 | M | 5 | 5 | 5 | Y | Y | Y | 4 | 3 | 4 | Y | 4 | 2 |
| ** | ** | 5 | 5 | 4 | Y | Y | Y | 5 | 3 | 3 | Y | 4 | 3 |
| 35 | M | 5 | 5 | 5 | Y | Y | Y | 5 | 4 | 4 | Y | 5 | 5 |
| 35 | F | 4 | 4 | 4 | Y | Y | Y | 4 | 4 | 5 | Y | 5 | 4 |
| 12 | M | 5 | 5 | 5 | Y | Y | Y | 5 | 5 | 4 | Y | 5 | 4 |
| 24 | M | 4 | 4 | 4 | Y | Y | Y | 4 | 4 | 4 | Y | 5 | 2 |
| 25 | F | 4 | 5 | 5 | Y | Y | Y | 5 | 4 | 4 | Y | 5 | 4 |
| 40 | M | 4 | 4 | 4 | Y | Y | Y | 5 | 5 | 5 | Y | 5 | 5 |
| 43 | M | 5 | 5 | 5 | Y | Y | Y | 5 | 5 | 5 | Y | 5 | 4 |
| 59 | F | 4 | 5 | 5 | Y | Y | Y | 5 | 3 | 5 | Y | 5 | 2 |
| 29 | M | 5 | 5 | 5 | Y | Y | Y | 4 | 5 | 5 | Y | 5 | 2 |
| 39 | ** | 5 | 5 | 5 | Y | Y | Y | 5 | 5 | 5 | Y | 5 | 2 |
| ** | ** | ** | ** | ** | ** | ** | ** | ** | ** | ** | ** | ** | ** |
| 37 | M | 3 | 5 | 2 | Y | Y | Y | 4 | 3 | 1 | Y | 5 | 3 |
| 43 | M | 5 | 5 | 5 | Y | Y | Y | 5 | 5 | 5 | Y | 5 | 5 |
| 75 | F | 5 | 5 | 4 | Y | Y | Y | 5 | 5 | 5 | Y | 5 | 4 |
| 35 | F | 5 | 5 | 5 | Y | Y | Y | 5 | 5 | 5 | Y | 5 | 5 |
| 71 | F | 5 | 5 | 5 | Y | Y | Y | 5 | 5 | 4 | Y | 5 | 5 |
| 50 | M | 5 | 5 | 5 | Y | Y | Y | 5 | 5 | 5 | Y | 5 | 5 |
| 57 | M | 5 | 5 | 5 | Y | Y | Y | 5 | 5 | 5 | Y | 5 | 5 |
| 40 | F | 5 | 5 | 5 | Y | Y | Y | 5 | 5 | 5 | Y | 5 | 5 |
| 43 | F | 5 | 5 | 5 | Y | Y | Y | 5 | 5 | 5 | Y | 5 | 5 |
| 54 | F | 5 | 5 | 5 | Y | Y | Y | 5 | 5 | 5 | Y | 5 | 5 |
| 50 | F | 5 | 5 | 5 | Y | Y | Y | 5 | 5 | 5 | Y | 5 | 5 |
| 15 | M | 5 | 5 | 5 | Y | Y | Y | 5 | 5 | 5 | Y | 5 | 5 |
| 61 | M | 5 | 5 | 5 | Y | Y | Y | 5 | 5 | 5 | Y | 5 | 5 |
| 46 | M | 5 | 5 | 5 | Y | Y | Y | 5 | 5 | 5 | Y | 5 | 5 |
| 33 | F | 5 | 5 | 5 | Y | Y | Y | 5 | 5 | 5 | Y | 5 | 5 |
| 53 | M | 5 | 5 | 5 | Y | Y | Y | 5 | 5 | 5 | Y | 5 | 5 |
| 14 | F | 5 | 5 | 5 | Y | Y | Y | 5 | 5 | 5 | Y | 5 | 5 |
| 66 | M | 5 | 5 | 5 | Y | Y | Y | 5 | 5 | 5 | Y | 5 | 5 |
| 30 | F | 5 | 5 | 5 | Y | Y | Y | 5 | 5 | 5 | Y | 5 | 5 |
| 30 | M | 5 | 5 | 5 | Y | Y | Y | 5 | 5 | 5 | Y | 5 | 5 |
| 20 | M | 5 | 5 | 5 | Y | Y | Y | 5 | 5 | 5 | Y | 5 | 5 |
| 59 | F | 5 | 5 | 5 | Y | Y | Y | 5 | 5 | 5 | Y | 5 | 5 |

Good Sept '97

Limited and dissatisfied responses highlighted

INDIVIDUAL RESPONSES

SECTION 3

| AGE | GENDER | MEDICAL CARE | | | | | | OFFICE PROCEDURES | | | OVERALL FEELING | INSURANCE |
|---|---|---|---|---|---|---|---|---|---|---|---|---|
| | | Q3 | Q4 | Q8 | Q12 | Q14 | Q15 | Q1 | Q2 | Q5 | Q6 | Q7 |
| 54 | M | 5 | 5 | 5 | Y | Y | Y | 5 | 5 | 4 | 5 | 5 |
| 10 | M | 5 | 5 | 5 | Y | Y | Y | 5 | 5 | 5 | 5 | 5 |
| 37 | F | 5 | 5 | 5 | Y | Y | Y | 5 | 4 | 5 | 5 | 5 |
| 32 | M | 5 | 5 | 5 | Y | Y | Y | 5 | 5 | 5 | 5 | 5 |
| 46 | M | 5 | 5 | 5 | Y | Y | Y | 5 | 5 | 5 | 5 | 4 |
| 56 | F | 5 | 5 | 5 | Y | Y | * | 5 | 5 | * | 5 | 5 |
| 11 | M | 5 | 5 | 4 | Y | Y | Y | 5 | 5 | 4 | 5 | 5 |
| 34 | M | 5 | 5 | 5 | Y | Y | Y | 5 | 5 | 5 | 5 | 4 |
| 22 | F | 5 | 5 | 5 | Y | Y | Y | 5 | 5 | 5 | 5 | 5 |
| 39 | F | 5 | 5 | 5 | Y | Y | Y | 5 | 5 | 5 | 5 | 4 |
| 35 | M | 5 | 5 | 5 | Y | Y | Y | 5 | 5 | 5 | 5 | 5 |
| 0 | M | 5 | 5 | 5 | Y | Y | Y | 5 | 5 | 4 | 5 | 4 |
| 32 | F | 5 | 5 | 5 | Y | Y | Y | 5 | 5 | 5 | 5 | 5 |
| 28 | F | 5 | 5 | 5 | Y | Y | * | 5 | 5 | 4 | 5 | 4 |
| 61 | M | 5 | 5 | 5 | Y | Y | Y | 5 | 5 | 5 | 5 | 5 |
| ** | ** | 5 | 5 | 5 | Y | Y | Y | 5 | 5 | 5 | 5 | 4 |
| 45 | F | 5 | 5 | 5 | Y | Y | Y | 5 | 5 | 4 | 5 | 4 |
| 29 | F | 5 | 5 | 5 | Y | Y | Y | 5 | 5 | 5 | 5 | 5 |
| 61 | M | 5 | 5 | 5 | Y | Y | Y | 5 | 5 | 5 | 5 | 4 |
| 78 | M | 5 | 5 | 5 | Y | Y | Y | 5 | 5 | 5 | 5 | 5 |
| ** | ** | 5 | 5 | * | * | * | * | * | * | * | 5 | 5 |
| 67 | M | 5 | 5 | 5 | Y | Y | Y | 5 | 5 | 5 | 5 | 5 |
| 52 | M | 5 | 5 | 5 | Y | N | Y | 5 | 5 | 5 | 5 | 4 |
| 32 | M | 5 | 5 | 5 | Y | Y | Y | 5 | 5 | 5 | 5 | 5 |
| 37 | F | 5 | 5 | 5 | Y | Y | * | 5 | 5 | 5 | 5 | 5 |
| 42 | M | 5 | 5 | 5 | Y | Y | Y | 5 | 5 | 5 | 5 | 5 |
| 65 | M | 5 | 5 | 5 | Y | Y | Y | 5 | 5 | 5 | 5 | 5 |
| 91 | F | 5 | 5 | 5 | * | * | * | 5 | 5 | * | 5 | 5 |
| 74 | M | 5 | 5 | 5 | Y | Y | Y | 5 | 5 | 5 | 5 | 5 |
| 95 | M | * | * | * | * | * | * | 5 | 5 | 5 | * | * |
| 10 | F | * | * | * | * | * | * | * | * | * | * | * |
| 50 | M | * | * | * | * | * | * | * | * | * | * | * |
| ** | F | * | * | * | * | * | * | * | * | * | * | * |
| 95 | M | * | * | * | * | * | * | 4 | * | * | * | * |
| ** | ** | * | * | * | * | * | * | * | * | * | * | * |

Good Sept '97

* Neutral and dissatisfied responses highlighted

Good Sept '97

DIAGNOSIS GROUPS

SATISFACTION BY DIAGNOSIS GROUP:

CURRENT MONTH

| Diagnosis Group | Cases | Avg. Age | %Female | No. Visits | Medical Care | Office Procedures | Overall Feeling | Insurance |
|---|---|---|---|---|---|---|---|---|
| Asthma | 1 | 32 | 100% | 5.0 | * | * | * | * |
| CHF | 2 | 54 | 50% | 6.5 | * | * | * | * |
| COPD | 5 | 53 | 50% | 1.8 | * | * | * | * |
| Diabetes | 1 | 95 | 0% | ** | * | * | * | * |
| Oncological | 5 | 31 | 33% | 1.7 | * | * | * | * |
| Practice Target | 81 | 43 | 47% | 4.2 | 14% | 17% | 10% | 26% |

YEAR-TO-DATE

| Diagnosis Group | Cases | Avg. Age | %Female | No. Visits | Medical Care | Office Procedures | Overall Feeling | Insurance |
|---|---|---|---|---|---|---|---|---|
| Asthma | 16 | 43 | 75% | 2.2 | 25% | 25% | 19% | 31% |
| CHF | 12 | 58 | 67% | 5.0 | 8% | 8% | 8% | 8% |
| COPD | 12 | 48 | 55% | 1.9 | 17% | 17% | 17% | 25% |
| Diabetes | 11 | 38 | 36% | 0.8 | 45% | 27% | 0% | 27% |
| Oncological | 9 | 27 | 71% | 1.8 | * | * | * | * |
| Practice Target | 325 | 44 | 45% | 2.3 | 11% | 17% | 8% | 20% |

NOTE: Domains represented as (Negative Responses/Total Responses).
* Domain percentages were not calculated for groups with less than ten cases.

SECTION 4

-45-

Good Sept '97

SATISFACTION with INSURANCE

Patient Activity

| Insurance | April | May | June | July | August |
|---|---|---|---|---|---|
| Blue Cross | N/A | N/A | 13 | 1 | 0 |
| Medicare | N/A | N/A | 4 | 2 | 2 |
| Medicare HMO | N/A | N/A | 12 | 0 | 0 |
| HMO | N/A | N/A | 28 | 9 | 2 |
| Other | N/A | N/A | 35 | 10 | 3 |

Percent of Patients Not Satisfied*

| Insurance | April | May | June | July | August |
|---|---|---|---|---|---|
| Blue Cross | N/A | N/A | 0% | 0% | 0% |
| Medicare | N/A | N/A | 0% | 50% | 0% |
| Medicare HMO | N/A | N/A | 0% | 0% | 0% |
| HMO | N/A | N/A | 4% | 22% | 0% |
| Other | N/A | N/A | 23% | 30% | 67% |

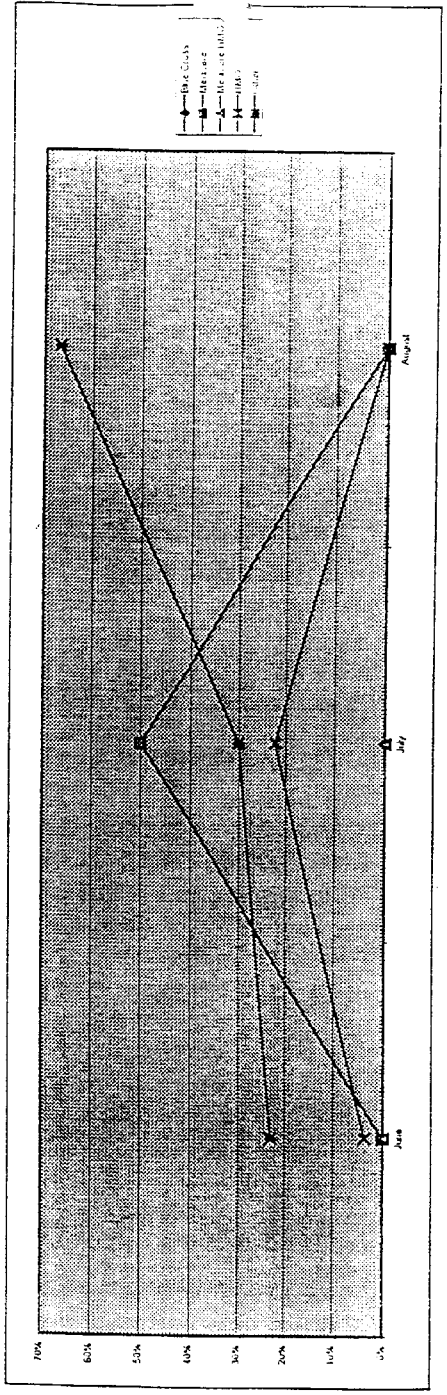

PATIENT SATISFACTION with INSURANCE:

* Neutral or dissatisfied responses/total responses.

SECTION 5

-46-

PulsePilot table descriptions          APPENDIX C answer.db    contains the answer information per survey
batch.db     holds the current batch number
d   ns.dd    contains the answer information for duplicate answers
dupptans.db  holds all the answers from the pilot for duplicates only
pcans.db     holds the PC entered data
pcque.db     holds the PC question text
pilotans.db  holds the Pilot entered data
pilotque.db  holds the Pilot question definitions (for future use)
survey.db    holds the ID for a survey and it's name

```
answer.db

Field name      Type                                            Size
AnswerSetID     Auto-incrementing 32-bit integer counter field  4      primary key
PilotAppID      Character or string field                       4
P   hNum        32-bit integer field                            4
    eyNum       32-bit integer field                            4
PilotData       Boolean field                                   2
PilotDate       Date field                                      4
PCData          Boolean field                                   2
PCDate          Date field                                      4
``` batch.DB

| Field name | Type | Size | |
|---|---|---|---|
| PilotAppID | Character or string field | 4 | primary key |
| Batch | 32-bit integer field | 4 | |
| S  eyPrint | 32-bit integer field | 4 | |

```
dupans.db

Field name          Type                                              Size

AnswerSetID         Auto-incrementing 32-bit integer counter field    4       primary key
PilotAppID          Character or string field                         4
F   hNum            32-bit integer field                              4
S   eyNum           32-bit integer field                              4
PilotDate           Date field                                        4
```

−50−

```
dupptans.db

Field name        Type                                            Size

AnswerID          Auto-incrementing 32-bit integer counter field   4    primary key
AnswerSetID       32-bit integer field                             4
?   tionID        32-bit integer field                             4
Q   .tionNum      32-bit integer field                             4
Answer            Character or string field                       10
```

```
?cans.DB

Field name          Type                                              Size

AnswerID            Auto-incrementing 32-bit integer counter field    4      primary key
AnswerSetID         32-bit integer field                              4
   tionID           32-bit integer field                              4
   .tionNum         32-bit integer field                              4
Answer              Character or string field                         30
```

```
pcque.DB

Field name      Type                                            Size

QuestionID      Auto-incrementing 32-bit integer counter field    4      primary key
PilotAppID      Character or string field                         4
(   tionNum     32-bit integer field                              4
(    .tion      Character or string field                        30
```

```
pilotans.DB

Field name      Type                                            Size

AnswerID        Auto-incrementing 32-bit integer counter field  4      primary key
AnswerSetID     32-bit integer field                            4
(  tionID       32-bit integer field                            4
(  tionNum      32-bit integer field                            4
Answer          Character or string field                       10
```

-54-

```
pilotque.DB

Field name          Type                                            Size

QuestionID          Auto-incrementing 32-bit integer counter field  4      primary key
PilotAppID          Character or string field                       4
    tionNum         32-bit integer field                            4
Q.  tionType        32-bit integer field                            4
Question            Character or string field                       30
``` survey.db

| Field name | Type | Size | |
|---|---|---|---|
| PilotAppID | Character or string field | 4 | primary key |
| Name | Character or string field | 30 | |

CDEMO                    APPENDIX D       14Jul1997 12:32 Page    1

Function Caller/Called Summary Tree
***********************************

2 PULSE.C        1 PilotMain
                     |
   36 PULSE.C        2 |->InitApp
                     3 |  :..EvtEnableGraffiti
                     |
   43 PULSE.C        4 |->EventLoop
                     |  |
   69 PULSE.C        5 |  |->ApplicationHandleEvent
                     6 |  |  :..FrmInitForm FrmSetActiveForm
                     |  |  |..FrmSetEventHandler
                     |  |
                     7 |  :..EvtGetEvent FrmDispatchEvent
                     |
                     8 :..FrmGotoForm

```
EMO                                         14Jul1997 12:40  Page    1 nction Caller/Called Summary Tree
********************************

QUESTION.C        1 ButtonsHandleEvent
                          2 :..FrmGetActiveForm FrmGetActiveFormID
                            |..FrmGetControlGroupSelection FrmGetObjectIndex
                            |..FrmGotoForm FrmAlert FrmDrawForm 96  QUESTION.C        3 NumericHandleEvent
                            |
   157  QUESTION.C        4 |->GetObjectPtr
                          5 |  :..FrmGetActiveForm FrmGetObjectPtr
                            |  |..FrmGetObjectIndex
                            |
                          6 :..FrmGetActiveForm FrmGetActiveFormID FldGetTextPtr
                            |..FldGetTextLength UpdateDBRecord FrmGotoForm
                            |..FldDelete FldGetMaxChars FldInsert FldDrawField
                            |..FrmDrawForm 52  QUESTION.C        7 Q9HandleEvent
                          8 :..FrmGetActiveForm FrmGetControlGroupSelection
                            |..FrmGetObjectIndex FrmGotoForm FrmAlert FrmDrawForm
```

CDEMO                                          14Jul1997 12:41 Page    1

Function Caller/Called Summary Tree
***********************************

8 STRTFORM.C        1 StartHandleEvent
                        2 :..FrmGetActiveForm FrmGotoForm FrmDrawForm

What is claimed:

1. A system for acquisition, management and processing of patient clinical information and patient satisfaction information received from a plurality of physician practices to provide practice performance information for a physician practice, the system comprising:

means for receiving data from a survey form, the data including a physician component to receive the patient clinical information and a patient component to receive the patient satisfaction information, to provide practice-patient data;

database processing means for translating the practice-patient data to a predetermined format and for storing the practice-patient data having the predetermined format in a database;

data analysis means for
a) selectively receiving practice-patient data from the database,
b) analyzing the received practice-patient data, and
c) summarizing the patient satisfaction information with respect to the clinical information to provide performance results of the physician practice; and data correlating means for correlating selected portions of the performance results associated with at least one of the plurality of physician practices with portions of the stored practice-patient data to provide a practice measure; and reporting means for generating a report from the performance results and the practice measures, wherein data correlating means correlates selected portions of the performance results to provide the practice measure as a relative measure of practice quality based on a comparison of the patient satisfaction information of the plurality of physician practices.

2. The system as recited in claim 1, further including an enrollment processing means for collecting respective enrollment data of each one of the plurality of physician practices, the enrollment data corresponding to at least one of physician practice identification, physician identification, physician diagnostic information, specialty information, patient demographic information, and practice cost information.

3. The system as recited in claim 1, wherein the survey form includes a plurality of survey questions, and the system further includes a processor to provide each one of the plurality of survey questions, the processor including means for 1) receiving a draft base question, 2) evaluating the draft base question according to a sample response of patient population, and 3) modifying the draft base question to provide one of the plurality of survey questions.

4. The system as recited in claim 1, wherein the means for receiving data employs a survey form which is machine-readable form and includes a scanner to read the data from the survey form.

5. The system as recited in claim 1, wherein the means for receiving data employs a survey form which is presented as a plurality of screens on a hand-held computer, each screen including a single survey question, the hand-held computer receiving each response value to the respective question as one portion of the patient clinical information and the patient satisfaction information, and the reading means includes a host computer having a communications interface to the hand-held computer, the host computer receiving the patient clinical information and the patient satisfaction information from the hand-held computer through the communications interface.

6. The system as recited in claim 1, further comprising:
outcomes measuring means including processing means for
a) periodically selectively receiving performance results,
b) storing the selected performance results,
c) identifying a trend present in the stored performance results, and
d) tracking a trend present in the stored performance results.

7. The system as recited in claim 6, wherein:
the performance results include at least one domain measure, each domain measure defining a practice characteristic.

8. The system as recited in claim 7, wherein each domain measure further includes at least one of a practice specific component and a practice population component, the practice specific component representing a perceived patient satisfaction of one physician practice of the plurality of physician practices, and the practice population component representing a respective comparison of the one physician practice to the plurality of physician practices for the domain measure.

9. The system as recited in claim 7, wherein each domain measure is selected from the group consisting of a quality of medical treatment, a quality of office procedures, a quality of insurance and a quality of practice satisfaction.

10. The system as recited in claim 7, wherein each domain measure includes a plurality of practice satisfaction variables, and the reporting means further includes:
remote-processing means for locally receiving predetermined practice parameters, each practice parameter corresponding to at least a selected one of the plurality of practice satisfaction variables, and the data analysis means analyzes the received practice patient data based on the received practice parameters, thereby to provide each domain measure of the performance results.

11. The system as recited in claim 1, wherein:
the system is a personal disease management assistant system, and wherein the means for receiving data comprises:
a hand-held computer, the hand-held computer: storing at least one survey form, each survey form including at least one section to receive the patient clinical and satisfaction information, wherein the survey form is presented as a plurality of screens on the hand-held computer, each screen including at least one survey question, the hand-held computer:
1) receiving each response value to each respective question as one portion of the patient clinical and satisfaction information; and
2) storing at least one disease profile, the disease profile including at least one of a treatment regimen and a prescription regimen;
wherein the handheld computer includes means for 1) associating each survey form with the disease profile and 2) indicating a treatment event based on the disease profile, wherein the handheld computer provides at least one survey form associated with the treatment event; and
wherein the database processing means further comprises
a host computer having a communications interface to the hand-held computer, the host computer receiving the patient clinical and satisfaction information from the hand-held computer through the communications interface to provide practice-patient data.

12. A system for acquisition, management and processing of patient clinical information and patient satisfaction information received from a plurality of physician practices to provide practice performance information, the system comprising:

a hand-held computer, the hand-held computer storing at least one survey form, the survey form including at least one of a physician section to receive the patient clinical information and a patient section to receive the patient satisfaction information, wherein the survey form is presented as a plurality of screens on the hand-held computer, each screen including a single survey question, the hand-held computer receiving each response value to the respective question as one portion of the patient clinical information and the patient satisfaction information;

a host computer having a communications interface to the hand-held computer, the host computer receiving the patient clinical information and the patient satisfaction information from the hand-held computer through the communications interface to provide practice-patient data;

database processing means for translating the practice-patient data to a predetermined format and for storing the practice-patient data having the predetermined format in a database;

data analysis means for
        a) selectively receiving practice-patient data from the database,
        b) analyzing the received practice patient data, and
        c) summarizing patient satisfaction information with respect to the clinical information to provide performance results of the physician practice;

data correlating means for correlating selected portions of the performance results associated with at least one of the plurality of physician practices with portions of the stored practice-patient data to provide a practice measure; and reporting means for periodically generating a report based on the performance results, wherein data correlating means correlates selected portions of the performance results to provide the practice measure as a relative measure of practice quality based on a comparison of the patient satisfaction information of the plurality of physician practices.

13. The system as recited in claim 12, wherein the host computer further includes means for receiving and storing at least one physician diagnostic information record and an associated patient identification (ID), the handheld computer associates the patient ID with each survey form, and the host computer associates the received the patient clinical information and the patient satisfaction information of each respective form with the physician diagnostic information record of which the patient ID matches the patient ID of the respective form to form a physician/patient data pair having the respective patient ID.

14. The system as recited in claim 13, wherein the host computer further includes a correlation processor, the correlation processor receiving each physician/patient data pair, and the correlation processor including means for comparing patient clinical information, the patient satisfaction information, and the physician diagnostic information of the physician/patient pair to identify at least one data exception, and includes means for resolving each data exception.

15. The system as recited in claim 12, wherein the database further includes a plurality of survey forms, the host computer includes a database interface, and means for downloading and storing selected ones of the plurality of survey forms, and the at least one survey form of the handheld computer is received through the communications interface from the host computer.

16. The system as recited in claim 15, wherein each one of the plurality of survey forms is associated with a respective diagnostic program.

17. A method of acquisition, management and processing of patient clinical information and patient satisfaction information received from a plurality of physician practices to provide practice performance information, the method comprising the steps of:

a) providing, with a survey form, survey questions including a physician section including questions related to the patient clinical information and a patient section including questions related to the patient satisfaction information;

b) receiving data representing answers to the questions;

c) providing the patient clinical information and the patient satisfaction information as practice-patient data;

d) translating the practice-patient data to a predetermined format;

e) storing the practice-patient data having the predetermined format in a database;

f) selectively receiving practice-patient data from the database;

g) analyzing the received practice patient data;

h) summarizing patient satisfaction information with respect to the clinical information to provide performance results of the physician practice;

i) correlating selected portions of the performance results associated with at least one of the plurality of physician practices with portions of the stored practice-patient data to provide a practice measure; and j) periodically generating a report of the practice measure based upon the provided performance results, the report providing the practice measure as a relative measure of practice quality based on a comparison of the patient satisfaction information of the plurality of physician practices.

18. The method as recited in claim 17, further including the steps of collecting respective enrollment data of each one of the plurality of physician practices, the enrollment data corresponding to at least one of physician practice identification, physician identification, physician diagnostic information, specialty information, patient demographic information, and practice cost information.

19. The method as recited in claim 17, wherein the survey form includes a plurality of survey questions, and the method further includes the steps of a1) receiving a draft base question, a2) evaluating the draft base question according to a sample response of a patient population, and a3) modifying the draft base question to provide one of the plurality of survey questions.

20. The method as recited in claim 17, wherein the providing step c) provides the questions with a machine readable form, and the receiving data step includes the step of reading the data from the machine readable survey form with a scanner.

21. The method as recited in claim 17, the method further comprising the steps of a1) presenting the survey form as a plurality of screens on a hand-held computer, each screen including a single survey question, a2) receiving each response value to the respective question as one portion of the patient clinical information and the patient satisfaction information, and b1) receiving, by a host computer, the patient clinical information and the patient satisfaction information from the hand-held computer through a communications interface of the host computer.

* * * * *